US009658207B2

(12) United States Patent
Tang et al.

(10) Patent No.: US 9,658,207 B2
(45) Date of Patent: May 23, 2017

(54) POLYMER MICROFILTRATION DEVICES, METHODS OF MANUFACTURING THE SAME AND THE USES OF THE MICROFILTRATION DEVICES

(71) Applicant: Creatv Microtech, Inc., Potomac, MD (US)

(72) Inventors: Cha-Mei Tang, Potamac, MD (US); Yunqi Zhang, Gaithersburg, MD (US)

(73) Assignee: CREATV MICROTECH, INC., Potomac, MD (US)

( * ) Notice: Subject to any disclaimer, the term of this patent is extended or adjusted under 35 U.S.C. 154(b) by 224 days.

(21) Appl. No.: 14/359,467

(22) PCT Filed: Nov. 21, 2012

(86) PCT No.: PCT/US2012/066390
§ 371 (c)(1),
(2) Date: May 20, 2014

(87) PCT Pub. No.: WO2013/078409
PCT Pub. Date: May 30, 2013

(65) Prior Publication Data
US 2014/0322743 A1    Oct. 30, 2014

Related U.S. Application Data

(63) Continuation-in-part of application No. PCT/US2011/030966, filed on Apr. 1, 2011.
(Continued)

(51) Int. Cl.
*B01D 39/16*    (2006.01)
*G01N 33/50*    (2006.01)
(Continued)

(52) U.S. Cl.
CPC ......... *G01N 33/5005* (2013.01); *B01D 29/00* (2013.01); *B01D 39/16* (2013.01);
(Continued)

(58) Field of Classification Search
None
See application file for complete search history.

(56) References Cited

U.S. PATENT DOCUMENTS

| 1,564,499 A | * | 12/1925 | Tropp | ............ A61M 5/32 |
| | | | | 604/241 |
| 3,010,583 A | * | 11/1961 | Kenyon | ............ G01N 1/14 |
| | | | | 210/406 |

(Continued)

FOREIGN PATENT DOCUMENTS

| EP | 1031371 A1 | 8/2000 |
| GB | 2392854 A | 3/2014 |

(Continued)

*Primary Examiner* — Krishnan S Menon
(74) *Attorney, Agent, or Firm* — Dickinson Wright PLLC

(57) ABSTRACT

A microfilter comprising a polymer layer formed from epoxy-based photo-definable dry film, and a plurality of apertures each extending through the polymer layer. A microfilter comprising two or more polymer layers formed from epoxy-based photo-definable dry film, and a plurality of apertures or open areas each extending through the polymer layer. A method of forming a microfilter is also disclosed. The method includes providing a first layer of epoxy-based photo-definable dry film disposed on a substrate, exposing the first layer to energy through a mask to form a pattern, defined by the mask, in the first layer of dry film, forming, from the exposed first layer of dry film, a polymer layer having a plurality of apertures extending therethrough, the plurality of apertures having a distribution defined by the pattern, and removing the polymer layer from the substrate. Unique filter holder designs and methods appropriate to hold microfilters to collect the rare cells and
(Continued)

allow performing assays in the filter holder are provided. The invention also describes the use of the microfilter and filter holder to collect rare cells from body fluids and perform assays. Rare cells collected on the microfilter in accordance with embodiments of the present invention can be used for medical and biological research applications.

31 Claims, 44 Drawing Sheets

Related U.S. Application Data

(60) Provisional application No. 61/654,636, filed on Jun. 1, 2012, provisional application No. 61/618,641, filed on Mar. 30, 2012, provisional application No. 61/562,404, filed on Nov. 21, 2011.

(51) Int. Cl.
    *B01D 29/00*     (2006.01)
    *G01N 1/40*     (2006.01)
    *B01L 3/00*     (2006.01)
    *B01L 9/00*     (2006.01)

(52) U.S. Cl.
    CPC ............ *B01D 39/1692* (2013.01); *B01L 3/50* (2013.01); *B01L 3/5635* (2013.01); *B01L 9/00* (2013.01); *G01N 1/4005* (2013.01); *G01N 1/4077* (2013.01); *B01L 3/502* (2013.01); *B01L 2300/0681* (2013.01); *G01N 2001/4088* (2013.01); *Y10T 29/49826* (2015.01); *Y10T 29/49963* (2015.01)

(56) References Cited

U.S. PATENT DOCUMENTS

| | | | |
|---|---|---|---|
| 4,454,749 A | 6/1984 | Guillemin et al. | |
| 4,783,318 A | 11/1988 | Lapakko | |
| 5,049,268 A | 9/1991 | Kopf | |
| 5,221,483 A * | 6/1993 | Glenn | A61L 2/0017 210/321.64 |
| 5,782,820 A * | 7/1998 | Roland | A61B 5/1438 600/577 |
| 6,241,886 B1 | 6/2001 | Kitagawa et al. | |
| 6,346,192 B2 * | 2/2002 | Buhr | 210/314 |
| 2003/0010708 A1 | 1/2003 | Leocavallo et al. | |
| 2003/0213738 A1 | 11/2003 | Hiranaga et al. | |
| 2004/0112213 A1 | 6/2004 | Dominiak et al. | |
| 2004/0182788 A1 | 9/2004 | Dorian et al. | |
| 2008/0169227 A1 | 7/2008 | Assion | |
| 2009/0202813 A1 * | 8/2009 | Itami | B01D 67/0006 428/319.3 |
| 2010/0038303 A1 | 2/2010 | Cai et al. | |
| 2010/0089815 A1 | 4/2010 | Zhang et al. | |

FOREIGN PATENT DOCUMENTS

| | | |
|---|---|---|
| JP | 54-23139 | 2/1979 |
| JP | 58-68899 U | 5/1983 |
| JP | 60-132803 U | 9/1985 |
| JP | 62-121331 A | 6/1987 |
| JP | 3-500003 A | 1/1991 |
| JP | 6-500403 A | 1/1994 |
| JP | 6-507375 A | 8/1994 |
| JP | 10-508699 A | 8/1998 |
| JP | 2000-237553 A | 9/2000 |
| JP | 2001-299730 A | 10/2001 |
| JP | 2001-324500 A | 11/2001 |
| JP | 2003-194806 A | 7/2003 |
| JP | 2004-212250 A | 7/2004 |
| JP | 2008-000038 A | 1/2008 |
| WO | 89/01966 A1 | 3/1989 |
| WO | 92/00132 A1 | 1/1992 |
| WO | 92/17110 A1 | 10/1992 |
| WO | 96/14563 A1 | 5/1996 |

* cited by examiner

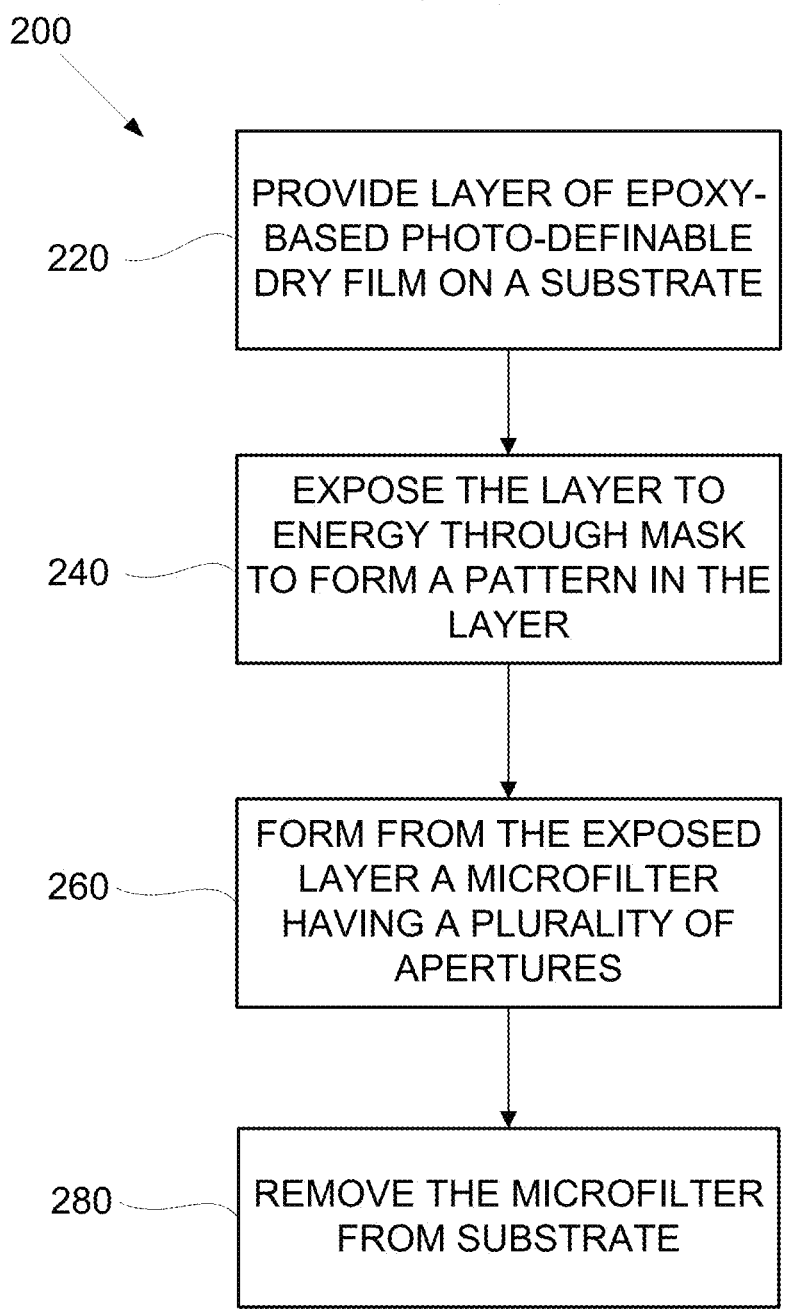

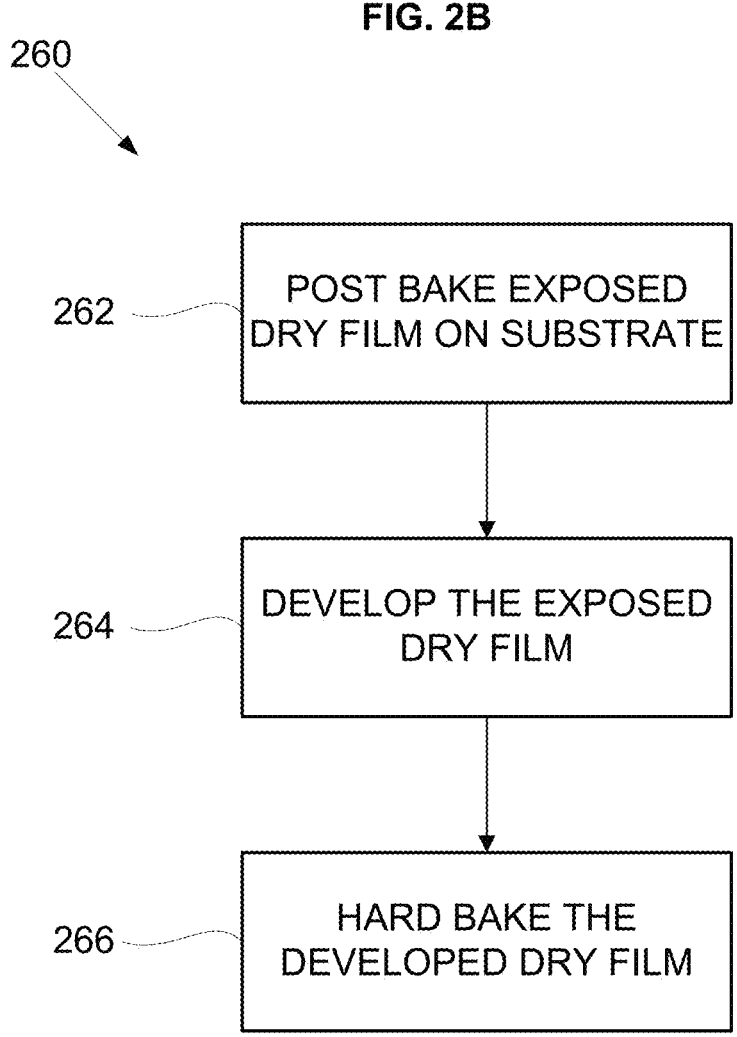

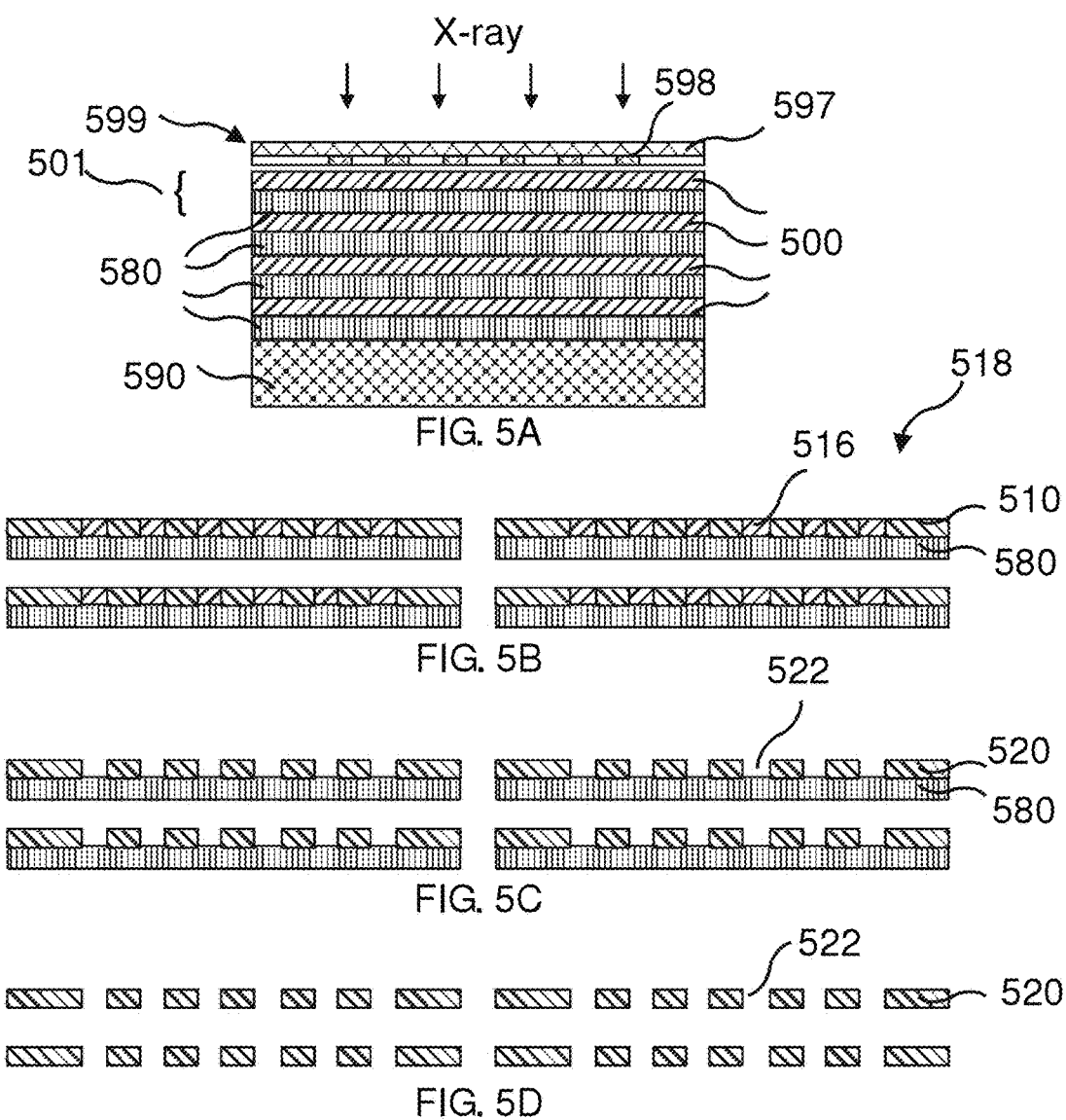

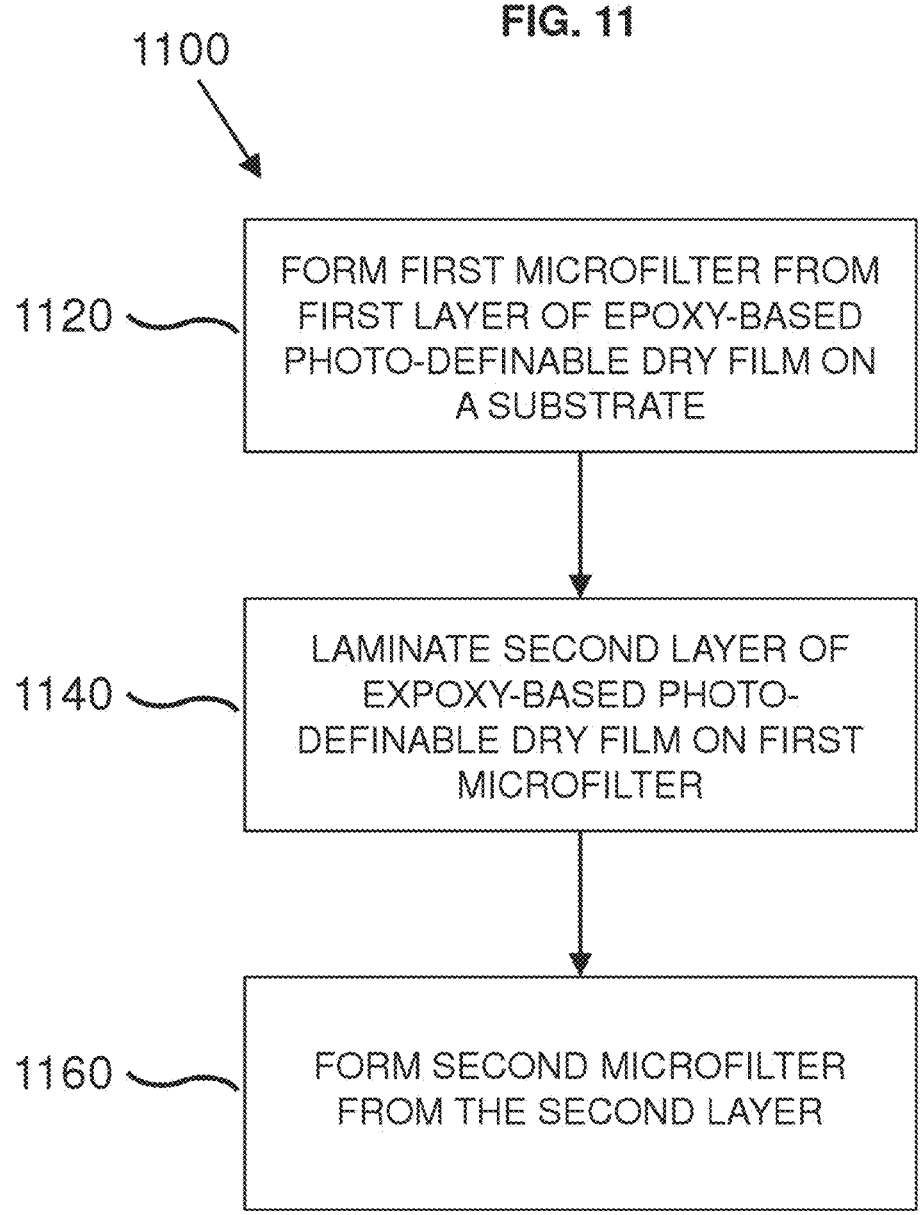

POLYMER MICROFILTRATION DEVICES, METHODS OF MANUFACTURING THE SAME AND THE USES OF THE MICROFILTRATION DEVICES

CROSS-REFERENCE TO RELATED APPLICATIONS

This application is a national stage application of the PCT patent application No. PCT/US2012/66390, filed Nov. 21, 2012, which is a continuation in part of prior application titled, "POLYMER MICROFILTERS AND METHODS OF MANUFACTURING THE SAME", PCT/US11/30966, which was filed on Apr. 1, 2011.

This application also claims priority to prior application titled, "POLYMER MICROFILTRATION DEVICES, METHODS OF MANUFACTURING THE SAME AND THE USES OF THE MICROFILTRATION DEVICES", U.S. Provisional Patent Application No. 61/562,404 filed Nov. 21, 2011, the contents of which are hereby incorporated by reference herein.

This application also claims priority to prior application titled, "POLYMER MICROFILTRATION DEVICES, METHODS OF MANUFACTURING THE SAME AND THE USES OF THE MICROFILTRATION DEVICES", U.S. Provisional Patent Application No. 61/618,641 filed Mar. 30, 2012, the contents of which are hereby incorporated by reference herein.

This application also claims priority to prior application titled, "POLYMER MICROFILTRATION DEVICES, METHODS OF MANUFACTURING THE SAME AND THE USES OF THE MICROFILTRATION DEVICES", U.S. Provisional Patent Application No. 61/654,636 filed Jun. 1, 2012, the contents of which are hereby incorporated by reference herein

BACKGROUND

Field of the Invention

The present invention relates generally to microfiltration devices, that contain polymer microfilters, methods of manufacturing the same, methods to use the microfiltration device, and applications of the devices.

Related Art

Some medical conditions may be diagnosed by detecting the presence of certain types of cells in bodily fluid. In particular, cells indicative or characteristic of certain medical conditions may be larger and/or less flexible than other cells found in certain bodily fluids. Accordingly, by collecting such larger and/or less flexible cells from a liquid sample of a bodily fluid, it may be possible to diagnose a medical condition based on the cells collected.

Cells larger and/or less flexible than other cells present in a bodily fluid may be collected by filtering the bodily fluid. For example, targeted cells indicative of a condition may be collected by passing a bodily fluid through a filter having openings that are too small for the target cells to pass through, but large enough for other cells to pass through. Once collected, any number of analyses of the target cells may be performed. Such analyses may include, for example, identifying, counting, characterizing, and/or culturing the collected cells.

It is desirable for microfilters to have precise pore dimensions, not break during use, and not be autofluorescent for fluorescent microscope imaging. Conventionally, microfilters are installed in a microfiltration device and liquid samples processed to collect cells based on size on the microfilter.

SUMMARY

In one aspect of the present invention, a microfilter is disclosed. According to an exemplary embodiment, a microfilter comprises a polymer layer formed from epoxy-based photo-definable dry film, and a plurality of apertures each extending through the polymer layer.

In another aspect of the present invention, multi-layer microfilters are disclosed. According to an exemplary embodiment, a microfilter comprises a first polymer layer formed from epoxy-based photo-definable dry film and having a first aperture extending therethrough, and a second polymer layer formed from epoxy-based photo-definable dry film and having a second aperture extending therethrough, wherein the first and second apertures at least partially define a non-linear passage extending through the first and second layers.

In yet another aspect of the present invention, a method of manufacturing a microfilter is disclosed. According to an exemplary embodiment, a method comprises providing a first layer of epoxy-based photo-definable dry film disposed on a substrate, exposing the first layer to energy through a mask to form a pattern, defined by the mask, in the first layer of dry film, forming, from the exposed first layer of dry film, a polymer layer having a plurality of apertures extending therethrough, the plurality of apertures having a distribution defined by the pattern, and removing the polymer layer from the substrate.

In yet another aspect of the present invention, a method of forming a multi-layer microfilter is disclosed. According to an exemplary embodiment, a method comprises forming a first polymer layer comprising a plurality of first apertures from a first layer of epoxy-based photo-definable dry film disposed on a substrate, laminating a second layer of epoxy-based photo-definable dry film on the first polymer layer, and forming a second polymer layer comprising a plurality of second apertures from the second layer of dry film.

In one aspect of the present invention, filter holders to hold the microfilter are disclosed. According to an exemplary embodiment, filter holders are designed to keep the filter flat and fixed in place, allowing the implementation of various assay steps with ease.

In yet another aspect of the present invention, a method of using a microfilter is disclosed. According to an exemplary embodiment, a method comprises passing a liquid through a plurality of apertures of a microfilter formed from an epoxy-based photo-definable dry film, wherein the microfilter has sufficient strength and flexibility to filter the liquid, and wherein the apertures are sized to allow passage of a first type of bodily fluid cell and to prevent passage of a second type of bodily fluid cell. An exemplary implementation includes application of a negative pressure using either vacuum or filter holder connect to syringe(s), which can be performed manually, semi-manually using a syringe pump, or automated.

In an exemplary implementation, filters can be coated with analyte recognition reagents to capture cells of interest from the body fluids.

In yet another exemplary implementations of embodiments of the present invention, methods to collect liquid sample and shipping the filtered liquid sample using the microfilter inside the filter holder are also described.

In yet other exemplary implementations of embodiments of the present invention, methods of using the microfilters to perform assays are disclosed. Exemplary embodiment of the present invention provide methods to isolate cells, methods to recover the cells from the microfilter by backwashing using the filter holder, and methods to perform assay inside the filter holder.

In yet another aspect of the present invention, exemplary medical applications of the assays are disclosed.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 2A is a flowchart illustrating a process for manufacturing a microfilter in accordance with exemplary embodiments of the present invention;

FIG. 2B is a flowchart illustrating a process for forming a microfilter from an exposed dry film in the process illustrated in FIG. 2A, in accordance with exemplary embodiments of the present invention;

FIGS. 5A-5D are cross-sectional views illustrating multiple stages in a process for manufacturing a plurality of microfilters from a plurality of layers of epoxy-based photo-definable dry film in accordance with exemplary embodiments of the present invention;

FIG. 11 is a flow chart illustrating a process 1300 for manufacturing a multi-layer microfilter in accordance with exemplary embodiments of the present invention;

DETAILED DESCRIPTION OF EXEMPLARY EMBODIMENTS

Figure 1A:
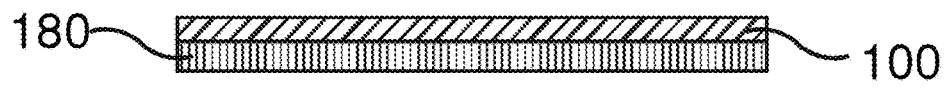
FIGS. 1A-1E are cross-sectional views illustrating multiple stages in a process for manufacturing a microfilter in accordance with exemplary embodiments of the present invention.

Referring now to the drawings, wherein like reference numerals designate identical or corresponding parts throughout the several views, embodiments of the present invention are shown in schematic detail.

The matters defined in the description such as a detailed construction and elements are nothing but the ones provided to assist in a comprehensive understanding of the invention. Accordingly, those of ordinary skill in the art will recognize that various changes and modifications of the embodiments described herein can be made without departing from the scope and spirit of the invention. Also, well-known functions or constructions are omitted for clarity and conciseness. Some exemplary embodiments of the present invention are described below in the context of commercial applications. Such exemplary implementations are not intended to limit the scope of the present invention, which is defined in the appended claims Aspects of the present invention are generally directed to a microfilter comprising a polymer layer formed from an epoxy-based photo-definable dry film. The microfilter includes a plurality of apertures each extending through the polymer layer. In certain embodiments, the microfilter may be formed by exposing the dry film to energy through a mask and developing the exposed dry film. In some embodiments, the dry film may be exposed to energy in the form of ultraviolet (UV) light. In other embodiments, the dry film may be exposed to energy in the form of X-rays. In certain embodiments, the polymer layer has sufficient strength and flexibility to filter liquid. In some embodiments, the apertures are sized to allow passage of a first type of bodily fluid cell and to prevent passage of a second type of bodily fluid cell.

Specifically, in certain embodiments, the microfilter may be used to perform assays on bodily fluids. In some embodiments, the microfilter may be used to isolate and detect large rare cells from a bodily fluid. In certain embodiments, the microfilter may be used to collect circulating tumor cells (CTCs) from peripheral blood from cancer patients passed through the microfilter. In certain embodiments, the microfilter may be used to collect circulating endothelial cells, fetal cells and other large cells from the blood and body fluids. In certain embodiments, the microfilter may be used to collect large cells from processed tissue samples, such as bone marrows. In some embodiments, cells collected using the microfilter may be used in downstream processes such as cell identification, enumeration, characterization, culturing, etc.

More specifically, in certain embodiments, multiple layers of epoxy-based photo-definable dry film may be exposed to energy simultaneously for scaled production of microfilters. In some embodiments, a stack of epoxy-based photo-definable dry film layers is provided, and all of the dry film layers in the stack are exposed to energy simultaneously. In some embodiments, a dry film structure including epoxy-based photo-definable dry film disposed on a substrate is provided in the form of a roll. In such embodiments, a portion of the structure may be unrolled for exposure of the dry film to energy. In certain embodiments, portions of a plurality of rolls may be exposed to energy simultaneously.

FIGS. 1A-1E are cross-sectional views illustrating multiple stages in a process for manufacturing a microfilter 120 in accordance with embodiments of the present invention. FIG. 2A is a flowchart illustrating a process 200 for manufacturing a microfilter in accordance with embodiments of the present invention. The exemplary process of FIG. 2A will be described below with reference to FIGS. 1A-1E. Other embodiments of the process illustrated in FIG. 2A will be described below with reference to FIGS. 3A-8B.

At block 220 of FIG. 2A, a layer of epoxy-based photo-definable dry film 100 (which may be referred to herein as "dry film 100") disposed on a substrate 180 is provided. In some embodiments, dry film 100 is laminated on substrate 180 at block 220. In certain embodiments, a silicon wafer is coated with a thin layer of metallic material, such as copper, and dry film 100 is laminated on the metallic material at block 220. In other embodiments, a dry film 100 with a substrate 180 already attached may be obtained and provided at block 220. As used herein, an "epoxy-based photo-definable" substance refers to a substance including or formed from a photo-definable epoxy resin, such as a polyfunctional epoxy resin, bisphenol A epoxy resin, epoxidized polyfunctional bisphenol A formaldehyde novolac resin, etc. Examples of photo-definable epoxy resins may be found in U.S. Pat. Nos. 7,449,280, 6,716,568, 6,391,523, and 6,558,868, the contents of which are hereby incorporated by reference herein. Examples of photo-definable epoxy resins may also be found in U.S. Patent Publication Nos. 2010/0068648 and 2010/0068649, the contents of which are hereby incorporated by reference herein. As used herein, an "epoxy-based photo-definable dry film" is a dry film including or formed from an epoxy-based photo-definable substance. Examples of epoxy-based photo-definable dry films that may be used in accordance with embodiments of the present invention may be found in U.S. Pat. Nos. 7,449,280, 6,391,523, and 6,558,868, and U.S. Patent Publication Nos. 2010/0068648 and 2010/0068649. Formulations of epoxy-based photo-definable dry films are not limit to those described here.

The liquid resist form of the epoxy-based photo-definable dry films before they are coated on substrate can be spin coated on substrate and dried to obtain the dry film on the substrate.

In certain embodiments, substrate 180 is a thin copper foil. In some embodiments, smooth substrates are preferable because irregularities in the surface of the substrate to which the dry film is laminated are transferred to a surface of the dry film. In some embodiments, a thin copper film is preferred as a substrate so that the substrate may be removed in a relatively short amount of time. In other embodiments, substrate 180 may be a silicon wafer, a polyimide film such as Kapton, or any other suitable material.

Figure 1B:
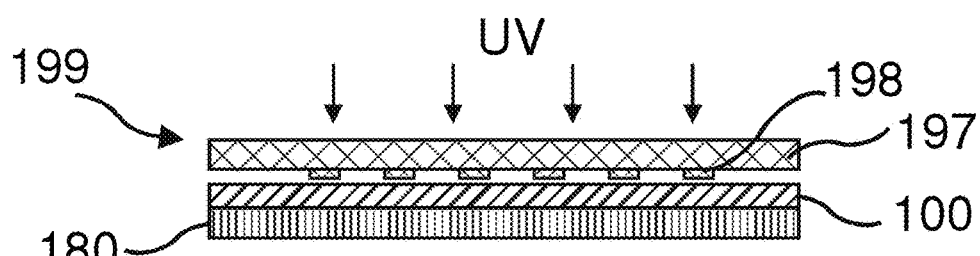
Figure 1C:
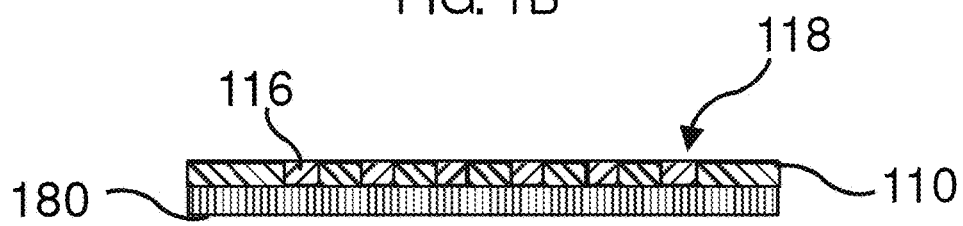
Figure 1D:
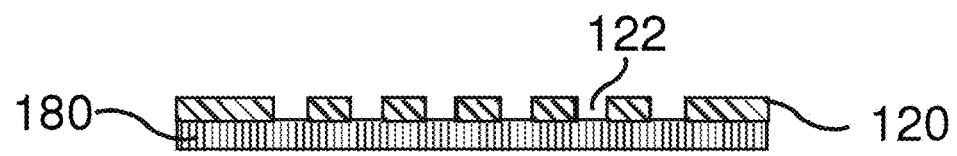

As shown in FIGS. 1B and 1C, dry film 100 is exposed to energy through a mask 199 to form an exposed dry film 110 at block 240. In the embodiment illustrated in FIGS. 1B and 1C, dry film 100 is exposed to energy in the form of ultraviolet (UV) light through an optical mask 199 having a mask portion 197 that is transparent to UV light and a mask pattern 198 formed from a thin film of material that is opaque to UV light. In alternative embodiments, dry film 100 may be exposed to X-rays through an X-ray mask at block 240, instead of being exposed to UV light through optical mask 199.

In the embodiment illustrated in FIGS. 1A-1E, epoxy-based photo definable dry film 100 is a negative resist. As used herein, a "negative resist" is a photo-definable substance that becomes polymerized when exposed to certain kinds of energy, such as UV light or X-rays. Examples of negative resist epoxy-based photo-definable dry films that may be used in accordance with embodiments of the present invention.

As shown in FIG. 1C, the portions of exposed dry film 110 that were exposed to UV light through mask 199 become polymerized, leaving portions 116 that are not polymerized. The polymerized and non-polymerized portions of exposed dry film 100 form a pattern 118 that is defined by optical mask 199. More particularly, pattern 118 of exposed dry film 110 is defined by a pattern 198 of optical mask 199, where pattern 198 is formed by material opaque to UV light. In certain embodiments, pattern 198 may be formed by a thin film of material opaque to UV light, such as a thin film of chromium.

In alternative embodiments, a positive epoxy-based photo-definable dry film may be used instead of a negative dry film. In such embodiments, the process for forming a microfilter from the positive dry film is similar to the process for forming a microfilter described in relation to FIGS. 1A-2A, except that a different mask may be used, as described below in relation to FIGS. 4A-4D. As used herein, a "positive resist" is a photo-definable substance in which polymeric bonds are broken when the substance is exposed to certain kinds of energy, such as UV light or X-rays. In certain embodiments, the positive resist may be a resist based on polydimethylglutarimide (such as PMGI, LOR available from MicroChem), an acetate and xylene free resist (such as an S1800® series resist available from Shipley Corp.), or another type of positive resist. For resist layers that are greater than a few microns in thickness, negative resists are generally much more sensitive than positive resists. Most polymer resists belong to the category of positive resist films. Examples of dry film positive resists that may be used include polymethylmethacrylate (PMMA), and a synthetic polymer of methyl methacrylate. Other examples of positive resists are acrylics, polyimide, polyesters, such as polyethylene terephthalate (PET) (MYLAR™), etc. In certain embodiments, a microfilter may be formed from a photo-definable dry film that is not epoxy based, in accordance with embodiments of the present invention. In such embodiments, the dry film may be a positive or a negative resist. In other embodiments, a microfilter may be formed from a photo-definable liquid resist, rather than a dry film. In such embodiments, the photo-definable liquid resist may be a positive resist or a negative resist. In certain embodiments, the photo-definable liquid resist may be liquid polyimide. In such embodiments, the photo-definable liquid polyimide may be positive resist or negative resist. The liquid resist is spin coated on the substrate and dried to form the dry film on the substrate.

At block 260, a microfilter 120 having a plurality of apertures 122 extending through the microfilter is formed from exposed dry film 110. In certain embodiments, microfilter 120 includes a polymer layer formed from epoxy-based photo-definable dry film and a plurality of apertures extending through the polymer layer. In each of the embodiments of the present invention described herein, a microfilter includes one or more polymer layers and one or more apertures extending though each of the one or more polymer layers. Also, as used herein, an "aperture" refers to any type of passage, pore, trench, gap, hole, etc., that extends between outer surfaces of a layer or other structure. In the embodiment illustrated in FIGS. 1A-1E, apertures 122 are pores 122.

Figure 1E:
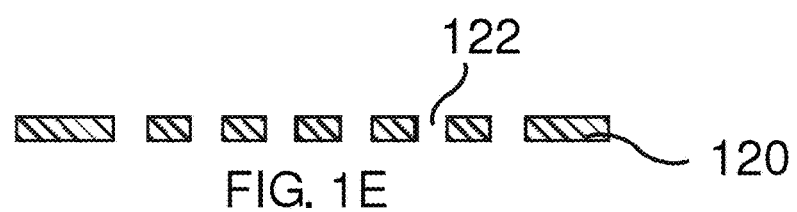

In the embodiment illustrated in FIGS. 1A-1E, exposed dry film 110 is developed to remove non-polymerized portions 116 to form microfilter 120 having pores 122. In certain embodiments, exposed dry film 110 is developed by applying a developer to dry film 110 to dissolve non-polymerized portions 116. In some embodiments, the developer is an aqueous solution that dissolves non-polymerized portions 116 when exposed dry film 110 is submerged in the developer. At block 280, microfilter 120 having pores 122 is removed from substrate 180 to form a free-standing microfilter 120, as shown in FIG. 1E. In some embodiments, a microfilter is a structure of one or more polymer layers including one or more apertures extending between outer surfaces of the structure, wherein the structure has sufficient strength and flexibility to filter a liquid passed through the one or more apertures. In certain embodiments, a microfilter may include apertures having dimensions small enough to prevent one or more types of bodily fluid cells from passing through the apertures when a bodily fluid or liquid containing a bodily fluid is passed through the filter, wherein the dimensions of the apertures are also small enough to prevent one or more other types of bodily fluid cells from passing through the filter. As used herein, "bodily fluid cell" refers to any cell that may be found in a bodily fluid of a patient, such as red or white blood cells, large rare cells, such as CTCs and fetal cells, circulating endothelial cells, etc. One can also obtain tumor cells from bone marrow after process to remove bone fragments and result in liquid form. In some embodiments, a microfilter includes apertures sized to allow passage of a significant number of red blood cells and to prevent passage of a significant number of CTCs. In certain embodiments, a microfilter formed from one or more layers of epoxy-based photo-definable dry film may be a polymeric microfilter.

Various embodiments of the process illustrated in FIG. 2A will be described below in relation to FIGS. 2B-8B. As noted above, in certain embodiments, substrate 180 may be copper foil. In such embodiments, copper substrate 180 may be removed from microfilter 120 using nitric acid, ferric chloride or another well-known reagent in one variation of block 280. In certain embodiments, the reagent may be used to etch away copper substrate 180 in order to remove it from microfilter 120. In other embodiments, substrate 180 may be another type of metallic foil, such as aluminum, and may be removed at block 280 by well-known methods.

FIG. 2B is a flowchart illustrating a process for forming a microfilter from an exposed dry film at block 260 of FIG. 2A in accordance with embodiments of the present invention. In certain embodiments, the process 260 for forming the microfilter comprises forming, from the exposed dry film, a polymer layer comprising a plurality of apertures. In the embodiment of FIG. 2B, a post bake process is performed on exposed dry film 110 disposed on substrate 180 at block 262. In certain embodiments, the post bake process includes exposing dry film 110 to a relatively high temperature to post bake dry film 110. At block 264, dry film 110 is developed by applying a developer to dry film 110, as described above in relation to FIGS. 1A-1E. At block 266, a hard bake process is performed on the developed dry film 110. In certain embodiments, the hard bake process includes exposing dry film 110 to a relatively high temperature. In some embodiments of the process illustrated in FIG. 2B, the hard bake process of block 266 may be omitted. In such embodiments, microfilter 120 is formed by post baking the exposed dry film 110 at block 262, and developing dry film 110 at block 264. The processes described above in relation to FIG. 2B may be used with any of the embodiments described herein. Additionally, in any of the embodiments of the present invention described here, the process for forming a polymer layer of a microfilter from an epoxy-based photo-definable dry film may include exposing the dry film to energy, performing a post-bake process, developing the exposed dry film, and/or post baking the exposed dry film, as described above.

FIGS. 3A-3E are cross-sectional views illustrating multiple stages in a process for manufacturing microfilter 120 in accordance with embodiments of the present invention. In the embodiment illustrated in FIGS. 3A-3E, the substrate is a polyimide film 181. At block 220, a layer of epoxy-based photo-definable dry film 100 disposed on polyimide film 181 is provided with a separator 182 disposed between a portion of dry film 100 and polyimide film 181. In the embodiment shown in FIG. 3A, a separator 182 is disposed between a portion of dry film 100 and polyimide film 181 along an edge of dry film 100. In certain embodiments, separator 182 may be disposed along one or more edges of dry film 100, or at other locations between dry film 100 and polyimide film 181. Separator 182 may be formed from a polyimide film (such as a KAPTON film) or from any other suitable material that can be laminated to dry film 100 and withstand the temperature of a hard bake process.

Figure 3A:
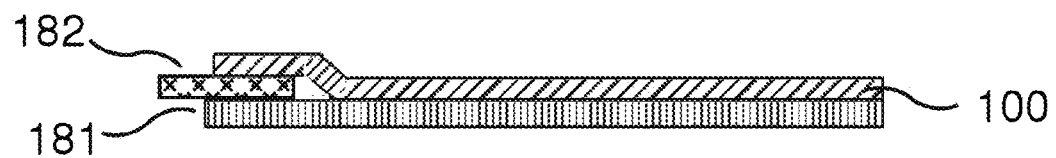
FIGS. 3A-3E are cross-sectional views illustrating multiple stages in a process for manufacturing a microfilter 120 in accordance with exemplary embodiments of the present invention.
Figure 3B:
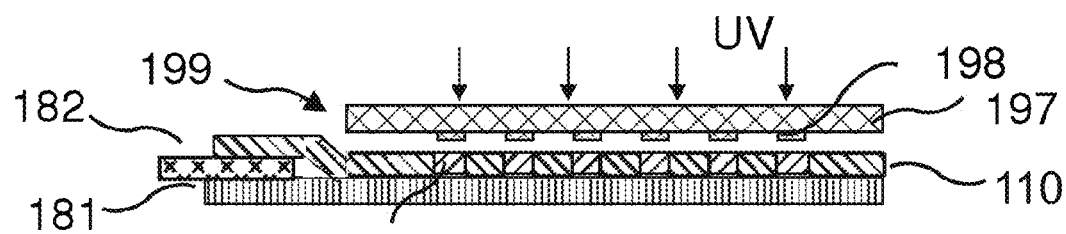
Figure 3C:
Figure 3D:
Figure 3E:

As shown in FIGS. 3B-3C, dry film 100 is exposed to energy, and a microfilter 120 is formed from exposed dry film 110 at blocks 240 and 260, as described above in relation to FIGS. 1B-1D. In certain embodiments, microfilter 120 includes a polymer layer comprising a plurality of apertures there through. In the embodiment illustrated in FIGS. 3A-3E, microfilter 120 is removed from polyimide film 181 by grasping an exposed end of separator 182 and using separator 182 to peel microfilter 120 from polyimide film 181. After dry film 100 is removed from polyimide layer 181, as shown in FIG. 3D, separator 182 is removed from dry film 100 to obtain a free-standing microfilter 120, as shown in FIG. 3E. Removing microfilter 120 from layer 181, and removing separator 182 from microfilter 120, are two steps performed in one variation of block 280, in accordance with embodiments of the present invention.

In alternative embodiments of the process illustrated in FIG. 2A, a liquid resist may be used instead of dry film 100. In such embodiments, a substrate is coated with a thin layer of a metallic substance and an epoxy-based liquid photoresist is spin coated onto the metallic substance to provide a layer of an epoxy-based photo-definable substance on a substrate, in one variation of block 210. In certain embodiments, the substrate may be a silicon wafer, the metallic substance may be copper, and the liquid photoresist may be an epoxy-based photo-definable liquid. In some embodiments, the epoxy-based photo-definable liquid is a liquid negative resist, such as SU-8. The layer of the epoxy-based photo-definable substance is exposed to energy, and a microfilter 120 is formed from the exposed layer at blocks 240 and 260, as described above in relation to FIGS. 1B-1D. In one variation of block 280, microfilter 120 is released from the substrate by etching away the metallic substance via conventional processes as described above. In certain embodiments, the liquid resist may be a liquid negative resist, such as SU-8 or KMPR® available from MicroChem Corp.

In other alternative embodiments of the process illustrated in FIG. 2A, a liquid negative resist may be used instead of dry film 100, and a positive resist between the negative resist and the substrate may be used as a release layer. In such embodiments, to provide a layer of an epoxy-based photo-definable substance on a substrate in one variation of block 210, a liquid positive resist is spin coated on a substrate, the positive resist is exposed to energy (such as UV light) at the appropriate dose for the thickness of the coating, and a liquid, epoxy-based negative resist is spin coated on the positive resist. In certain embodiments, the positive resist may be exposed to energy without the use of a mask. The layer of the epoxy-based photo-definable substance is exposed to energy, and a microfilter 120 is formed from the exposed layer at blocks 240 and 260, as described above in relation to FIGS. 1B-1D. In such embodiments, in one variation of block 280, microfilter 120 is released from the substrate by developing the positive resist. In certain embodiments, the same developer may be used to develop both the positive and the negative resists. In other embodiments, one developer may be used to form the pores in microfilter 120, and another developer may be used to release the microfilter from the substrate. In alternative embodiments, a dry film positive resist may be used as the release layer instead of a liquid positive resist. Examples of dry film positive resists that may be used include polymethylmethacrylate (PMMA), and a synthetic polymer of methyl methacrylate.

In other embodiments, a negative epoxy-based photo-definable dry film 100 may be used in combination with a positive resist release layer. Such embodiments are similar to the embodiments described above utilizing a positive resist release layer, except that a layer of the negative dry film 100 may be laminated on the spin coated positive resist at block 210, rather than spin coating a liquid negative resist.

Figure 4A:
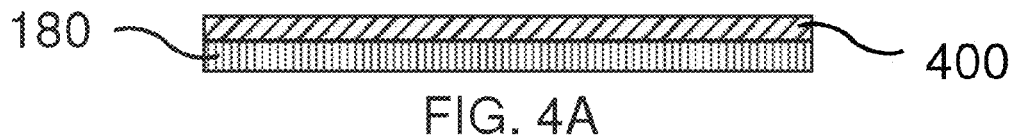
FIGS. 4A-4D are cross-sectional views illustrating multiple stages in a process for manufacturing a microfilter in accordance with exemplary embodiments of the present invention.
Figure 4B:
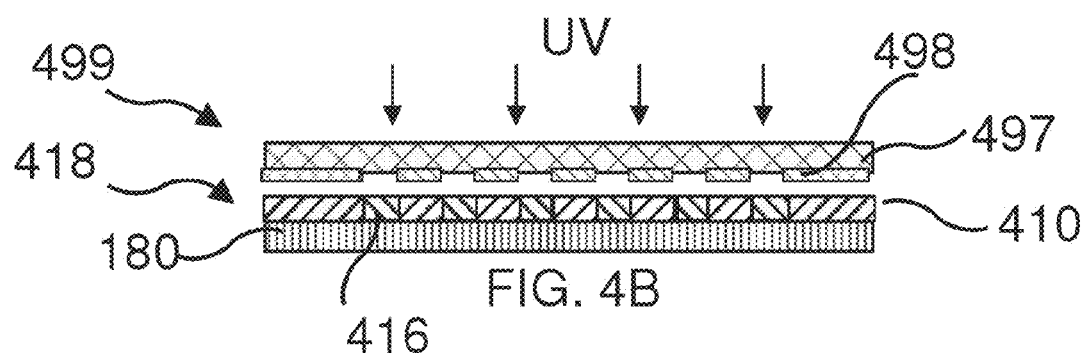
Figure 4C:
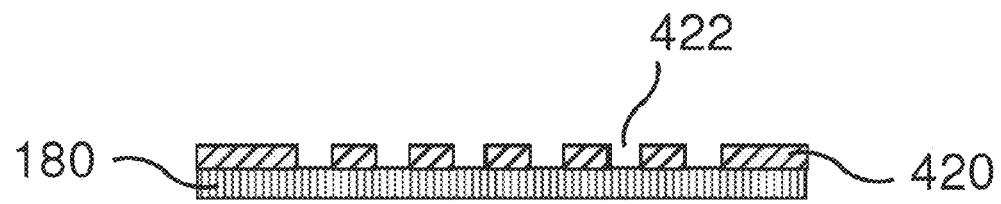

FIGS. 4A-4D are cross-sectional views illustrating multiple stages in a process for manufacturing a microfilter 420 in accordance with embodiments of the present invention. In the embodiment illustrated in FIGS. 4A-4D, a layer of positive, epoxy-based photo-definable dry film 400 (which may be referred to herein as "dry film 400") disposed on substrate 180 is provided at block 220. In certain embodiments, positive dry film 400 is laminated on substrate 180 at block 220. As shown in FIG. 4B, positive dry film 400 is exposed to energy at block 240, as described above in relation to FIGS. 1B and 1C, except that, rather than exposed portions of dry film 400 becoming polymerized, polymeric bonds of dry film 400 are broken at portions 416, which are exposed to energy (e.g., UV light) through mask 499. A pattern 418 of exposed portions 416 and unexposed portions is formed in exposed dry film 410. As shown in FIG. 4B, mask 499 includes a transparent portion 497 and an opaque portion 498. As described above, mask 199 of FIG. 1B is used with a negative resist and is configured to cover portions of dry film 100 where pores will be formed in dry film 100. In the embodiment illustrated in FIGS. 4A-4D, opaque portions 498 of mask 499 are configured to cover all portions of positive dry film 400 except the locations where apertures will be formed, allowing UV light to pass through mask 499 to positive dry film 400 at locations where apertures are to be formed in positive dry film 400.

Figure 4D:
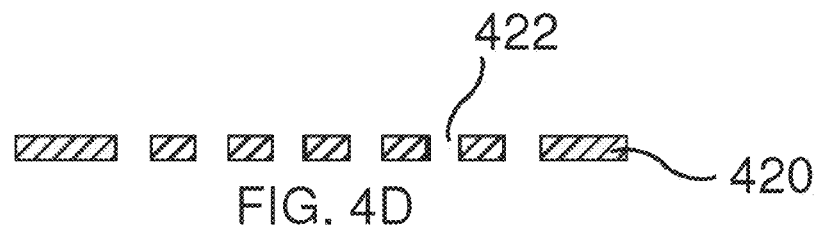

In the embodiment illustrated in FIGS. 4A-4D, a microfilter 420 is formed from exposed dry film 410 in one variation of block 260, by developing dry film 410 using a developer that dissolves the portions 416 of dry film 400 where the polymeric bonds were broken. At block 280, microfilter 420 having apertures 422 is removed from substrate 180 to form a free-standing polymeric microfilter 420, as shown in FIG. 4D. In some embodiments, microfilter 420 includes a polymer layer formed from epoxy-based photo-definable dry film and includes a plurality of apertures extending through the polymer layer. In certain embodiments, the apertures 422 are pores 422. In some embodiments, at block 280, microfilter 420 may be released from the substrate by developing the positive resist, as described above.

FIGS. 5A-5D are cross-sectional views illustrating multiple stages in a process for manufacturing a plurality of microfilters from a plurality of layers of epoxy-based photo-definable dry film in accordance with embodiments of the present invention. In certain embodiments of the process illustrated in FIG. 2A, a plurality of dry film structures 501, each including a layer of epoxy-based photo-definable dry film 500 (which may be referred to herein as "dry film 500") disposed on a substrate 580, are provided at block 220. In the embodiment illustrated in FIGS. 5A-5D, dry films 500 disposed on substrates 580 are provided at block 220 by stacking structures 501 on a support 590, as illustrated in FIG. 5A.

In certain embodiments, as illustrated in FIG. 5A, dry films 500 in the stack of structures 501 are simultaneously exposed to energy in the form of X-rays through an X-ray mask 599 at block 240 of FIG. 2A. In some embodiments, the penetration of X-rays is much deeper than UV light. Unlike UV light, X-rays do not diverge within a material having a thickness of less than 5 mm, even for features significantly smaller than one micron. In some embodiments, X-ray lithography may be typically performed on a beamline of a synchrotron. In addition, X-ray lithography can be used for both negative and positive resists. In the embodiment illustrated in FIGS. 5A-5D, dry films 500 are each negative resists. In other embodiments, dry films 500 may be positive resists. In such embodiments, a mask configured to form apertures in a positive resist, as described above in relation to mask 499 of FIG. 4B, may be used. Additionally, in embodiments in which dry films 500 are positive resists, dry films 500 may be may be attached to support 290 and stacked directly on one another, without each being disposed on a respective substrate.

As shown in FIG. 5B, the portions of each dry film 500 exposed to X-rays through mask 599 become polymerized, leaving portions 516 of dry film 500 that are not polymerized. The polymerized and non-polymerized portions of each dry film 500 form a pattern 518 that is defined by pattern 598 of optical mask 599. In some embodiments, mask 599 includes an X-ray transparent portion 597, and a pattern 598 configured to substantially block X-rays. In certain embodiments, pattern 598 is formed from gold. In addition, in some embodiments, X-ray transparent portion 597 may be a thin graphite sheet or a silicon wafer. In the embodiment illustrated in FIGS. 5A-5D, each of substrates 580 transmits most of the X-ray energy applied to it. In certain embodiments, substrates 580 are formed from a metallic foil. In such embodiments, when the foil is sufficiently thin, each substrate 580 will transmit most of the X-ray energy applied to it. In some embodiments, the number of structures 501 that may be stacked and then exposed simultaneously is based on the reduction in the dose of the X-rays caused by the X-rays passing through the metallic foil.

In certain embodiments, in one variation of block 260, the plurality of exposed dry films 510 are developed to form a plurality of microfilters 520 each having apertures 522 in a manner similar to that described above in relation to FIGS. 1A-1E. In certain embodiments, apertures 522 are pores 522. In some embodiments, the process illustrated in FIGS. 5B and 5C may be performed in one variation of block 260. In such embodiments, structures 501 are separated from one another, as shown in FIG. 5B, and a post bake procedure is performed on exposed dry films 510 disposed on respective substrates 580 in one variation of block 262. In certain embodiments, each of exposed dry films 510 is developed, as described above, in one variation of block 264 to form pores 522 in each of dry films 500, as shown in FIG. 5C. In some embodiments, a hard bake procedure is performed on dry films 510 disposed on respective substrates 580, in one variation of block 266, to form microfilters 520 having pores 522. In other embodiments, the hard bake procedure may be omitted. In certain embodiments, in one variation of block 280, substrates 580 are chemically removed from microfilters 520, as described above, to obtain free-standing microfilters 520 having pores 522, as shown in FIG. 5D. In certain embodiments, each of microfilters 520 is a polymer layer including apertures 522.

As described above, in certain embodiments, each of substrates 580 may be formed from a metallic foil. In alternative embodiments, substrate 580 may be a polymer based substrate that transmits most of the X-rays applied to it, and which has a melting point higher than a post bake temperature for dry film 500. For example, in certain embodiments, substrate 580 may be formed from a positive resist. In such embodiments, substrate 580 may be exposed to energy, such as UV light or X-rays, sufficient to break polymeric bonds in the positive resist such that substrate 580 may be removed chemically by a developer solution at block 280 of FIG. 2A. In other embodiments, substrate 580 may be a polyimide film and may be removed at block 280 by peeling the polyimide substrate 580 from microfilter 520.

In alternative embodiments, layers of epoxy-based photo-definable dry film 500 (which may be referred to as "dry films 500") may be stacked and simultaneously exposed without each of the layers being disposed on a respective substrate. In such embodiments, in one variation of block 220, dry films 500 are stacked on a support 590 without substrates disposed between adjacent dry films 500. The stacked dry films 500 are exposed in one variation of block 240. In some embodiments, the process illustrated in FIG. 2B may be performed at block 260. In such embodiments, the exposed dry films 510 may be separated and placed on separate substrates on which exposed dry films 510 undergo a post bake process in one variation of block 262. In such embodiments, the substrates used are able to withstand the post bake temperature and can be dissolved by water or one or more chemicals. While attached to respective substrates, exposed dry films 510 are developed at block 264 and may undergo a hard bake procedure at block 266. At block 280, the substrates 580 are removed from the microfilters 520 formed from exposed dry films 510.

Figure 6A:
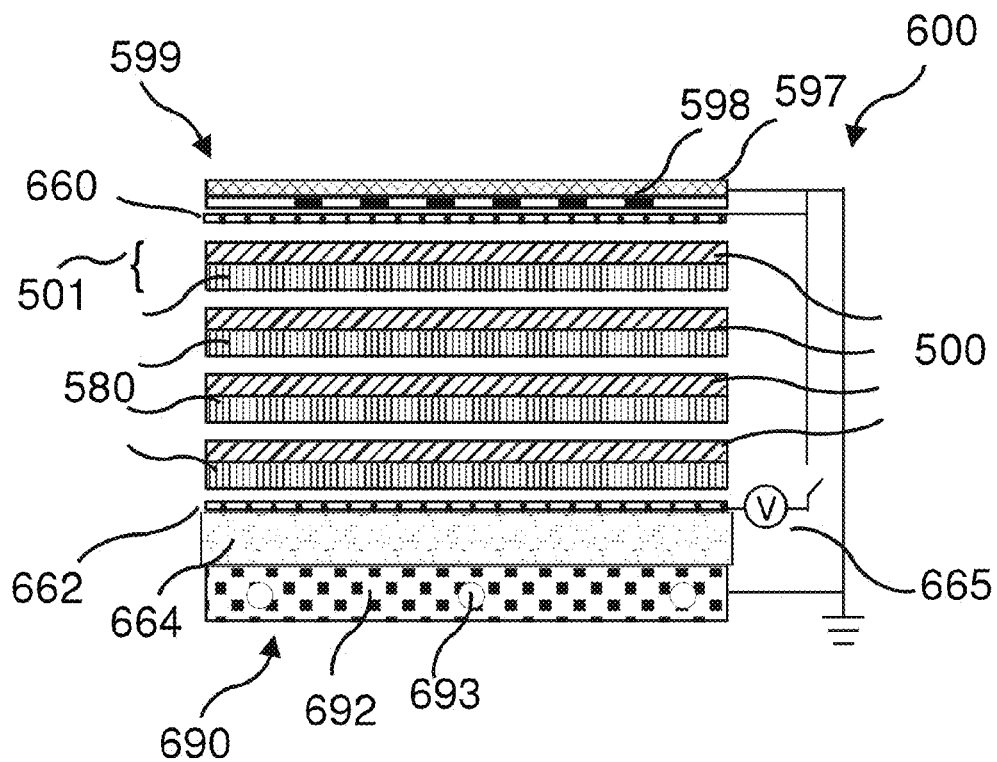
FIGS. 6A and 6B are cross-sectional views illustrating multiple stages in a process for attaching dry film structures to a support using an electrostatic chuck apparatus in a process for forming microfilters in accordance with exemplary embodiments of the present invention.
Figure 6B:
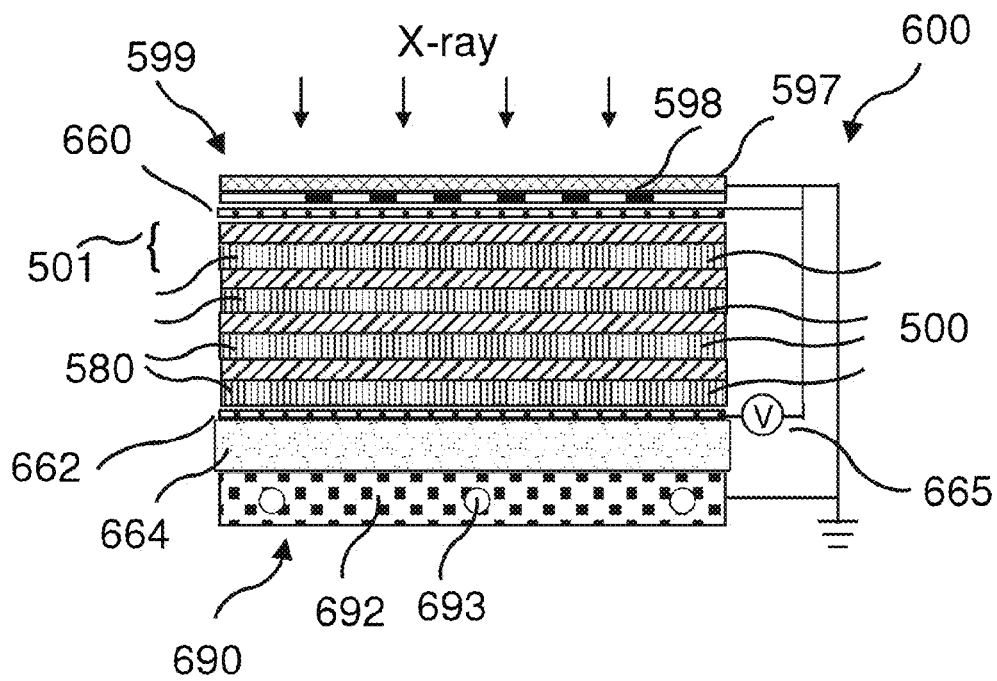

In certain embodiments, structures 501 may be attached to support 590 using adhesive, a clamp, or any other suitable mechanism or method. In some embodiments, structures 501 are held to a support by an electrostatic chuck. FIGS. 6A and 6B are cross-sectional views illustrating multiple stages in a process for attaching dry film structures 501 to a support using an electrostatic chuck apparatus 600 in a process for forming microfilters in accordance with embodiments of the present invention. In the embodiment illustrated in FIGS. 6A and 6B, a plurality of dry film structures 501, each including a layer of epoxy-based photo-definable dry film 500 disposed on a substrate 580, are provided stacked on a support 690, as shown in FIG. 6A. As shown in FIG. 6A, support 690 includes a water cooling frame 692 with a duct 693, an insulator 664 disposed on frame 692, and a conductive layer 662 disposed on insulator 664. Additionally, a transparent conductive layer 660 is placed on the stack of structures 501 such that the stack of structures 501 is disposed between conductive layers 660 and 662, as shown in FIG. 6A. Also as shown in FIG. 6A, a circuit connecting the conductive layers is open so that a voltage 665 of zero is applied to the conductive layers.

As shown in FIG. 6B, closing the circuit between the conductive layers and applying a non-zero voltage 665 between conductive layers 660 and 662 causes apparatus 600 to press together structures 501 between conductive layers 660 and 662. With structures 501 pressed together by apparatus 600, X-rays may be applied to dry films 500 through X-ray mask 599, as described above in relation to FIGS. 5A-5D. In certain embodiments, stacking structures 501 on apparatus 600 and pressing together structures 501 using apparatus 600, as described above in relation to FIGS. 6A and 6B, may be performed in one variation of block 220 of FIG. 2A. While the use of an electrostatic chuck apparatus has been described above in relation to forming microfilters from dry films each disposed on a respective substrate, in alternative embodiments, an electrostatic chuck may similarly be used to press together a stack of free standing polymeric films, such as free standing dry films, that are not each attached to a respective substrate. Such free standing dry films may be stacked and pressed together during a process for forming a plurality of microfilters from the plurality of dry films.

Figure 7A:
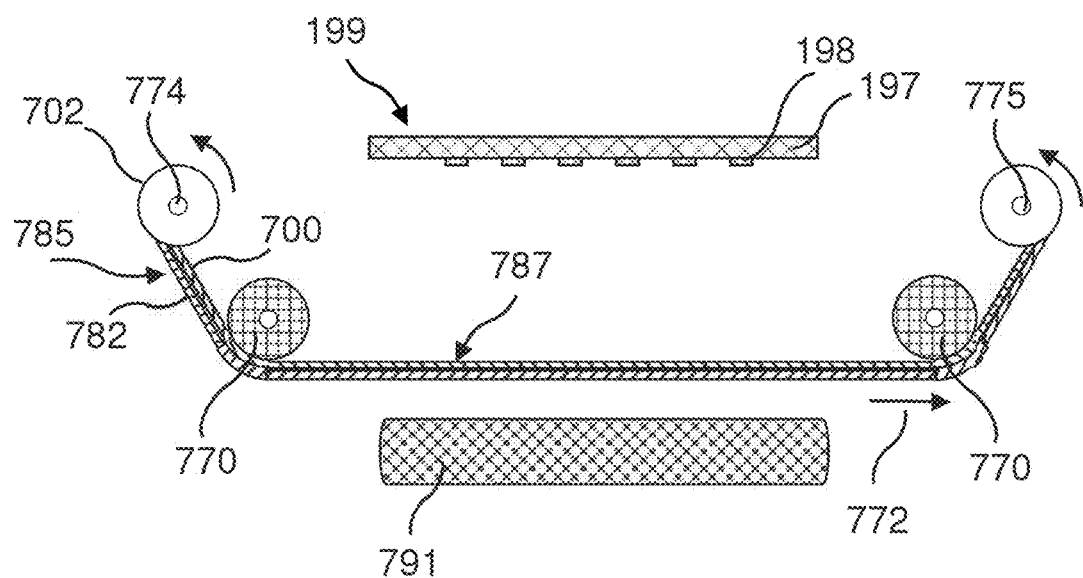
FIGS. 7A and 7B are cross-sectional views illustrating multiple stages in a process for manufacturing microfilters from a roll of a dry film structure in accordance with exemplary embodiments of the present invention.
Figure 7B:
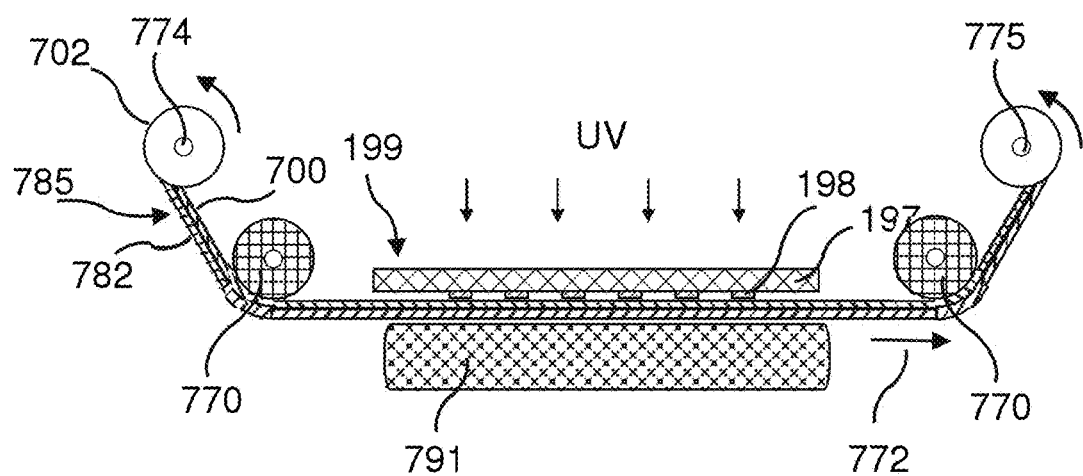

FIGS. 7A and 7B are cross-sectional views illustrating multiple stages in a process for manufacturing microfilters from a roll of a dry film structure in accordance with embodiments of the present invention. In the embodiment illustrated in FIGS. 7A and 7B, a dry film structure 785 is provided in the form of a roll 702 of the dry film structure 785. Dry film structure 785 includes a layer of epoxy-based photo-definable dry film 700 (which may be referred to herein as "dry film 700") disposed on a removable substrate 782. In some embodiments, substrate 782 may be a chemically dissolvable metallic foil. In certain embodiments, the metallic foil may include aluminum or copper, which may be etched away as described above. In the embodiment illustrated in FIGS. 7A and 7B, a portion of roll 702 is disposed on a roller 774 and another portion is disposed on a roller 775. A working portion 787 of dry film structure 785 extends between rollers 774 and 775 and is held substantially flat by rollers 770 for exposure to energy through mask 199.

In certain embodiments of the process illustrated in FIG. 2A, a layer of epoxy-based photo-definable dry film 700 disposed on a substrate 782 is provided, in one variation of block 220, by unrolling a portion of dry film structure 785 from roll 702 and advancing the portion of structure 785 in the direction of arrow 772 to provide working portion 787 of structure 785 between support 791 and mask 199. In some embodiments, the working portion 787 provided at block 220 includes a portion of dry film 700 that has not been patterned by exposure to energy through a mask. In certain embodiments, support 791 and mask 199 are moved away from structure 785 when structure 785 is advanced.

In the embodiment illustrated in FIGS. 7A and 7B, mask 199 and support 791 are moved adjacent to structure 785, and dry film 700 is exposed to energy through mask 199, as shown in FIG. 7B, in one variation of block 240 of FIG. 2A. In the embodiment shown in FIGS. 7A and 7B, mask 199 is an optical mask and the energy is UV light, although a different type of energy may be used along with a different mask, as described above. In the embodiment illustrated in FIGS. 7A and 7B, dry film 700 is a negative resist. In other embodiments, dry film 700 may be a positive resist. In such embodiments, a mask configured to form pores in a positive resist, as described above in relation to mask 499 of FIG. 4B, may be used. Exposing dry film 700 to energy through the mask forms a pattern in dry film 700, as described above in relation to other embodiments. In certain embodiments, support 791 presses against structure 785, as shown in FIG. 7B, to stretch dry film 700 for the exposure process to thereby provide additional tension and stability to dry film 700 during the exposure process. In some embodiments, after exposing dry film 700, structure 785 may be advanced again as described above, to provide a new working portion 787 that has not yet been exposed at block 220, and the new working portion 787 may be exposed at block 240, as described above. In certain embodiments, this process of advancing structure 785 and exposing dry film 700 may be continuously repeated. In some embodiments, the process may be repeated until most or all portions of dry film 700 have undergone an exposure process.

In some embodiments, a microfilter having apertures is formed from an exposed portion of dry film 700 by developing the exposed portion, as described above in relation to other embodiments, in one variation of block 260. In such embodiments, the exposed portion of dry film 700 may be developed before it is rolled onto roller 775, or may be developed after all desired portions of dry film 700 have been exposed. In some embodiments, the process illustrated in FIG. 2B may be performed at block 260. In such embodiments, the exposed portion of dry film 700 may be advanced through an oven for a post bake procedure at block 262, the exposed portion of dry film 700 may be developed at block 264, and then undergo a hard bake procedure at block 266. In other embodiments, the procedures at blocks 262, 264 and 266 may be performed after all desired portions of dry film 700 have been exposed. In certain embodiments, the hard bake procedure may be omitted.

In some embodiments, after developing the exposed dry film 700, substrate 782 is removed at block 280, as described above in relation to other embodiments. In certain embodiments, after removing substrate 782, individual microfilters are diced from the roll of dry film from which the microfilters were formed. In certain embodiments, forming microfilters from a dry film provided as a roll may simplify the manufacture of microfilters in accordance with embodiments of the present invention, and may allow automation of the manufacturing process.

Figure 8A:
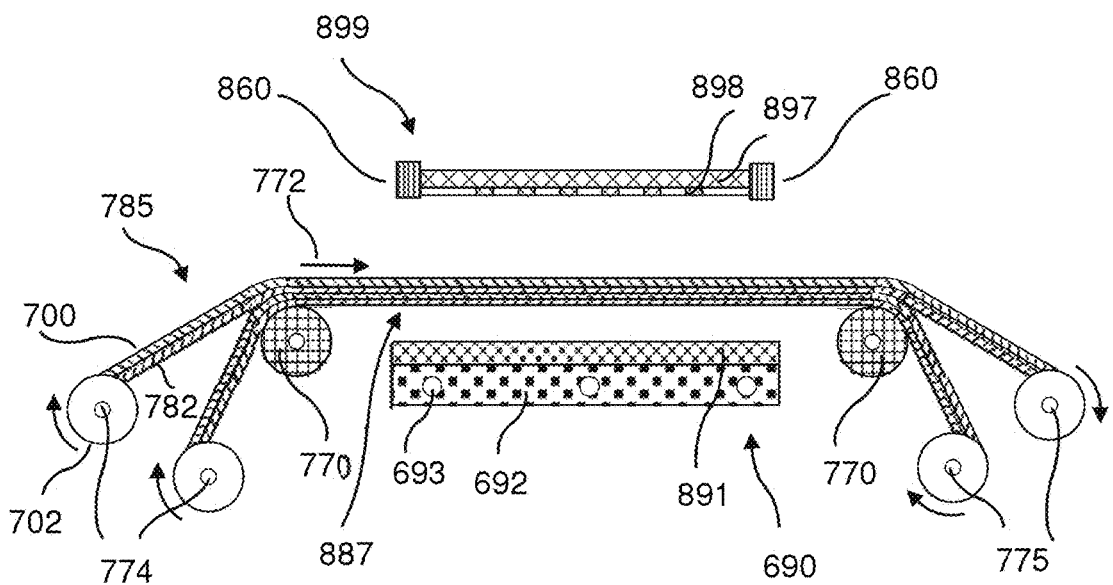
FIGS. 8A and 8B are cross-sectional views illustrating multiple stages in a process for manufacturing microfilters from a plurality of rolls of dry film structures in accordance with exemplary embodiments of the present invention.
Figure 8B:
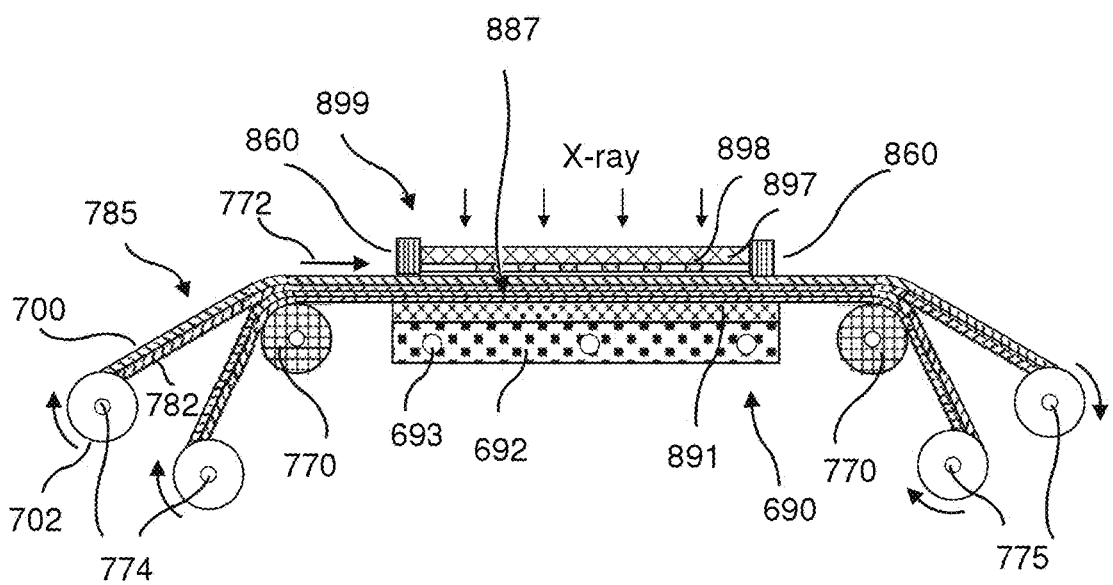

FIGS. 8A and 8B are cross-sectional views illustrating multiple stages in a process for manufacturing microfilters from a plurality of rolls of dry film structures in accordance with embodiments of the present invention. The embodiment illustrated in FIGS. 8A and 8B is similar to the embodiment illustrated in FIGS. 7A and 7B, except that layers of epoxy-based photo-definable dry film 700 of multiple rolls 702 are exposed to energy simultaneously. In such embodiments, a plurality of layers of epoxy-based photo-definable dry film 700 each disposed on a respective substrate 782 are provided, in one variation of block 220, by advancing the structure 785 of each roll 702 in the direction of arrow 772 to provide a stack 887 of structures 785 between support 891 and mask 899. In the embodiment illustrated in FIGS. 8A and 8B, mask 899 and support 891 are moved adjacent to the stack 887, and the portions of dry films 700 in stack 887 disposed between mask 899 and support 891 are exposed to energy simultaneously through mask 899, as shown in FIG. 8B, in one variation of block 240 of FIG. 2A. In the embodiment illustrated in FIGS. 8A and 8B, dry films 700 are each negative resists. In other embodiments, dry films 700 may be positive resists. In such embodiments, a mask configured to form apertures in a positive resist, as described above in relation to mask 499 of FIG. 4B, may be used. Further processes for forming microfilters from dry films 700 are similar to the processes described above in relation to the embodiment illustrated in FIGS. 7A and 7B.

In the embodiment illustrated in FIGS. 8A and 8B, support 891 is disposed on a water cooling frame 692 including a duct 693. In addition, as shown in FIG. 8B, working portions 887 of structure 785 may be securely held in place between support 891 and mask 899 by a clamp 860. In alternative embodiments, stack 887 may be held secure using an electrostatic chuck, as described above in relation to other embodiments. In some embodiments, the number of dry films 700 exposed simultaneously may be determined based on the precision yielded when exposing a stack of a particular number of films. In certain embodiments, forming microfilters from a plurality of dry films provided as a plurality of rolls, as described above, may simplify the manufacture of microfilters and/or facilitate high volume production of microfilters.

In embodiments in which non-epoxy-based dry films are used, the dry films may be provided in roll form without a substrate. In such embodiments, each roll 702 includes only the dry film and not any substrate. In embodiments in which epoxy-based dry films are used, each roll 702 may include an additional cover layer on dry film 700. In such embodiments, substrate 782 is disposed on a first side of dry film 700 and the cover layer on the opposite side of dry film 700. In certain embodiments, lithography-based microfabrication in accordance with embodiments of the present invention may enable efficient mass production of highly uniform precision microfilters. In certain embodiments, fabricating microfilters in accordance with embodiments of the present invention may yield increased porosity and pore uniformity in the microfilters produced.

FIGS. 9A-9D are partial top views illustrating various microfilters aperture distributions in accordance with embodiments of the present invention. In certain embodiments, microfilters having different aperture sizes, shapes and distributions may be provided. In some embodiments, certain combinations of aperture size, shape and distribution may be more advantageous than others for a particular application of a microfilter. For example, for the microfiltration of rare cells, such as circulating tumor cells and fetal cells in blood, a microfilter having round pores each having a diameter of 7-8 microns may be preferable in certain embodiments. In some applications, a microfilter having round pores each with a diameter of 7-8 microns can trap the rare cells while retaining a very small percentage of blood cells.

Figure 9A:
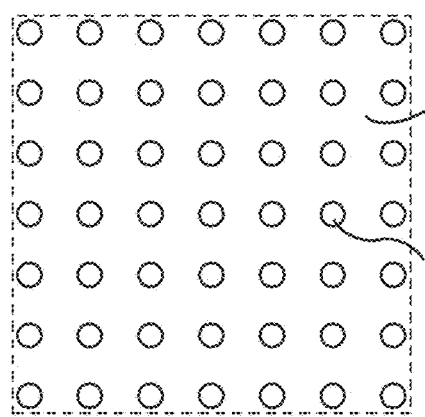
FIGS. 9A-9D are partial top views illustrating various microfilters aperture distributions in accordance with exemplary embodiments of the present invention.
Figure 9B:
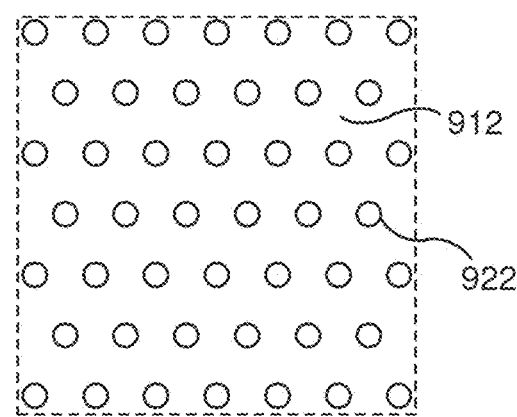
Figure 9C:
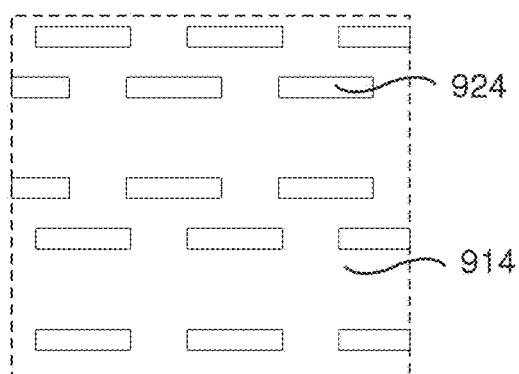
Figure 9D:
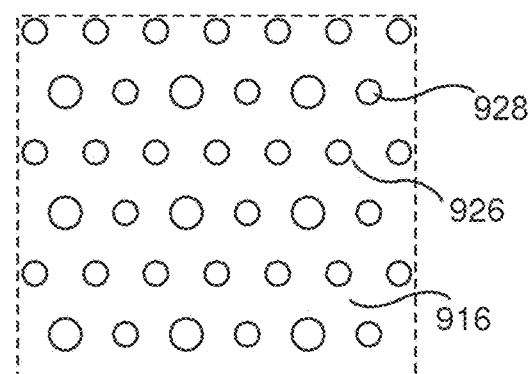

In the embodiments illustrated in FIGS. 9A and 9B, microfilters 910 and 912 each have a uniform distribution of pores 920 and 922, respectively. Additionally, pores 920 are uniform in size, as are pores 922. In the embodiment illustrated in FIG. 9C, microfilter 914 includes uniform rectangular pores 924, distributed over microfilter 914 in several groupings of pores 924. In the embodiment illustrated in FIG. 9D, microfilter 916 a plurality of pores 926 of a first size, and a plurality of pores 928 of a second size. In other embodiments, any or pores 920, 922, 924, 926 and 928 may be any other type of aperture. Any of microfilters 910, 912, 914 and 916 may be manufactured using any of the microfilter manufacturing processes described above in accordance with embodiments of the present invention. Additionally, any of the microfilter manufacturing processes described above in accordance with embodiments of the present invention may be used to form apertures of a plurality of different cross-sectional shapes. For example, in certain embodiments, apertures may be formed which have the cross-sectional shape of a circle, triangle, square, rectangle, ellipse, oval, trapezoid, parallelogram, etc.

Figure 10A:
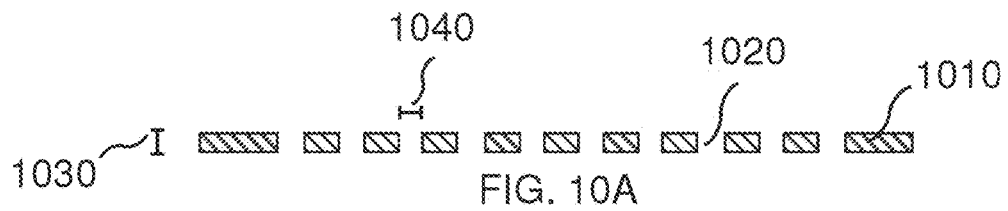
FIGS. 10A-10E are cross-sectional views illustrating microfilters having various thicknesses and various aperture shapes, sizes and distributions in accordance with exemplary embodiments of the present invention.
Figure 10B:
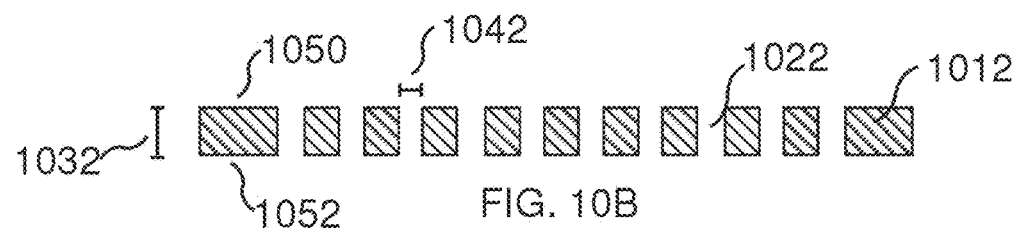
Figure 10C:
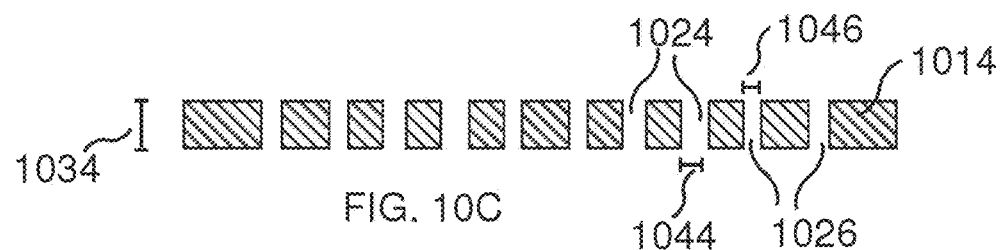

Microfilters having various thicknesses and various aperture shapes, sizes and distributions may be manufactured in accordance with embodiments of the present invention described herein. FIGS. 10A-10E are cross-sectional views illustrating microfilters having various thicknesses and various aperture shapes, sizes and distributions in accordance with embodiments of the present invention. FIGS. 10A and 10B show microfilters 1010 and 1012, each formed via one of the processes described above in accordance with embodiments of the present invention. Microfilter 1010 includes a plurality of pores 1020, each having a width 1040. Microfilter has a thickness 1030 substantially perpendicular to the width 1040 of pores 1020. In the embodiment illustrated in FIG. 10A, thickness 1030 is not significantly larger than width 1040. In certain embodiments, it is preferable that the thickness of the microfilter is on the same order as the width of one or more pores of the microfilter in order to reduce the pressure required to pass a liquid sample through the pores. In some applications, if the thickness of a microfilter is significantly greater than the width of some or all of the pores, a much larger amount of pressure may be applied to the microfilter to pass a liquid sample through a microfilter than if the microfilter has a thickness on the same order as some or all of the pores. Passing the liquid sample through the filter with a relatively large amount of pressure may distort the shape of one or more pores, or risk breaking the microfilter.

For example, for the microfiltration of rare cells, such as CTCs and fetal cells in blood, a microfilter having a thickness of 8-14 microns may be preferable in certain embodiments. In certain embodiments, a microfilter for such an application may have pores each having a diameter of 7-8 microns and a thickness of 8-14 microns. In other embodiments, a microfilter for such applications may include a rectangular aperture having a width of between 5-7 microns and a length greater than 7 microns, wherein the length and width of the aperture are both substantially perpendicular to the thickness of the microfilter. In certain embodiments, the rectangular aperture may be an elongate trench. In certain embodiments, it may be preferred that the width of the apertures in the microfilter are near in size to the thickness of the microfilter. In some embodiments, the thickness of the microfilter is less than ten times the width of some or all the pores. In other embodiments, the thickness of the microfilter is within 10 microns of the width of some or all of the pores. Microfilters formed in accordance with embodiments of the present invention may be used in applications other than capturing circulating tumor cells from blood. In some embodiments, the desired aperture geometry, aperture dimensions, aperture distribution, microfilter materials, microfilter thickness, microfilter size, etc., may vary for different applications. In some embodiments, desired aperture geometry, dimensions, and distribution may be provided by using an appropriate mask, such as an optical or X-ray mask. In certain embodiments, a consideration for microfilters is strength of the material from which the microfilter is made to prevent breakage of the filter material or distortion of the aperture shape.

Figure 10D:
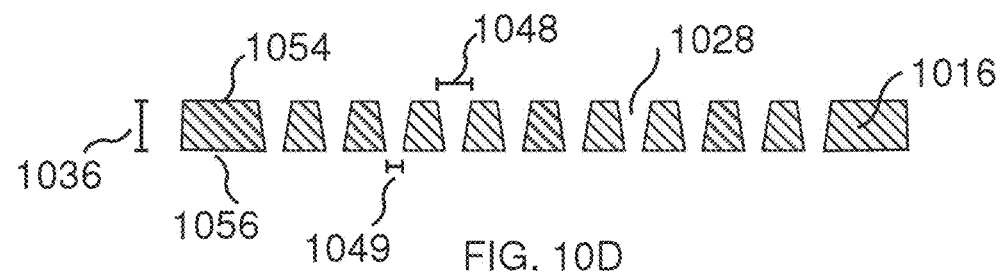
Figure 10E:
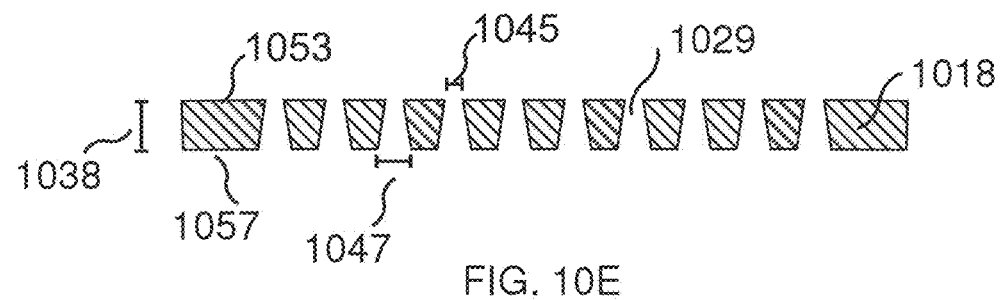

As shown in FIG. 10B, microfilter 1012 has a plurality of pores 1022 each having a width 1042. Microfilter 1012 also has a thickness 1032 that is substantially perpendicular to the width 1042 of pores 1022. The thickness 1032 of microfilter 1012 is greater than the thickness of microfilter 1010. In the embodiment illustrated in FIG. 10B, pores 1022 are uniform in size and are each substantially perpendicular to a first surface 1050 and a second surface 1052 of microfilter 1012. In the embodiment illustrated in FIG. 10C, microfilter 1014 has pores 1024 with a first width 1044 and pores 1026 with a second width 1046 that is smaller than the first width 1044. Microfilter 1014 also has a thickness 1034. In the embodiment illustrated in FIG. 10D, microfilter 1016 has pores 1028 with non-uniform cross-sectional shapes. Each pore 1028 has a first opening in a first surface 1054 of microfilter 1016 and a second opening in a second surface 1056 of microfilter 1016. As shown in FIG. 10D, the width 1048 of pore 1028 at the first surface 1054 is greater than the width 1049 of pore 1028 at the second surface 1056. Microfilter 1016 also has a thickness 1036. In the embodiment illustrated in FIG. 10E, microfilter 1018 has pores 1029 with non-uniform cross-sectional shapes. Each pore 1029 has a first opening 1045 in a first surface 1053 of microfilter 1018 and a second opening 1047 in a second surface 1057 of microfilter 1018. As shown in FIG. 10E, the width 1045 of pore 1029 at the first surface 1053 is smaller than the width 1047 of pore 1029 at the second surface 1057. Microfilter 1018 also has a thickness 1038.

Figure 12A:
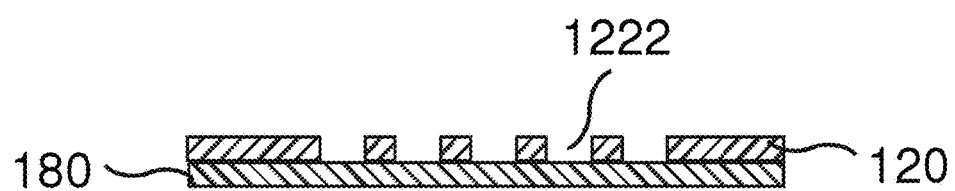
FIGS. 12A-12K are cross-sectional views illustrating multiple stages in a process for manufacturing a multi-layer microfilter in accordance with exemplary embodiments of the present invention.
Figure 12B:
Figure 13A:
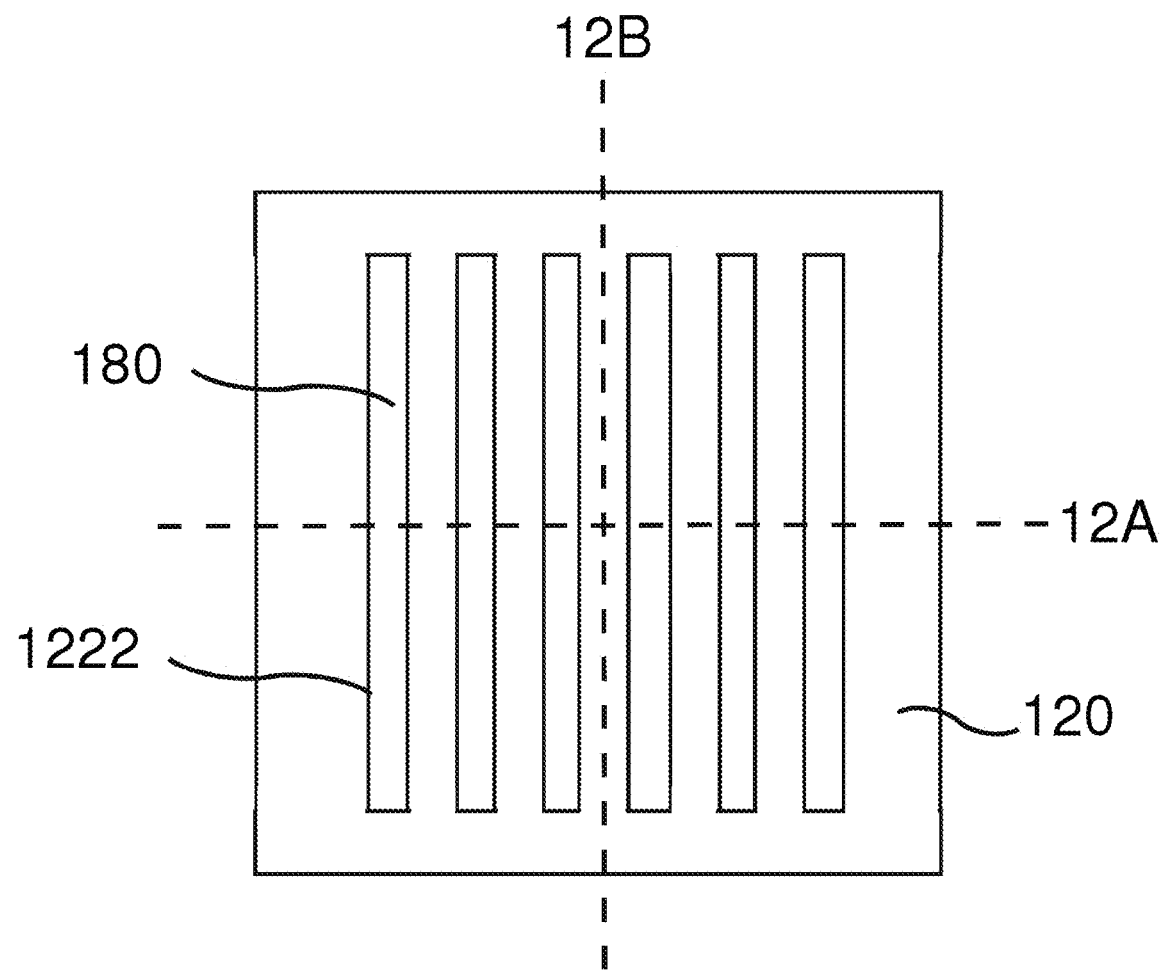
FIGS. 13A and 13B are top views illustrating multiple stages in the process of FIG. 11.
Figure 13B:
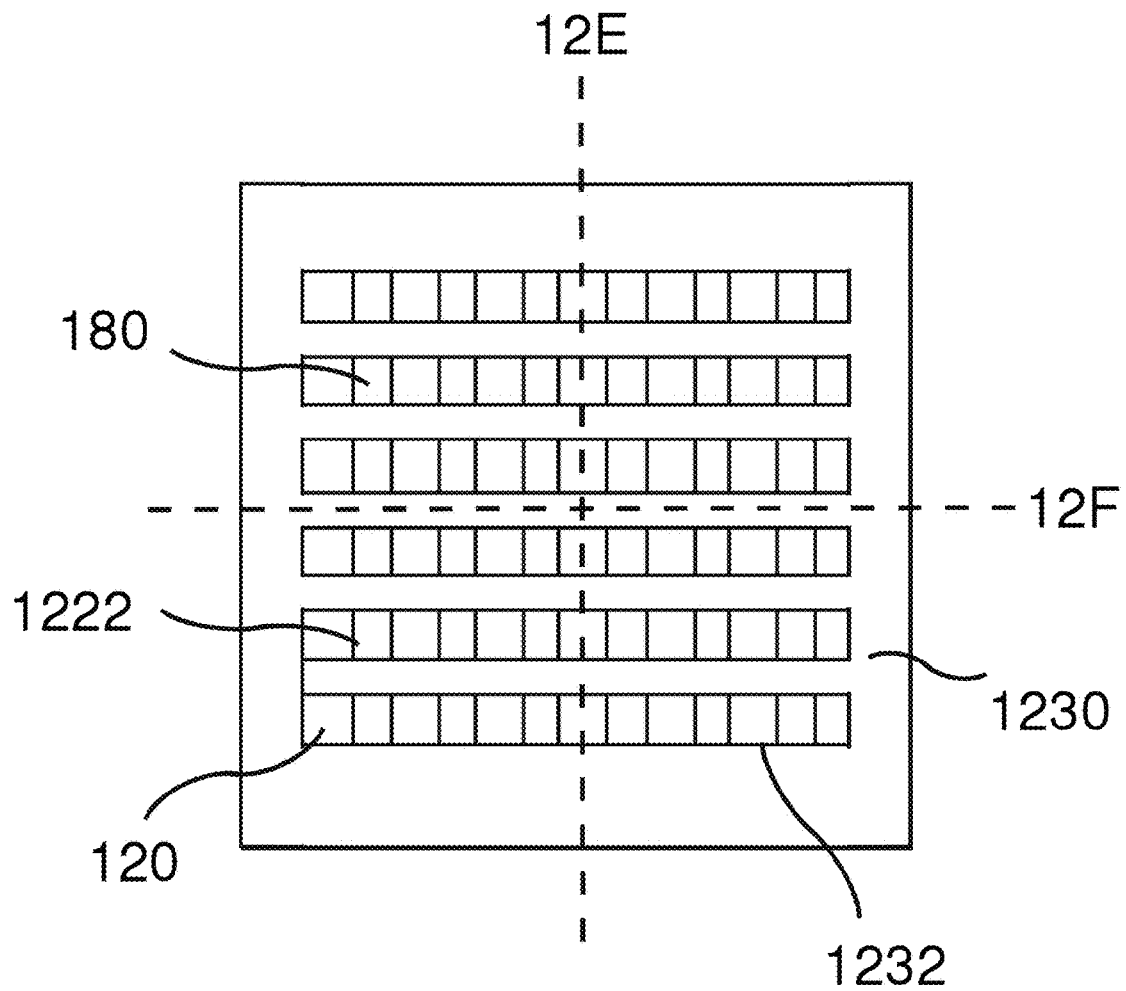
Figure 14A:
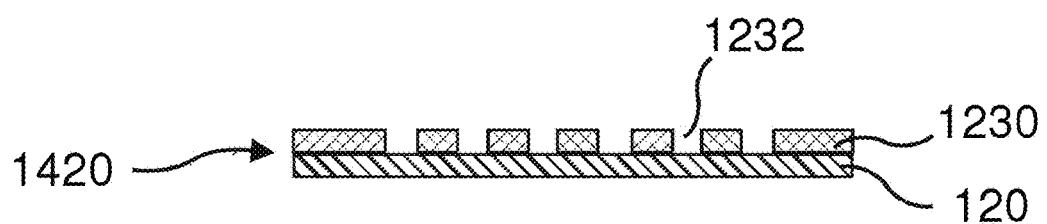
FIGS. 14A and 14B are cross-sectional views of a multi-layer microfilter 1420 in accordance with exemplary embodiments of the present invention.
Figure 14B:
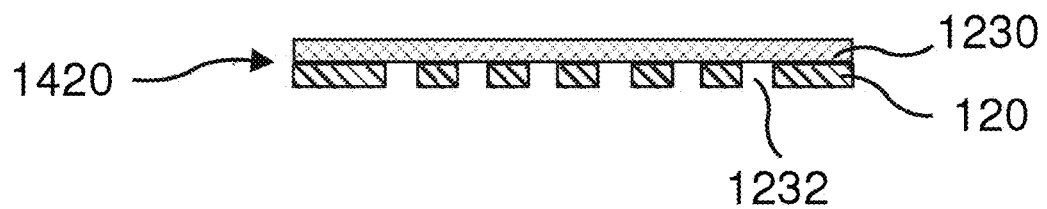
Figure 14C:
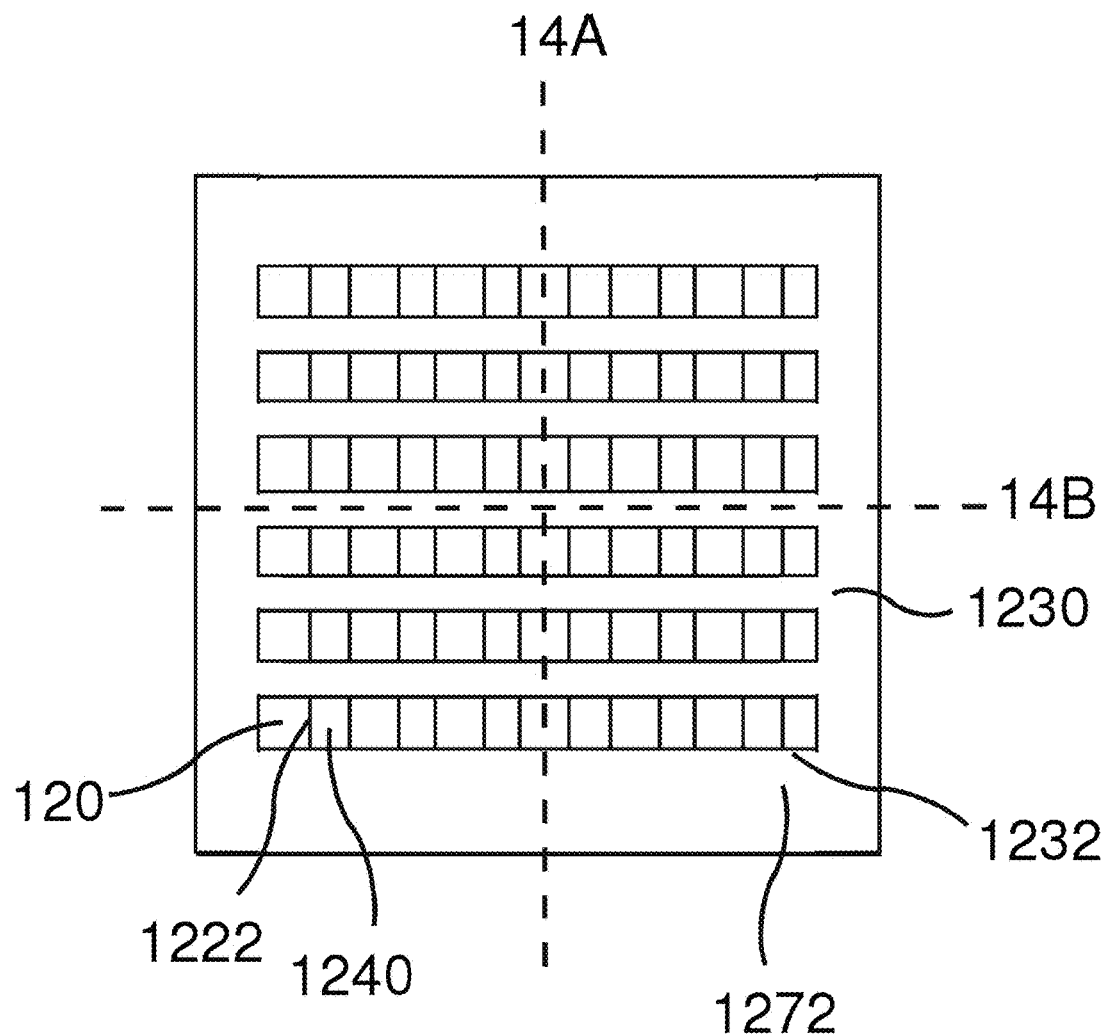
FIG. 14C is a top view of a multi-layer microfilter 1420 of FIGS. 14A and 14B.

FIGS. 12A-12K are cross-sectional views illustrating multiple stages in a process for manufacturing a multi-layer microfilter 1270 in accordance with embodiments of the present invention. FIG. 12L is a top view of multi-layer microfilter 1270 in accordance with embodiments of the present invention. FIG. 11 is a flow chart illustrating a process 1100 for manufacturing a multi-layer microfilter 1420 in accordance with embodiments of the present invention. FIGS. 14A and 14B are cross-sectional views of a multi-layer microfilter 1420 in accordance with embodiments of the present invention. FIG. 14C is a top view of a multi-layer microfilter 1420 of FIGS. 14A and 14B. The exemplary process of FIG. 11 will be described below with reference to FIGS. 12A-12F and FIGS. 14A-14C. FIGS. 13A and 13B are top views illustrating multiple stages in the process of FIG. 11.

At block 1120 of FIG. 11, a first microfilter 120 is formed on a substrate 180 from a layer of epoxy-based photo-definable dry film. In the embodiment illustrated in FIGS. 12A-12L, first microfilter 120 may be formed on substrate 180 by a process similar to the process 200 of FIG. 2A, described above, omitting the removal of microfilter 120 from substrate 180 at block 280. In certain embodiments, microfilter 120 comprises a polymer layer including a plurality of apertures. In certain embodiments of process 1100, a mask with a pattern configured for forming a plurality of elongate trenches in the dry film 100 may be used instead of mask 199 with pattern 198 configured for forming a plurality of pores in dry film 100. In such embodiments, the mask may have a pattern including elongate strips of metal so that corresponding elongate trenches may be formed in dry film 100 when dry film 100 is exposed through the mask.

FIG. 13A is a top view of microfilter 120 formed at block 1120 in accordance with embodiments of the present invention. As shown in FIG. 13A, microfilter 120 includes a plurality of elongate trenches 1222 and is disposed on a substrate 180 exposed through trenches 1222. FIG. 12A is a cross-sectional view of microfilter 120 taken along line 12A of FIG. 13A and FIG. 12B is a cross-sectional view of microfilter 120 taken along line 12B of FIG. 13A. As shown, line 12B is perpendicular to line 12A.

Figure 12C:
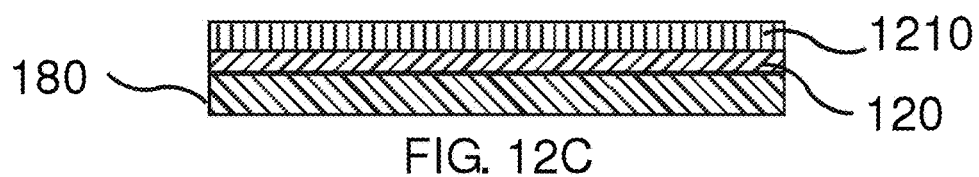
Figure 12D:
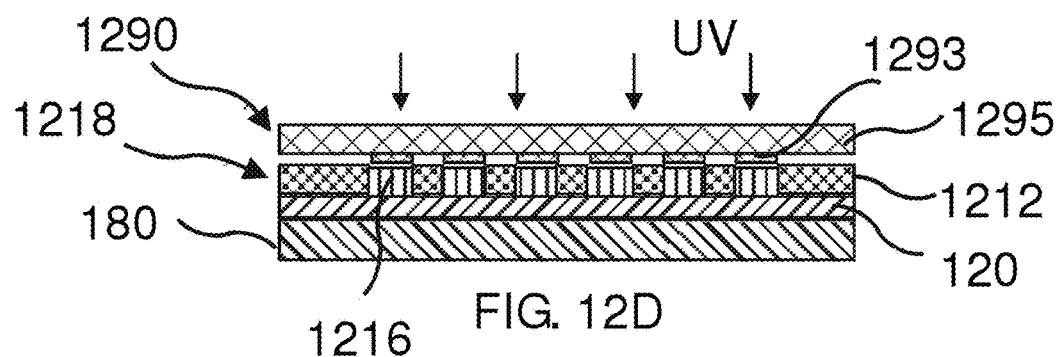

At block 1140 of FIG. 11, a layer of epoxy-based photo-definable dry film 1210 (which may be referred to herein as "dry film 1210") is laminated on microfilter 120, as shown in FIG. 12C. In certain embodiments, dry film 1210 is capable of bridging over features formed in the surface on which it is laminated. In such embodiments, dry film 1210 does not significantly fill trenches 1222 when laminated on microfilter 120. At block 1160, a second microfilter 1230 is formed from the layer of epoxy-based photo-definable dry film 1210, as described below. In certain embodiments, microfilter 1230 comprises a polymer layer including a plurality of apertures. As shown in FIG. 12D, dry film 1210 is exposed to energy through a mask 1290 to form an exposed dry film 1212 having a pattern 1218 of polymerized portions and non-polymerized portions 1216, as described above in relation to block 240 of FIG. 2A. In the embodiment illustrated in FIGS. 12A-12L, dry film 1210 is a negative resist. In other embodiments, dry film 1210 may be a positive resist and a different mask configured for use with a positive resist may be used. In the embodiment illustrated in FIGS. 12A-12L, dry film 1210 is exposed to energy in the form of ultraviolet (UV) light through an optical mask 1290 having a mask portion 1295 that is transparent to UV light and a mask pattern 1293 including a plurality of elongate strips that are opaque to UV light. In alternative embodiments, dry film 1210 may be exposed to X-rays through an X-ray mask instead of being exposed to UV light through optical mask 1290.

Figure 12E:
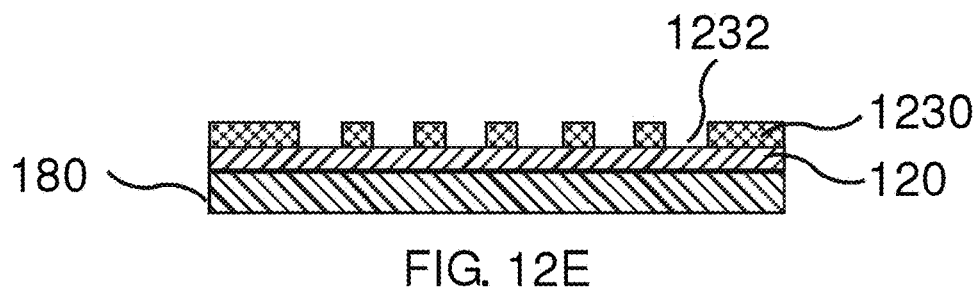
Figure 12F:
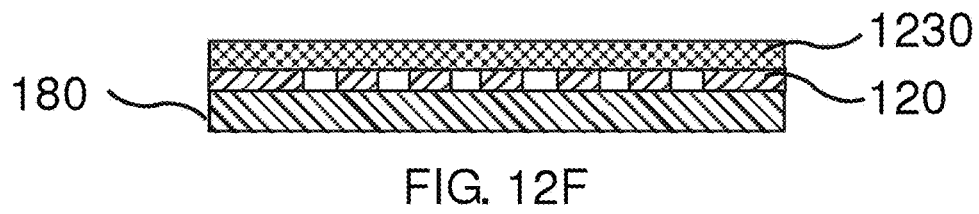
Figure 12G:
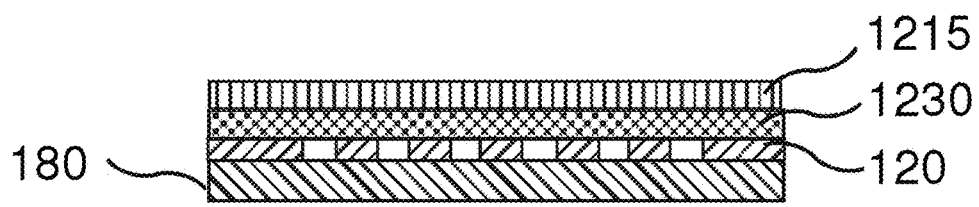
Figure 12H:
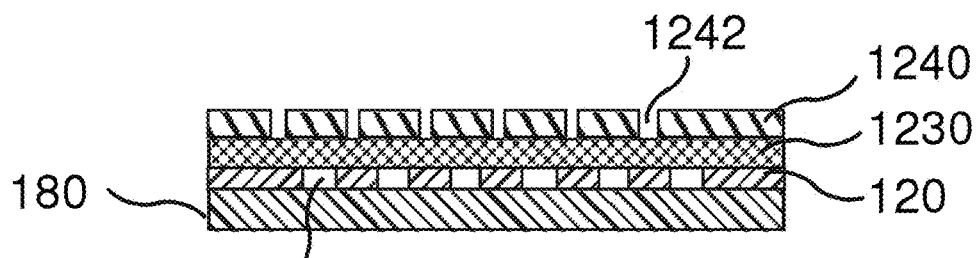
Figure 12I:
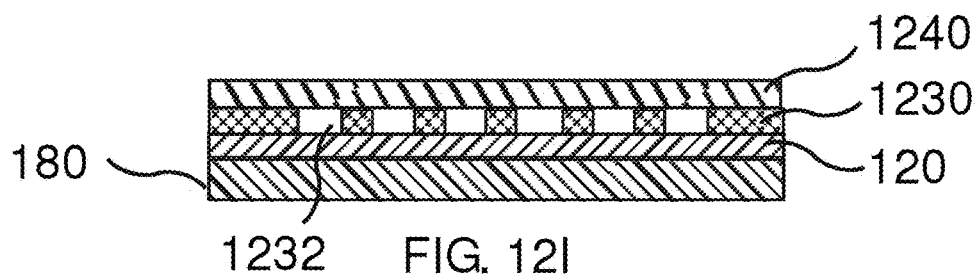
Figure 12J:
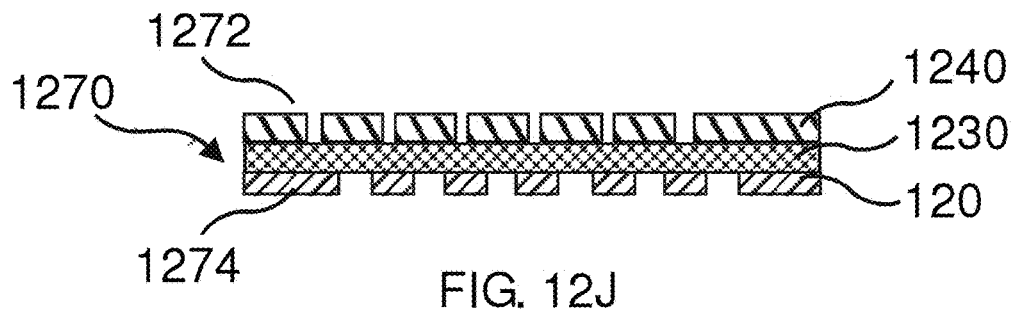
Figure 12K:
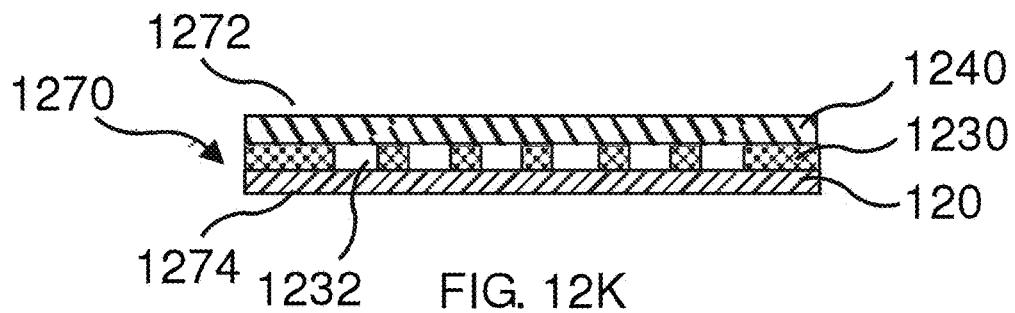
Figure 12L:
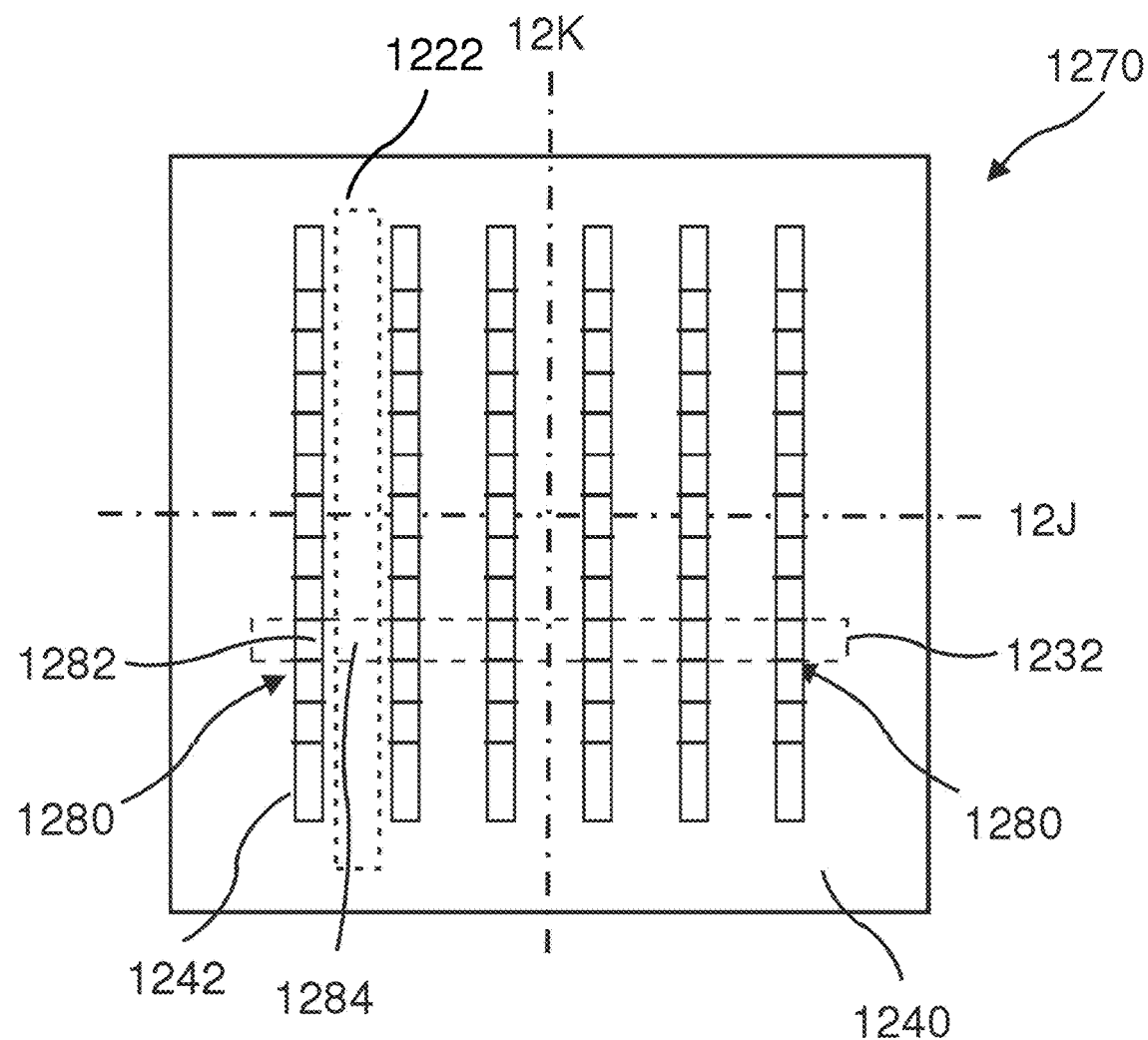
FIG. 12L is a top view of multi-layer microfilter in accordance with exemplary embodiments of the present invention.

In the embodiment illustrated in FIGS. 12A-12L, a polymeric microfilter 1230 having a plurality of trenches 1232 extending through microfilter 1230 is formed from exposed dry film 1212, as described above in relation to block 260 of FIGS. 2A and 2B, in one variation of block 1160. FIG. 13B is a top view of first and second microfilters 120 and 1230 in accordance with embodiments of the present invention. As shown in FIG. 13B, microfilter 1230 includes a plurality of elongate trenches 1232 and is disposed on first microfilter 120, which is exposed through trenches 1232. As shown in FIG. 13B, trenches 1232 of microfilter 1230 are formed substantially perpendicular to trenches 1222 of microfilter 120. FIG. 12E is a cross-sectional view of microfilters 120 and 1230 taken along line 12E of FIG. 13B, and FIG. 12F is a cross-sectional view of microfilters 120 and 1230 taken along line 12F of FIG. 13B. As shown, line 12F is perpendicular to line 12E. The thickness of each layer can be different.

In certain embodiments, after forming second microfilter 1230, substrate 180 may be removed from microfilter 120, as described above in relation to block 280 of FIG. 2A, to form a multi-layer microfilter 1420 shown in FIGS. 14A-14C. In the embodiment illustrated in FIGS. 14A-14C, multi-layer microfilter 1420 includes second microfilter 1230 disposed on first microfilter 120. As shown in FIG. 14C, multi-layer microfilter 1420 includes apertures 1240 extending through multi-layer microfilter 1420 where trenches 1222 and 1232 intersect. In certain embodiments, microfilter 1240 comprises a polymer layer including a plurality of apertures. FIG. 14A is a cross-sectional view of microfilter 1420 taken along line 14A of FIG. 14C, and FIG. 14B is a cross-sectional view of microfilter 1420 taken along line 14B of FIG. 14C. As shown, line 14B is perpendicular to line 14A. The thickness of each layer can be different.

In certain embodiments, as an alternative to forming microfilter 1420, a microfilter 1270 having a non-linear passage 1280 may be formed, as illustrated in FIGS. 12G-12L. In such embodiments, multi-layer microfilter 1270, shown in FIG. 12L, is formed by forming a third microfilter 1240 on first and second microfilters 120 and 1230 and removing substrate 180. Additionally, in such embodiments, after forming second microfilter 1230 on first microfilter 120 and substrate 180, as shown in FIG. 12F, a layer of epoxy-based photo-definable dry film 1215 is laminated on second microfilter 1230, as shown in FIG. 12G. Subsequently, third microfilter 1240 is formed from dry film 1215, as described above in relation to the formation of second microfilter 1230 and the processes of blocks 240 and 260 of FIGS. 2A and 2B. As shown in FIG. 12H, third microfilter 1240 includes a plurality of elongate trenches 1242 that are substantially perpendicular to trenches 1232 and substantially parallel with trenches 1222. Additionally, in certain embodiments, trenches 1242 are offset from trenches 1222 such that trenches 1242 are not directly above trenches 1222, as shown in FIG. 12H.

In certain embodiments, after forming third microfilter 1240, substrate 180 may be removed from microfilter 120, as described above in relation to block 280 of FIG. 2A, to form multi-layer microfilter 1270. FIG. 12L is a top view of multi-layer microfilter 1270. FIG. 12J is a cross-sectional view of multi-layer microfilter 1270 taken along line 12J of FIG. 12L, and FIG. 12K is a cross-sectional view of multi-layer microfilter 1270 taken along line 12K of FIG. 12L. As shown, line 12K is perpendicular to line 12J.

As shown in FIG. 12L, multi-layer microfilter 1270 includes non-linear passages 1280 extending through each of microfilters 1240, 1230, and 120 so as to extend from a first surface 1272 to a second surface 1274 (see FIG. 12J) of multi-layer microfilter 1270. In certain embodiments, each non-linear passage 1280 is defined by a first aperture 1282 at an intersection of trenches 1242 and 1232, a second aperture 1284 at an intersection of trenches 1232 and 1222, and a portion of trench 1232 connecting the first and second apertures. In embodiments in which a multi-layer microfilter 1270 has one or more non-linear passages 1280, the filtration path is longer than if multi-layer microfilter 1270 included only linear apertures. For clarity, only selected trenches 1232 and 1222 and selected non-linear passages are illustrated in FIG. 12L. In some embodiments, each non-linear aperture 1280 is interconnected with many other non-linear passages 1280 via trenches 1232.

In certain embodiments of the multi-layer microfilter 1270, the respective thicknesses of microfilters 120, 1230 and 1240 can be the same or different, the trenches of a microfilter may or may not all have the same size and/or shape, the trenches of different microfilters of the multi-layer microfilter may or may not all have the same size and/or shape. In some embodiments, elongate trenches 1242 may have a width of 5-7 microns and a length greater than 7 microns, wherein the length and the width are both perpendicular to the thickness of the microfilter. Alternatively or in addition, the trenches of thicknesses of microfilters may be non-linear, and the trenches of adjacent microfilters may be oriented at an angle other than 90 degrees with respect to one another. Alternatively or in addition, one or more of microfilters 120, 1230 and 1240 may include pores like any of the pores illustrated in FIGS. 9A-9D instead of trenches, and, in some embodiments, multi-layer microfilter 1270 may include more than three microfilters disposed on one another. Additionally, in certain embodiments, each of microfilters 120, 1230 and 1240 may be formed from the same type of epoxy-based photo-definable dry film.

Figure 15:
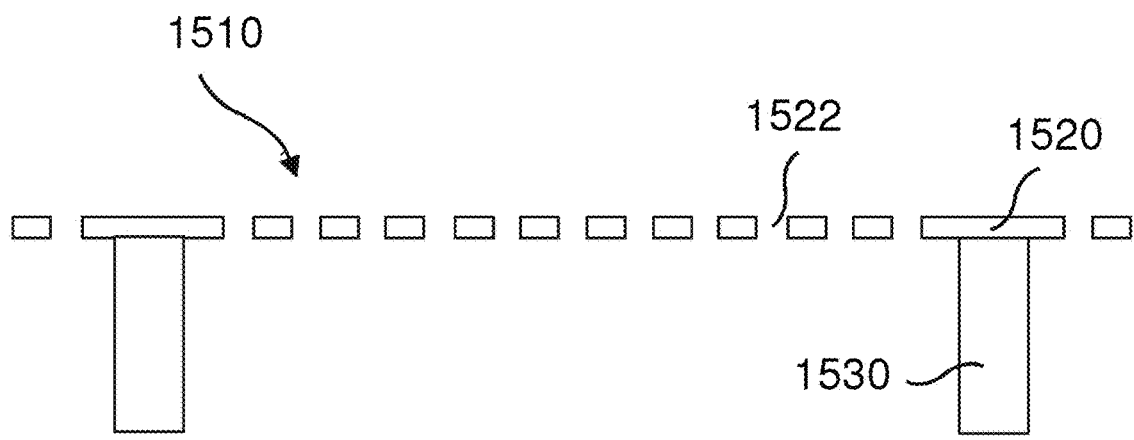
FIG. 15 is a cross-sectional view of a microfiltration structure including a microfilter and a support structure in accordance with exemplary embodiments of the present invention.

FIG. 15 is a cross-sectional view of a microfiltration structure including a microfilter and a support structure in accordance with embodiments of the present invention. In the embodiment illustrated in FIG. 15, microfiltration structure 1510 includes a microfilter 1520 having pores 1522 and disposed on a support structure 1530 configured to provide structural strength to microfilter 1520. In certain embodiments, support structure 1530 may be integrated with microfilter 1520. In some embodiments, support structure 1530 is a grid support structure. In certain embodiments, microfiltration structure 1510 may be formed by a process similar to the process described above in relation to FIGS. 12A-12F and FIGS. 14A-14C. In such embodiments, microfilter 1520 and support structure 1530 are each formed from a layer of epoxy-based photo-definable dry film and patterned using an appropriate mask. In such embodiments, microfilter 1520 is formed on support structure 1530 or support structure 1530 is formed on microfilter 1520.

The microfilter can be a combination of pores with other structure elements above or below the layer that form the pores to form many filtration devices. A few examples of two layers or three layers structures with and without pores are illustrated in FIGS. 16A-16J. These devices have applications for isolating cells from body fluids and for biological assays.

Figure 16A:
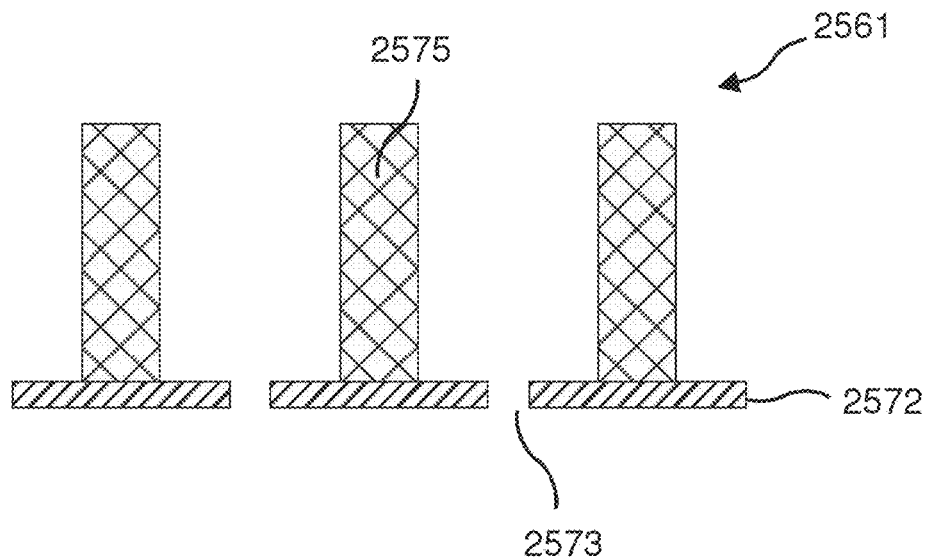
FIG. 16A is a cross-sectional view of a microfiltration structure including pores in the microfilter and posts above the microfilter in accordance with exemplary embodiments of the present invention.
Figure 16B:
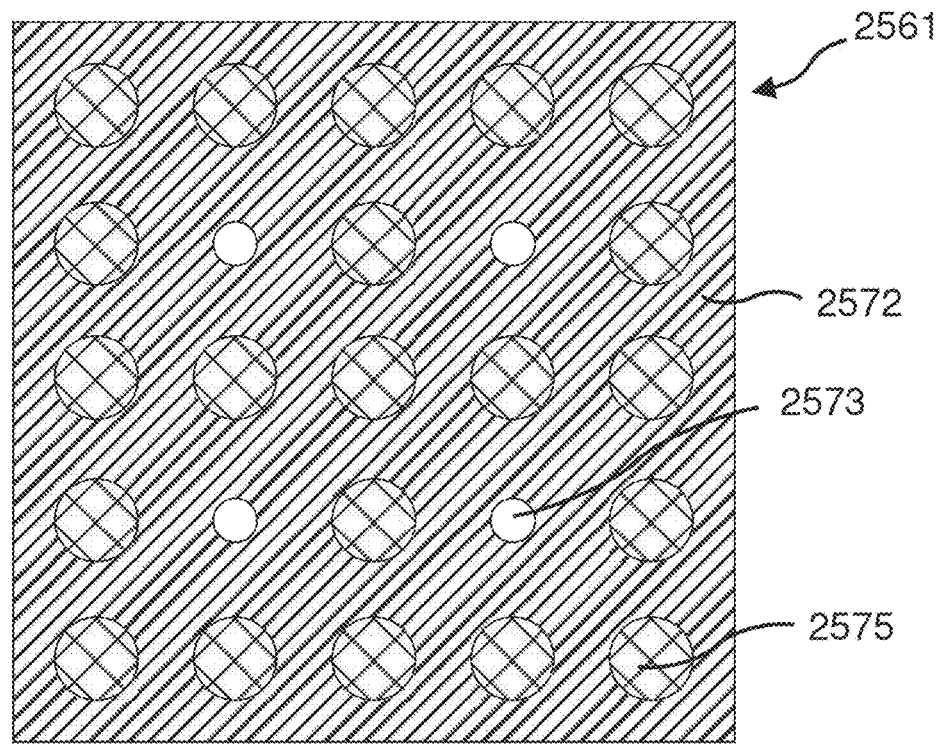
FIG. 16B is a top view of a microfiltration structure including pores in the microfilter and posts above the microfilter in accordance with exemplary embodiments of the present invention.

FIG. 16A is an exemplary embodiments of a two layered microfilter, showing a side view of microfilter 2561 containing posts 2575 on microfilter base 2572 with pores 2573. FIG. 16B shows the top view of posts 2575 on microfilter base 2572 with pores 2573. The pore can be circular, square, rectangle, etc. The posts can also of a variety of shapes such as circles, squares, rectangles, etc. The arrangement of the posts and the density can be regular, varied spatially or random as long the posters are not closer than 30 µm and the posts don't cover the pores. The pores can have various shapes, sizes and distributions. The posts can also have various shapes, sizes and distributions.

Figure 16C:
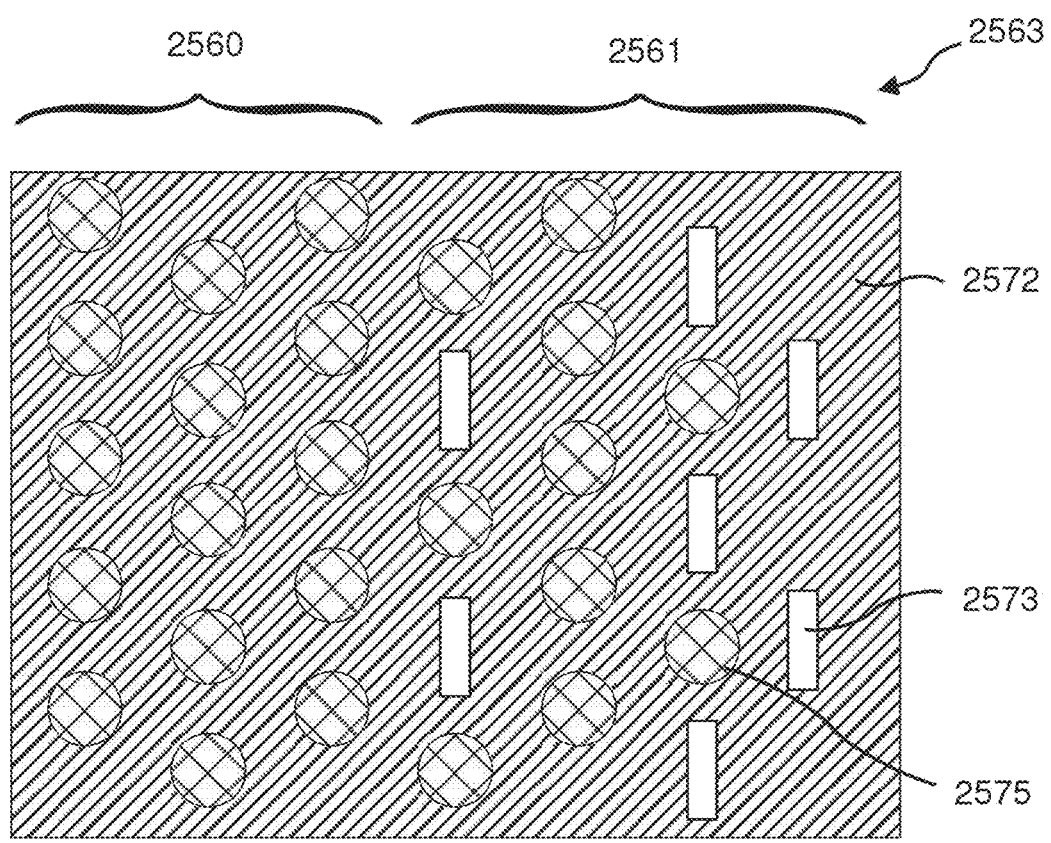
FIG. 16C is a top view of a microfiltration structure including rectangular pores in the microfilter and posts above the microfilter in accordance with exemplary embodiments of the present invention.

FIG. 16C is another exemplary embodiments of a two layered microfilter, showing the top view of a microfilter 2563 where pore is rectangular shaped 2573, but not distributed everywhere on the base support 2572, and posts 2575 is also not distributed everywhere. The pores can have various shapes, sizes and distributions. The posts can also have various shapes, sizes and distributions.

Figure 16D:
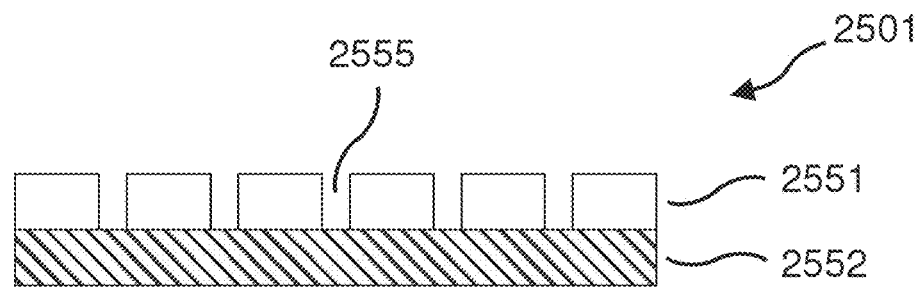
FIGS. 16D and 16E are side views of another microfilter according to an exemplary embodiment of the present invention made by two layers of material with different patterns in each layer.
Figure 16E:
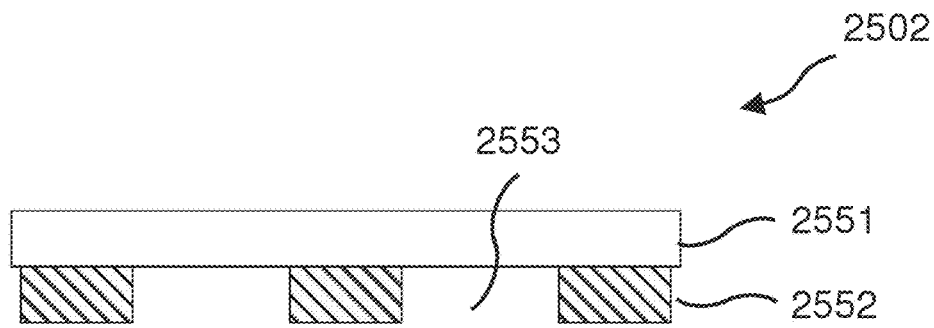
Figure 16F:
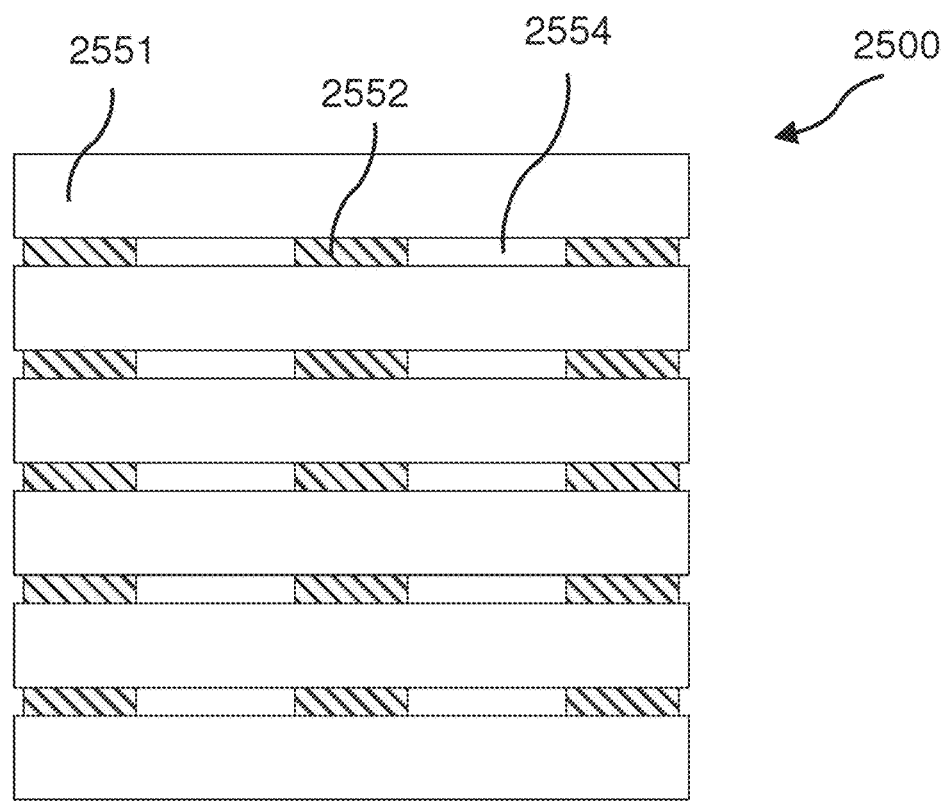
FIG. 16F is the top view of the microfilter according to an exemplary embodiment of the present invention made by two layers of material with different patterns in each layer.
Figure 16G:
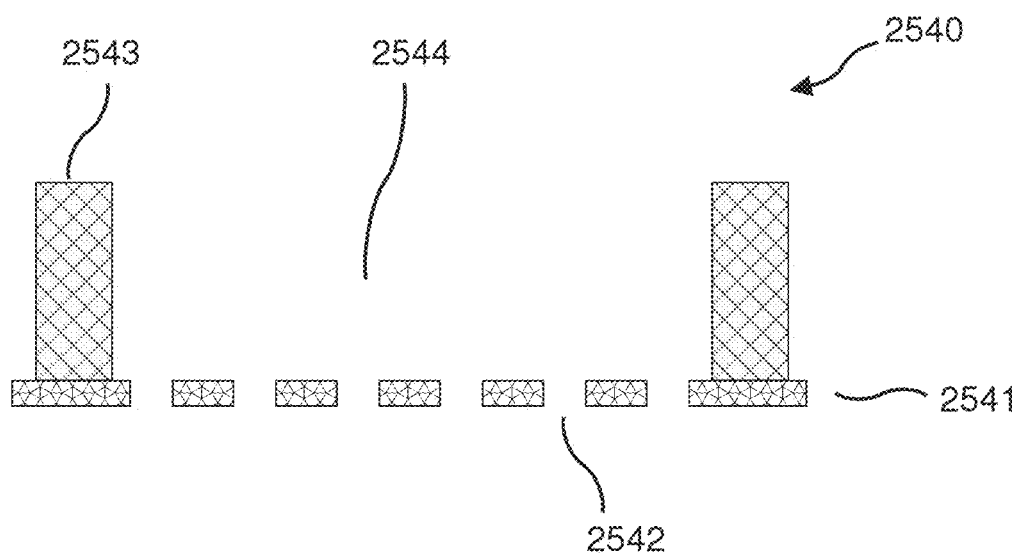
FIGS. 16G and 16H are side views of another microfilter according to an exemplary embodiment of the present invention made by two layers of material with different patterns in each layer.
Figure 16H:
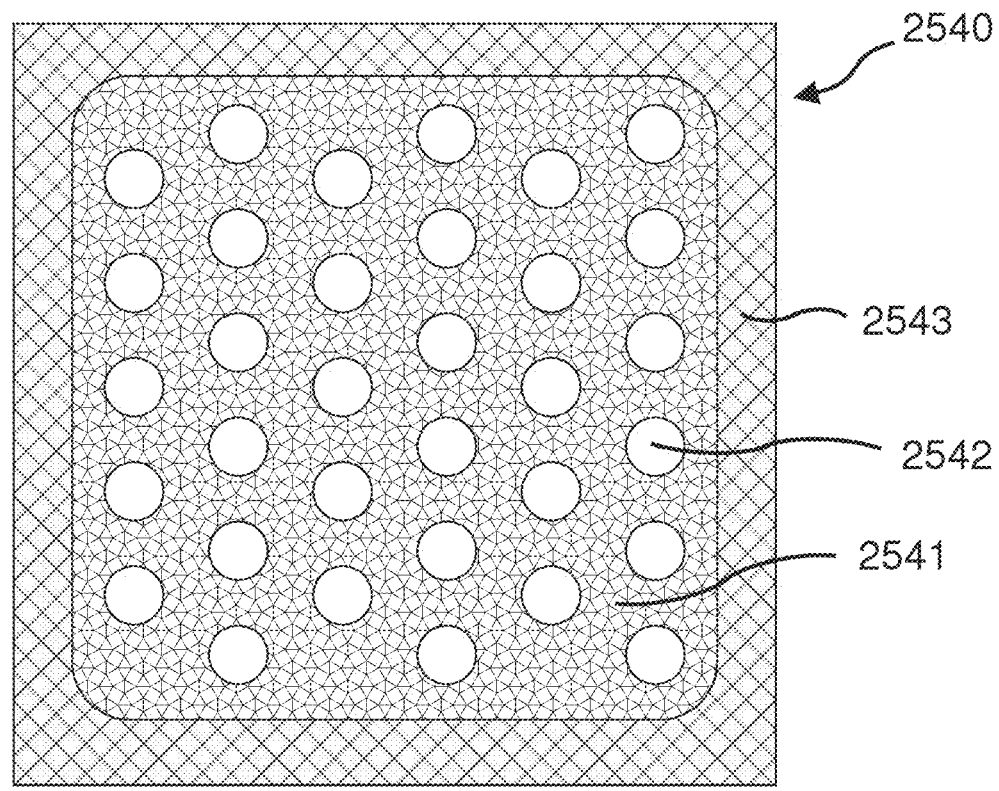
Figure 16I:
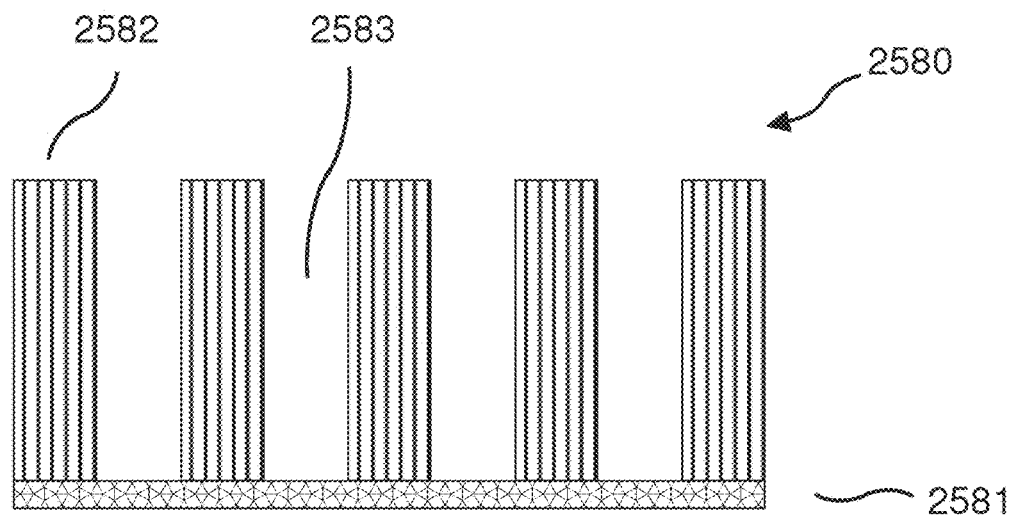
FIGS. 16I and 16J are side views of a device according to an exemplary embodiment of the present invention with many wells suitable for many assays made by two layers of material with opening on the top layer and solid bottom layer.
Figure 16J:
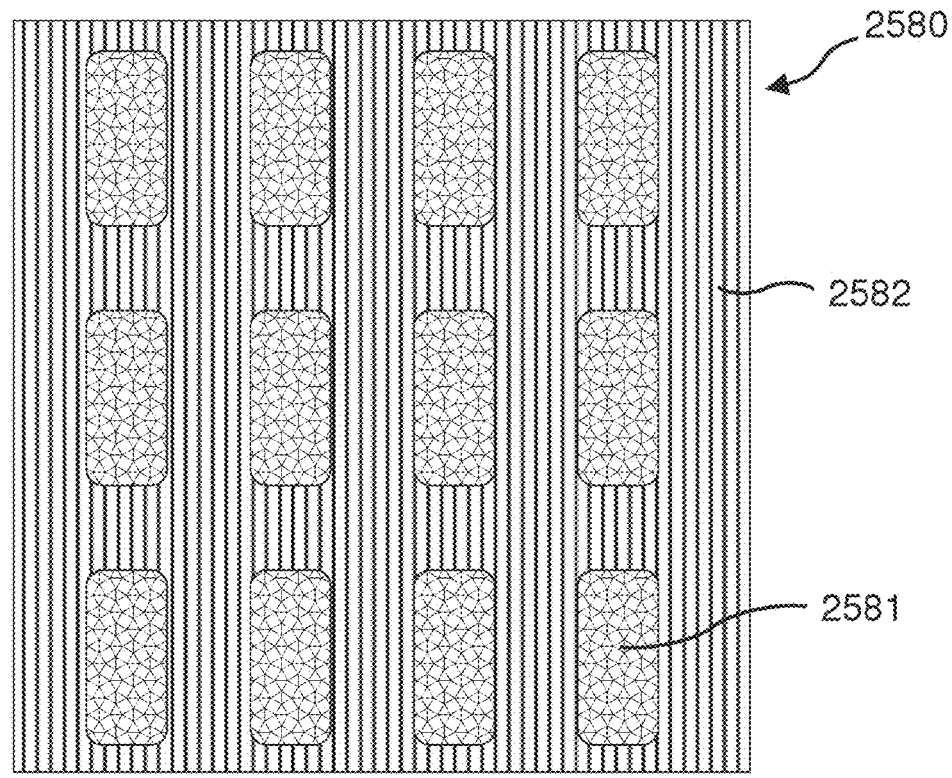

FIG. 16I is an exemplary embodiments of a two layered device 2580, showing the side view of bottom layer 2581 without pores. The top layer 2582 forms wells 2583. FIG. 16J shows the top view. This well structure can be fabricated using the same procedure described in FIGS. 1A-1D followed by procedure described in FIGS. 12A-12F except no mask is needed for FIG. 1B.

Pore dimensions depends on the needs of specific applications. For example, pore diameter of 7-8 microns is the commonly preferred for circulating tumor cells from human blood, while circulating tumor cells originated in mice are smaller than in humans, so smaller pores are preferred for mice studies. For rectangular pores, width of 5-7 µm are preferred for collecting circulating tumor cells from human blood and the length is not critical as long as the filters don't deform during filtration.

FIGS. 16D-16F is another exemplary embodiment of a two layered microfilter with different patterns in each layer of the material according to an exemplary implementation. FIG. 16D showing the first side view 2501 of a two layer microfilter with the top layer 2551 and bottom layer 2552. The top layer are of strips with slot opening 2555. FIG. 16E is the second side view 2502 of the two layer microfilter turned 90 degrees. The bottom layer 2552 has open slots 2553. FIG. 16F shows the top view of the microfilter 2500. The cross strips forms effective rectangular pores 2554.

In an advantageous exemplary implementation, dimensions of the top channel 2555 between two top strips of 2551 are 5-7 µm for isolation of tumor cells. Small width of 10-20 µm for 2551 would allow high filtration rate, but a wide range of with for 2551 are functional. The width of 2552 can vary, but for high filtration rate, the width may be 5-20 µm. The gap between two strips of 2552 that form the pore 2553 can also vary. For high filtration rate, the gap can be from 10-60 µm. The thickness of 2551 about 10 µm may be preferable. In an exemplary implementation, thickness of bottom layer 2552 can advantageously be approximately the same as the gap between two strips of 2552.

FIGS. 16G-16H are side view and top view of an exemplary device 2540 consisting of microfilter 1541 with pores 2542 at the bottom of wells 2544. The structure shown in FIG. 16H is repeated over the whole microfilter area. An application of the device 2540 is to filter the cells and followed by culture of the cells in the wells 2544. Again pores can have a variety of shapes and sizes. The size, shape and depth of the well 2544 can also be varied as appropriate for different uses. The density of the wells 2583 can also be varied.

An exemplary application of devices 2500, 2540, 2561 and 2563 includes rare cell isolation where the mechanism of isolation of the cells is based on size.

FIGS. 16I-16J are side view and top view of an exemplary device 1580 consisting of wells 2583 formed by 2582 with solid bottom 2581. These can be used for a variety of biological assays. The size, shape and depth of the wells 2583 can be varied. The density of the wells 2583 can also be varied.

Various materials for forming devices described in FIGS. 16A-16J above can include epoxy-based photo-definable dry films and other types of photo-definable dry films. The methods to fabricate those structures using photo-definable dry films are described above and in, for example, PCT/US11/20966.

Coating of the Microfilters

In certain embodiments, surface functionalization of a polymeric microfilter may provide a surface of the microfilter with surface properties desired for a particular application of the microfilter. Some materials can be directly disposed on the microfilter surfaces. Other times, the microfilter surfaces need to be treated. In one embodiment, the surface of the polymeric microfilter can be functionalized by performing a plasma treatment on the surface of the microfilter to activate the surface to enable chemical compounds and/or organic materials to attach to the surface. In some embodiments, another surface modification technique is to coat the microfilter with a thin layer of a metallic substance.

Figure 17:
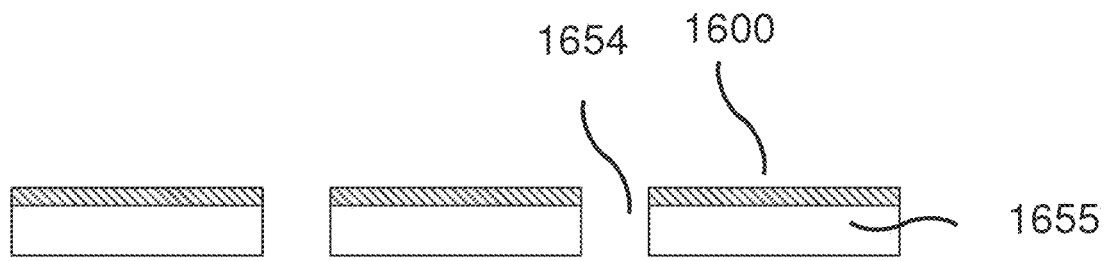
FIG. 17 is a cross-sectional views of coated planar microfilters in accordance with exemplary embodiments of the present invention.
Figure 18:
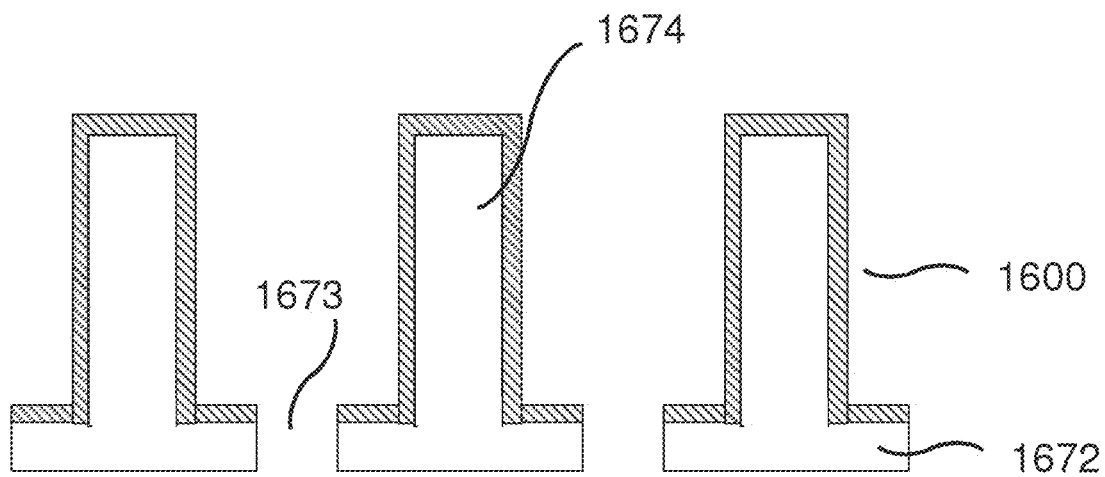
FIG. 18 is a cross-sectional views of coated structured microfilters in accordance with exemplary embodiments of the present invention.

FIGS. 17 and 18 are cross-sectional views of coated microfilters in accordance with embodiments of the present invention. In the embodiment illustrated in FIG. 17, microfilter 1655 includes a coating 1600 on surface of one layer microfilter 1655. Coating 1600 can also be disposed on multi-layered microfilters. Coating 1600 can also be disposed on microfilters produced by other methods and by other materials. In FIG. 18, the multi-layer device is formed from epoxy-based photo-definable dry film, as described above in relation to FIGS. 16A-16J. In the embodiment illustrated in FIG. 18, microfilter 1672 includes a coating 1600 on surface of the top structure and flat portions of the microfilter 1672. Coating 1600 can also be disposed on microfilter structures produced by other methods and by other materials. Coating 1600 can also be disposed on the surface of structure shown in FIGS. 16I-16J even without pores.

In certain embodiments, coating 1600 may be formed from a metallic substance, a nanoparticle colloidal substance, chemical compound, or an organic substance. In such embodiments, these surface coatings can be used to attach analyte recognition elements, DNA, aptamers, surface blocking reagents, etc. In other embodiments, coating 1600 may include analyte recognition elements, DNA, aptamers, surface blocking reagents, etc. In certain embodiments, the surface coatings may be used to attach, for example, macromolecules such as polypeptides, nucleic acids, carbohydrates and lipids. Examples of polypeptides that may be used as analyte recognition elements include, for example, an antibody, an antigen target for an antibody analyte, a receptor (including a cell receptor), a binding protein, a ligand, or other affinity reagent to the target analyte. Examples of nucleic acids that may be used as analyte recognition elements include, for example, DNA, cDNA, or RNA of any length that allows sufficient binding specificity. In such embodiments, both polynucleotides and oligonucleotides can be used as analyte recognition elements. In other embodiments, gangliosides, aptamers, ribozymes, enzymes, antibiotics or other chemical compounds may be used as analyte recognition elements. In certain embodiments, analyte recognition coatings or elements may include, for example, biological particles such as a cell, a cell fragment, a virus, a bacteriophage or tissue. In some embodiments, analyte recognition coatings or elements may include, BSA, fetal bovin serum (FBS), selectins including P-selectins, E-selectins, L-selectins, nanoparticles, nanotubes, halloysites, dendrimers, chemical linkers or other chemical moieties that can be attached to a microfilter and which exhibit selective binding activity toward a target analyte.

In some embodiments, coating 1600 may be formed from a metallic substance including gold, nickel, etc. In certain embodiments, coating 1600 includes gold coated on chromium. In some embodiments, it may be preferable to form coating 1600 from gold, as certain chemical compounds and organic materials readily attach to gold. In other embodiments, coating 1600 may be formed from carbon nanotubes. In the embodiment illustrated in FIGS. 17-18, coating 1600 is disposed on one surface of microfilters. In other embodiments, one or more surfaces of microfilters may be coated with coating 1600. In some embodiments, microfilters may be completely coated with coating 1600. Coating 1600 may be disposed on one or more surfaces of any of the microfilters described herein in accordance with embodiments of the present invention, including multi-layer microfilters. In certain embodiments, coating 1600 may be disposed on one or more surfaces of multi-layer microfilter 1620.

In some embodiments, examples of chemical compounds and organic materials that may be useful for assays when deposited on the surface of a microfilter include are self-assembled monolayers with a range of functionality including amine, carboxyl, hydroxyl, epoxy, aldehyde, and polyethylene glycol (PEG) groups. These compounds and materials may be deposited on the surface of a microfilter using silane chemistry with solution immersion or vapor deposition. In certain embodiments, for example, grafting PEG-triethoxysilane onto an oxidized polymer renders the surfaces hydrophilic in a controlled manner. In other embodiments, a surface of a polymeric microfilter can be functionalized with avidin, biotin, protein A, protein G, antibodies, etc.

In certain embodiments, coating a surface of a microfilter with a metallic substance may provide other benefits in addition to facilitating the attachment of chemical compounds and/or organic materials. In some embodiments, for example, a layer of a metal metallic substance, having an appropriate thickness, can block transmission of light through the microfilter. In certain embodiments, a thickness sufficient to block the transmission of light is about 40 nm. In other embodiments, this thickness may vary depending on the substance used. Additionally, metallic substances are generally electrically conductive. In some embodiments, when the metallic substance is electrically conductive, the coating may reduce or eliminate charging of the surface of the microfilter. In alternative embodiments, a microfilter may be coated with a thin layer of PARYLENE. In other embodiments, a microfilter may be coated with a thin layer of fluorinated ethylene propylene (FEP), polytetrafluoroethylene (PTFE), perfluoroalkoxy (PFA), or another similar material. In such embodiments, coating a microfilter with one of these materials can reduce nonspecific binding; however, the fluorescent nature of these materials may make them disadvantageous when a microfilter is to be analyzed via microscope imaging.

In certain embodiments, single layer or multi-layered microfiltration devices can be coated with an antibody against surface markers on the CTCs to further improve the collection of live CTCs. In such embodiments, capture efficiency of live CTCs may be improved. In some embodiments, useful surface markers may include antibodies against EpCAM, HER2, EGFR, KRAS, Vimentin, and MUC-1, but not limited to these surface markers, P-selectin, E-selectin, other selectins, ligends, aptamers, etc. In embodiments in which the microfilter is coated with cell surface recognition elements, the microfiltration can capture CTCs through size exclusion and surface markers simultaneously.

Filter Holder and Filtration Devices

The steps of filtration of large rare cells from body fluids on the microfilter or concentrated in a reduce volume with reduced contaminants can be performed with minimal human intervention if the microfilter can be installed in a microfiltration device. The present invention details a method to use microfilters using filter holders.

Figure 19:
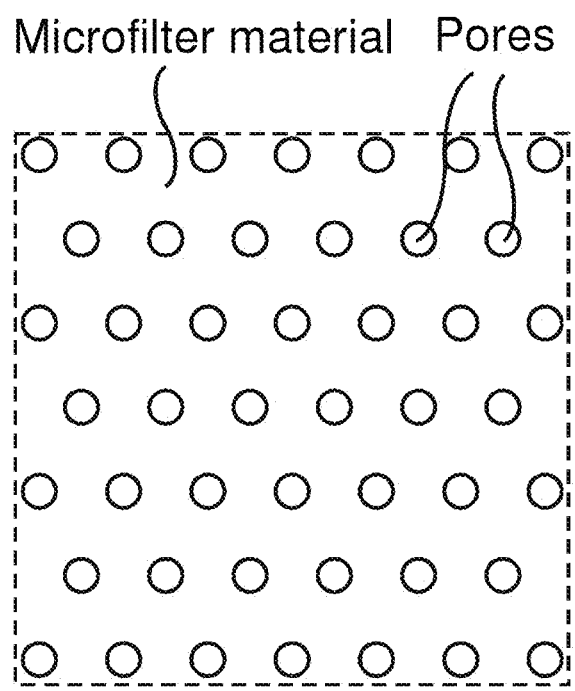
FIG. 19 illustrate an example of lithographically fabricated microfilter according to an exemplary embodiment of the present invention using epoxy—based photo-definable dry film with the pore geometry and locations defined by an optical mask.

Microfilters made from epoxy-based photo-definable dry films, as shown in FIG. 19, can be used in a variety of ways to analyze rare cells such as CTCs from body fluids. Rare cells can be collected on the epoxy-based photo-definable dry film microfilters and other precision microfilters. Following the rare cells collection, rare cells can be analyzed using the following methods:

Enzymatic assays in rare cells such as CTCs can be test to evaluate viability and enzymatic activities;

Histopathological staining to look at cell morphology;

Immunofluorescence staining to look for expression of biomarkers to identify cancer subtype, or to determine biomarker mutation, or cell type. These information can be used to determine cancer therapy and monitor treatment; immunofluorescent staining can be used to perform enumeration of CTCs, based on DAPI (positive), Cytokeratins (CKs) (positive), such as CK8, 18, 19 and others, and CD45 (negative) cells, and count the number per ml of blood to monitor cancer treatment and recurrence;

Fluorescent in situ hybridization (FISH) to identify gene amplification, number of copies of biomarker genes, gene translocation, to identify cancer subtypes to determine therapy and monitor treatment; mRNA FISH can also be performed to determine the marker is overexpressing.

Nucleic acid assays for mRNA, microRNA and genomic DNA biomarkers, and gene mutations to identify cancer subtypes to determine therapy and monitor treatment;

Sequencing the genes to identify gene mutations, amplification and translocations to identify cancer subtypes to determine therapy and monitor treatment; and Culture rare cells, such as CTCs, to increase the number of cells. These cells can then be used to perform the assays described in bullets above. In addition, viable cells can be used to determine the effect of drugs on the cancer cells to determine therapy.

Culture rare cells on microfilters coated with analyte/markers recognition elements for analytes/markers that can be secreted by the CTCs. Assay similar to EPISPOT can be performed using the microfilter.

Some of those assay methods can be combined or performed sequentially on rare cells collected on epoxy-based photo-definable dry films. For example, rare cells collected on epoxy-based photo-definable dry films can be performed sequentially to obtain different information from the same cells. Some examples are: (1) Perform enumeration and for a cancer surface biomarker, followed by FISH assay and finally histopathological staining, (2) perform immunofluorescent staining to count the number of rare cells and at the same time determine over-expression of biomarker(s), mutated biomarker(s), cell type, and/or other information, followed by histopathological staining, (3) perform FISH to identify a marker followed by histopathological staining.

According to exemplary embodiments of the present invention, filtration devices to hold the filter and perform filtration are designed to have the following features:

The filter holder to hold the filter flat without causing twisting.

This filter holder has a large opening in the inlet unit. This is to allow easy access of the reagents to microfilter surface and visual access to the microfilter, where the cells are collected, and allow visualization of the filter from above.

The filter holder will allow performance of at least some types of assay in the filter holder.

The filter holder will allow different attachment of input sample holder above the filter holder, and syringe, stopper on the filter flask connected to a vacuum pump or vacutainer holder below.

According to an exemplary embodiment of the present invention, a filter holder allows for (i) filtration of the liquid sample through the microfilter, (ii) ability to perform assays with the microfilter in the holder, (ii) easy access to the microfilter in the filter holder, (iv) easy installation of the microfilter into the filter holder, (v) easy removal of the microfilter from the filter holder, and (vi) filter holder material capable of tolerating temperature required for the assays, and (vii) filter holder material capable of tolerating chemicals used in the assays.

Figure 20:
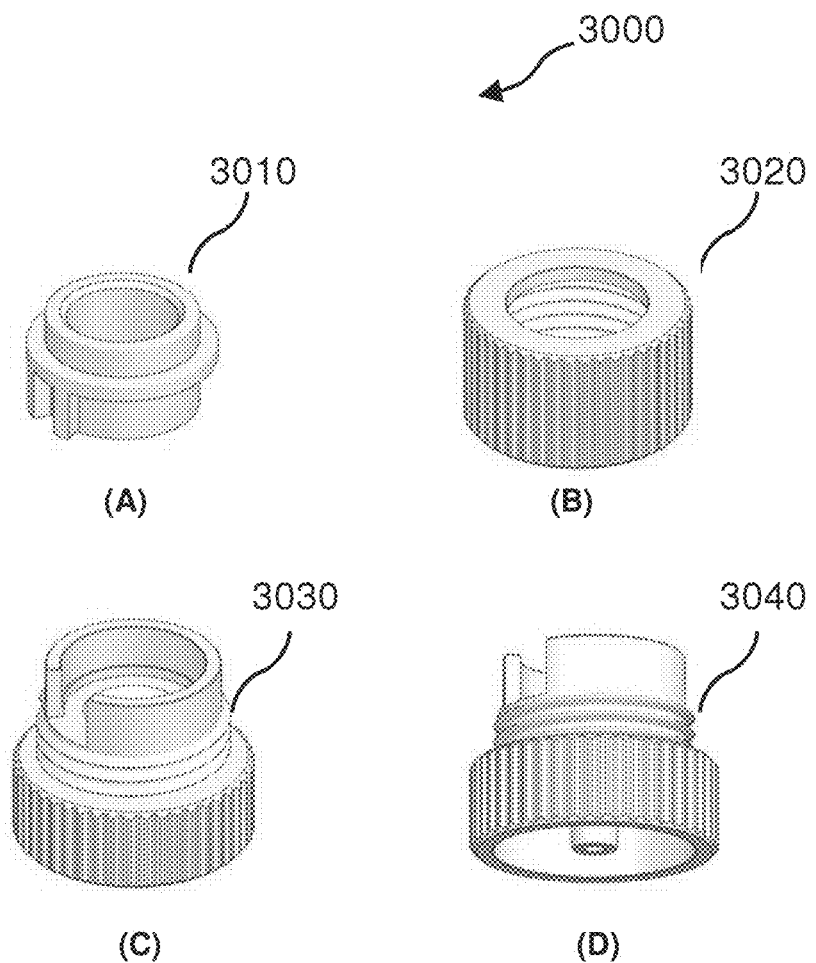
FIGS. 20A-20D illustrates the components of a filter holder in accordance with exemplary embodiments of the present invention.

FIGS. 20A-20C show three components that forms a filter holder according to an exemplary embodiment of the present invention, including: an inlet unit 3010, a nut 3020 and an outlet unit 3030 (top view FIG. 20C and the bottom view FIG. 20D). In an exemplary implementation a syringe or vacutainer holder with a Lure-Lock can be attached to the outlet unit of the filter holder. In an exemplary implementation an output unit can include a cut out on the top ring, for example, to allow access to the microfilter to allow easy removal of microfilters from the filter holder.

Figure 21:
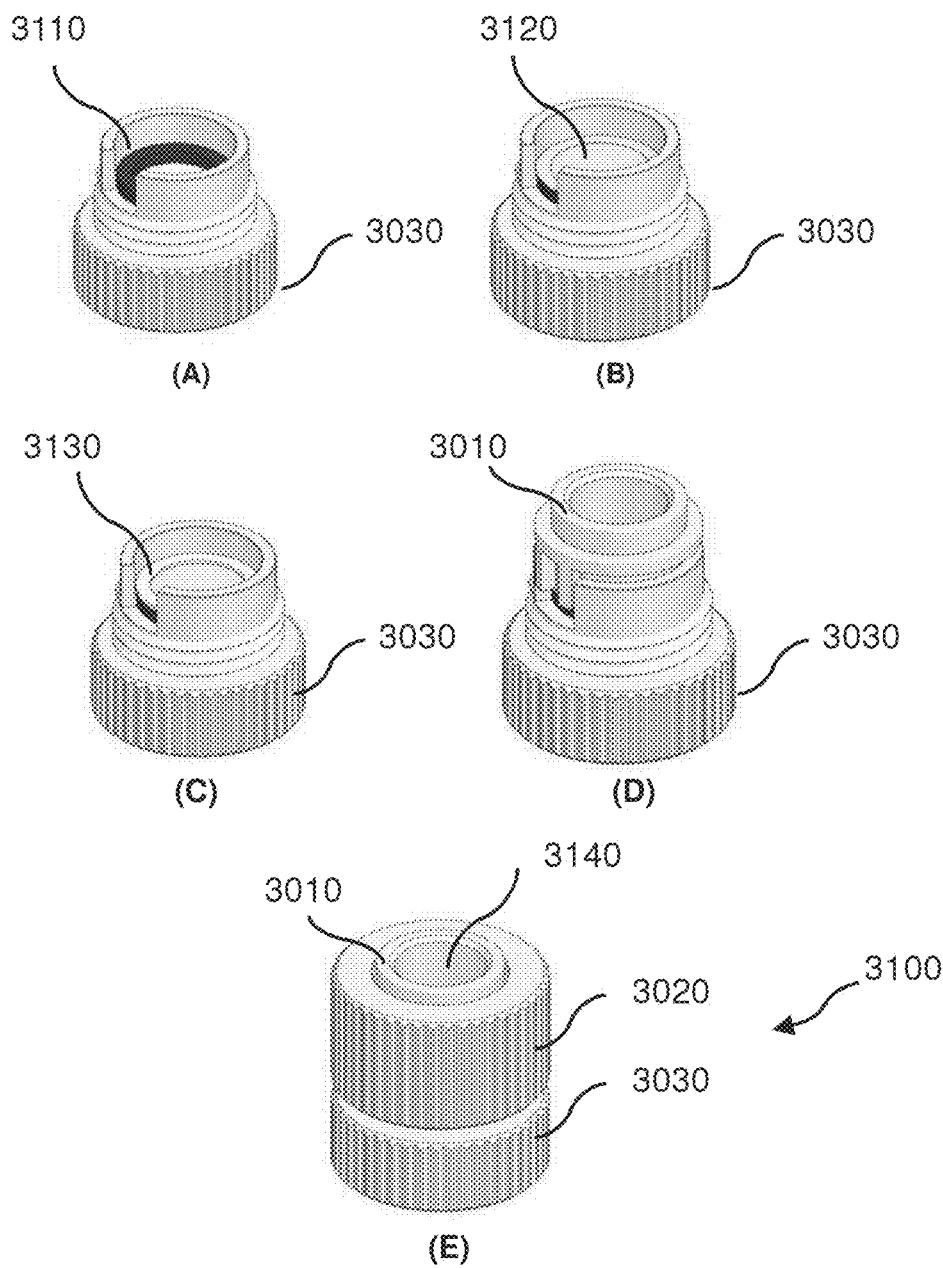
FIGS. 21A-21E illustrates the assembly process of the microfilter in the filter holder illustrated in FIGS. 20A-20D in accordance with exemplary embodiments of the present invention.

FIGS. 21A-21E show the assembly of the filter holder according to an exemplary embodiment of the present invention where a gasket 3110 is placed inside the outlet unit as shown in FIG. 21A. A round microfilter 3120 with the appropriate diameter for the filter holder is placed above the gasket, FIG. 21B. A second gasket 2130 is place above the microfilter 3120, FIG. 21C. The inlet unit 3010 is placed into the outlet unit 3030 by properly aligning the two components as shown in FIG. 21D. Finally the nut 3020 is installed to tighten the filter holder system to prevent leakage of the liquid sample around the microfilter inside the holder. While one gasket may be sufficient, a plurality of gaskets may be used, for example to prevent leakage, as needed. The gasket can be of different material or design. In an exemplary filter holder design, a microfilter installed in a filter holder system will remain flat, experience compression to form a tight seal, but not experience any twisting force.

There are a lot of potential variations of the filter holders in keeping with the scope of exemplary embodiments of the present invention, including without limitation:

The filter holder can have different sizes to accommodate different microfilter sizes. The common microfilter sizes are 0.5 inch (13 mm) and 1 inch diameters, but are not limited to these dimensions.

The filter outlet unit can have more than one opening. The opening is to allow easy removal of microfilter from filter holder and prevent the microfilter from becoming twisted by fixing in place the inserted inlet unit.

The shape and dimensions of different component of the filter holder can vary. One of the features of the filter holder concept according to exemplary embodiments of the present invention is pressing down on the inlet unit to prevent leakage. In an exemplary embodiment, a nut is used to hold down the inlet unit.

The inlet unit can also be held down by changing the nut to a snap-on part.

The outlet 3030 can have a female connector or a male connector.

The filter holder can be designed to accommodate one gasket under the microfilter or two gaskets, one above and one below the microfilter.

A filter support structure can be added to the inside of output units of the filter holders. Support structure may not be needed for epoxy-based photo-definable dry film microfilters because the material is sufficiently strong.

Figure 23:
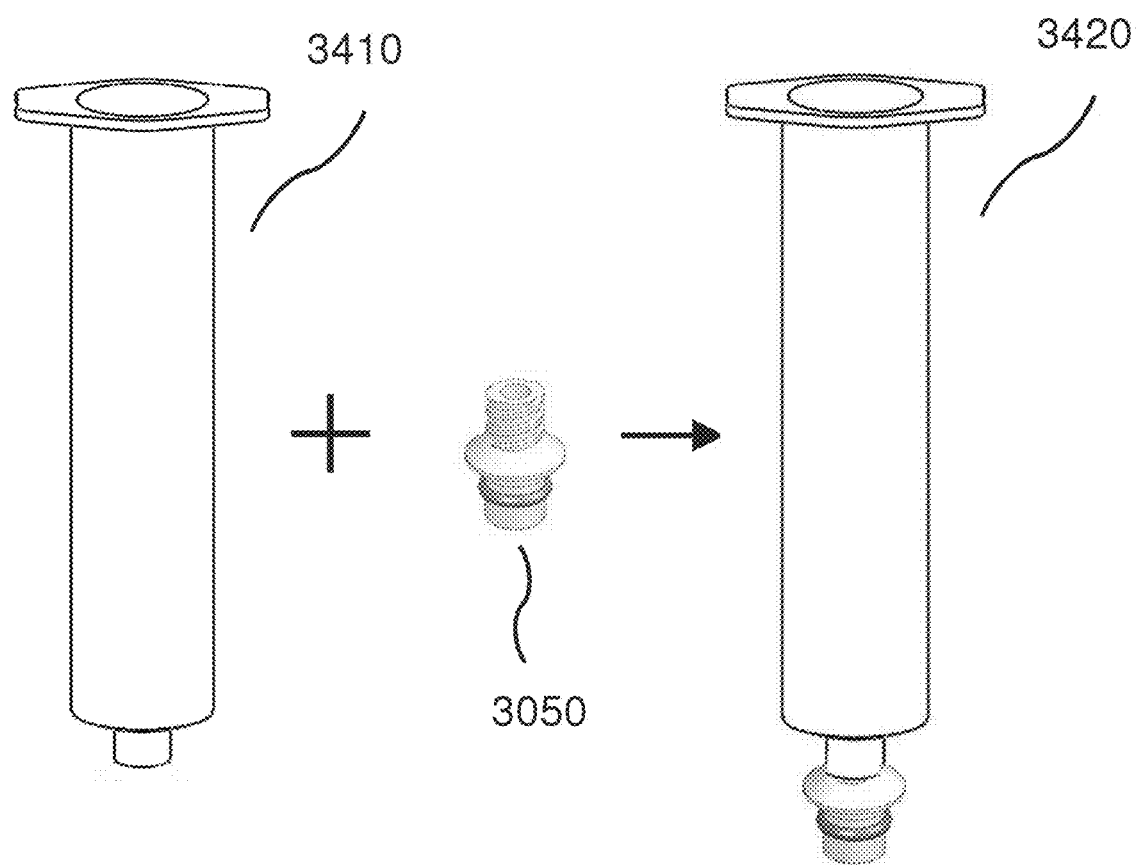
FIG. 23 is an illustration of forming an input container according to an exemplary embodiment of the present invention to be attached to the assembled sample holder illustrated in FIG. 21E using a syringe with Luer lock without the plunger and an adaptor in accordance with exemplary embodiments of the present invention.

The inlet unit 3010 can be combined with inlet adaptor 3050, in FIG. 23, into one piece.

Exemplary embodiments of filter holders described in this application are applicable to most filters and microfilters. Certain exemplary embodiments can be particularly suitable to very thin and strong microfilters such as epoxy-based photo-definable dry film microfilters.

Figure 22A:
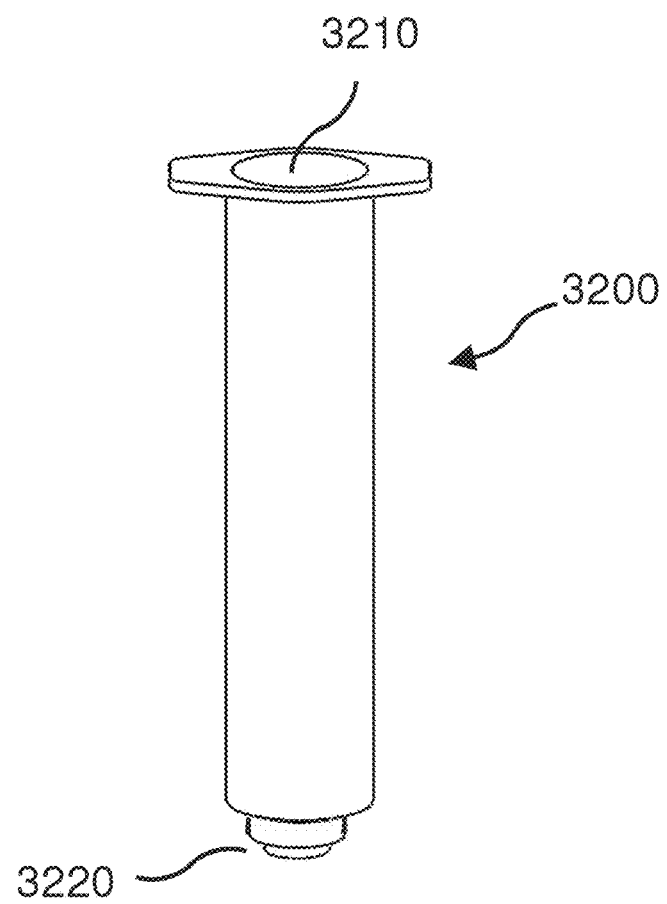
FIGS. 22A-22B illustrate input container options for input liquid sample and reagents to be attached to the assembled sample holder illustrated in FIG. 21E in accordance with exemplary embodiments of the present invention.
Figure 22B:
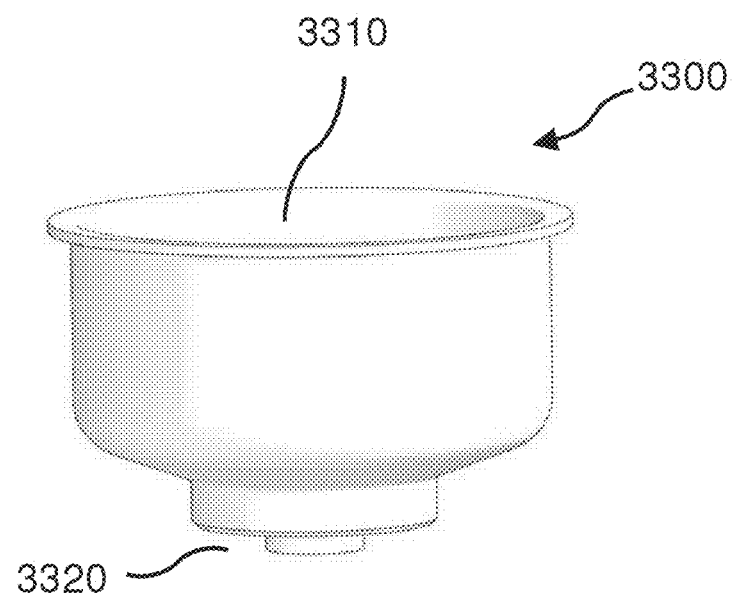

FIGS. 22A-22B show examples of sample input containers for holding the liquid sample and wash buffers. FIG. 22A shows an inlet container 3200 with the shape similar to a syringe with sample inlet opening 3210 and connection to the filter holder 3220. FIG. 22B shows an inlet container 3300 with wider opening 3310 and connection to the filter holder 3320 to allow easy access to the microfilter. FIGS. 22A-22B show examples of sample input container made as one piece.

FIG. 23 shows an example of a sample input container 3420 that can also be constructed out of an off the shelf syringe 3410 without a plunger and an inlet adaptor 3050 with a male Lure-Lock. The inlet adaptor can have various designs as long as it does not leak and it can be easily removed from the filter holder. The shape at the bottom of the sample input containers 3200, 3300, and the inlet adaptor 3050 should have a shape to facilitate tight fit into the inlet unit 3010 on the top of the assembled filter holder 3100 in FIG. 21E. Alternatively, or in combination, an O-ring can be provided to facilitate the tight fit into the inlet unit 3010.

Figure 24:
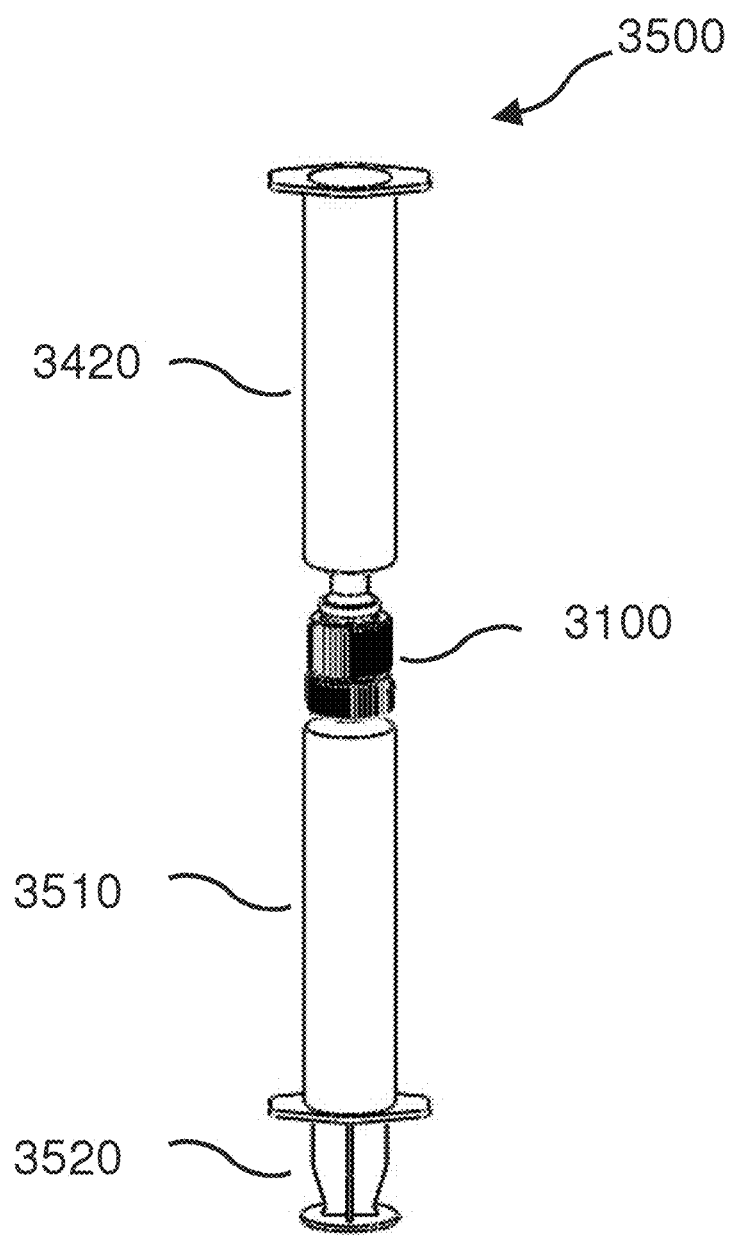
FIG. 24 illustration of the filtration system according to an exemplary embodiment of the present invention to perform the assays incorporating a microfilter inside the filter holder in accordance with exemplary embodiments of the present invention.

The filtration system 3500 can assume the configuration shown in FIG. 24. In the example of this drawing, the input container 3420, constructed as shown in FIG. 23, is connect to the top of the assembled filter holder 3100 from FIG. 21E, and the bottom of the assembled filter holder 3100 shown in FIG. 21E is connected to a waste syringe 3510 with plunger 3520.

Figure 25:
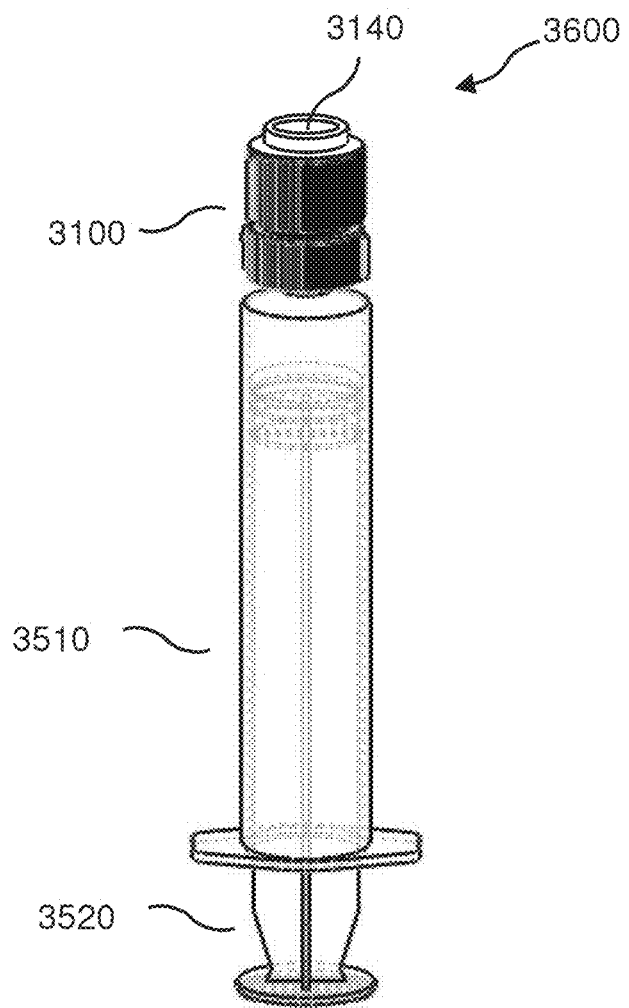
FIG. 25 illustrates the filtration system according to an exemplary embodiment of the present invention to perform some steps of assays with the input container removed in accordance with exemplary embodiments of the present invention.

FIG. 25 shows a filtration system with just the filter holder 3100 and the waste syringe 3510. The opening 3140 allows performance of many assay steps directly on the microfilter.

Figure 26:
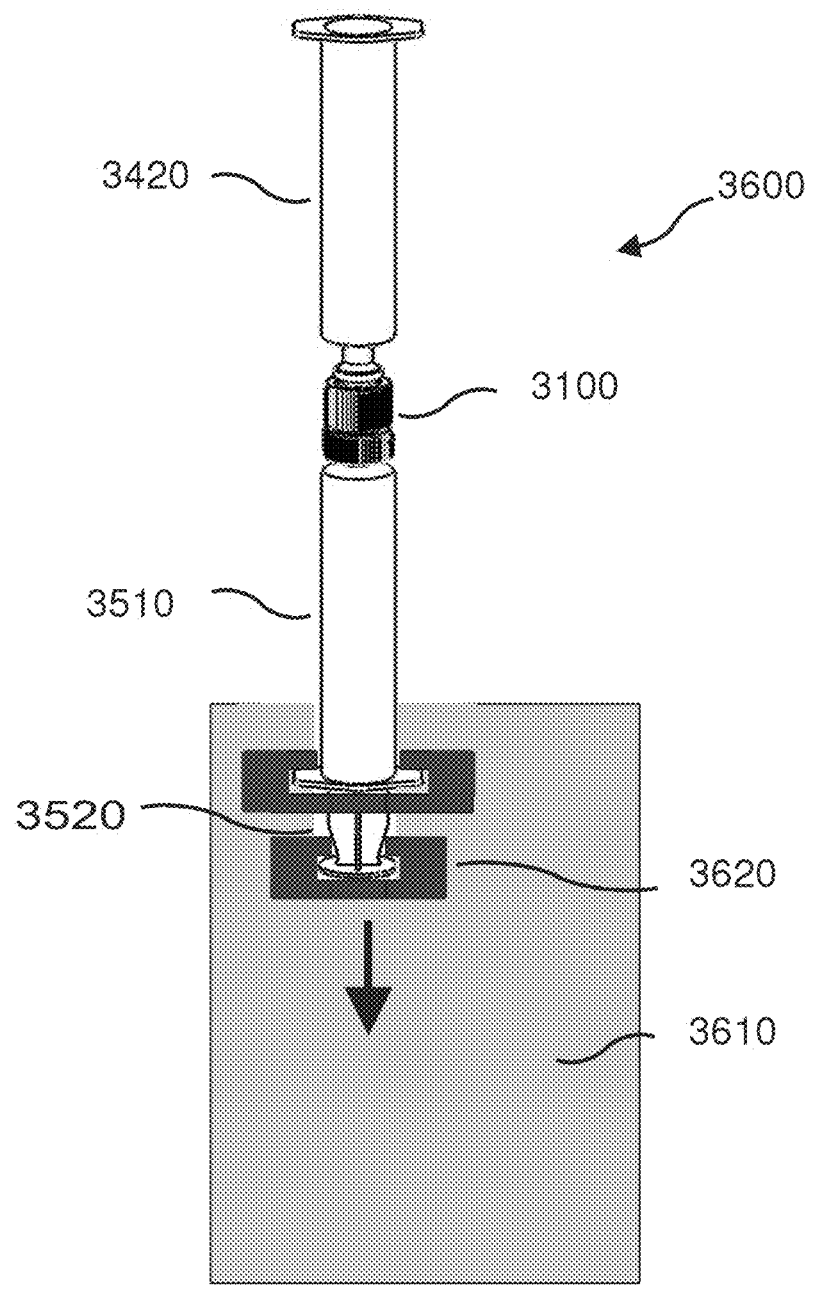
FIG. 26 illustrates the filtration system according to an exemplary embodiment of the present invention using filtration system illustrated in FIG. 24, where the outlet syringe is pulled by a syringe pump.

The filtration can be performed manually by drawing the plunger, but manual operation may not provide consistent speed. The filtration system 3600 using syringe pump 3610 in FIG. 26 can provide more consistent speed for pulling the plunger 3520 by a pusher block 3620. The syringe pump can have just infusion or both infusion and withdrawn functions.

Figure 27A:
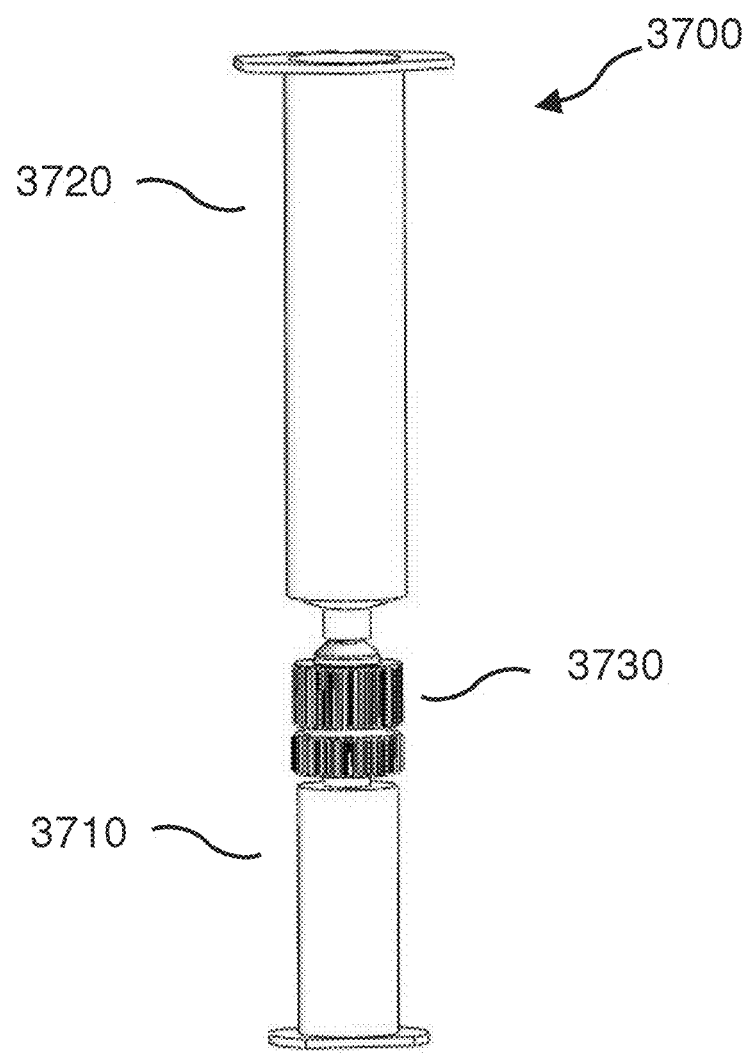
FIGS. 27A-27B shows the configuration according to an exemplary embodiment of the present invention using vacutainer holder to draw the liquid sample from the input sample holder through the filter to a vacutainer.

FIG. 27A shows another exemplary method for drawing blood through the microfilter by connecting a vacutainer holder 3710 to the outlet of the filter holder 3730. When a vacutainer 3740 is inserted into the vacutainer holder 3710, shown in FIG. 27B, the vacuum in the vacutainer will draw the liquid sample into the vacutainer and the microfilter will collect the rare cells.

Figure 28A:
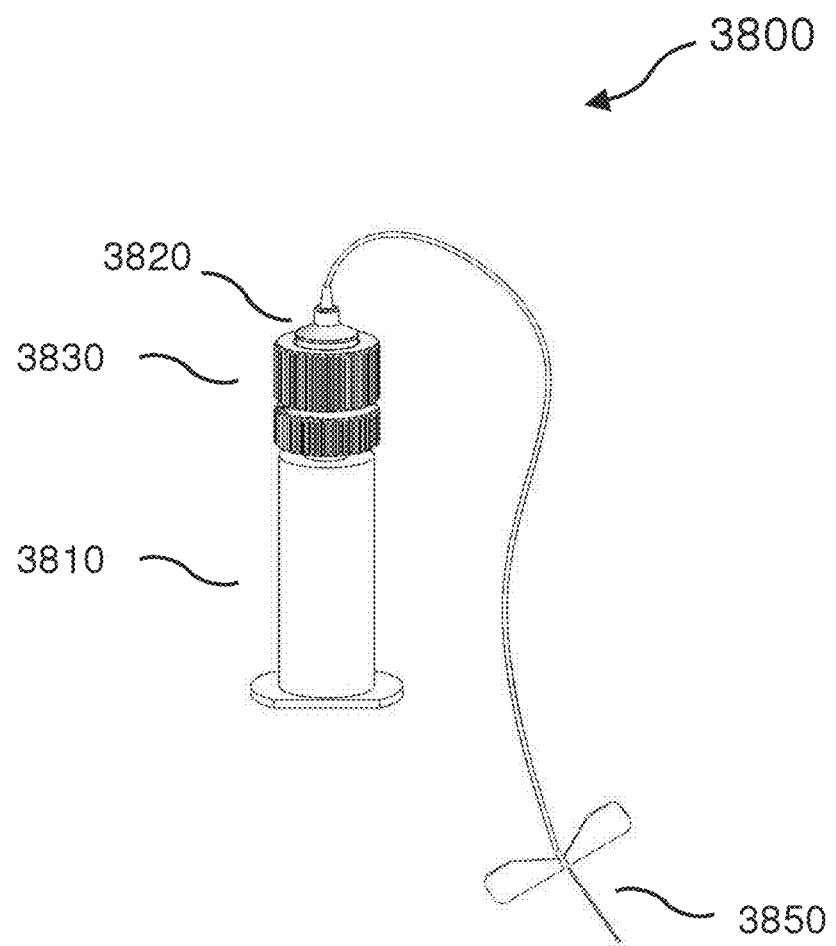
FIGS. 28A-28B shows the configuration according to an exemplary embodiment of the present invention using vacutainer holder to draw the liquid sample from the patient through the filter to a vacutainer. This can be used, for example, to filter circulating tumor cells at time of blood drawn in accordance with embodiments of the present invention.
Figure 28B:
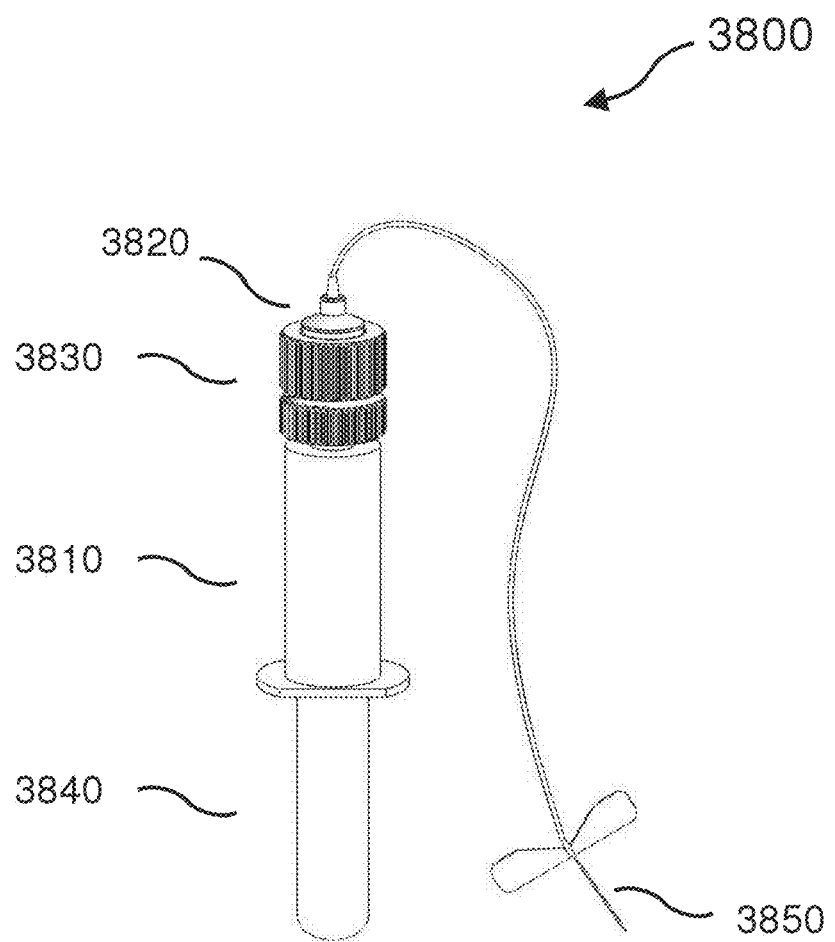

FIG. 28A shows a filtration device 3800 that can perform filtration at the time of getting blood draw. The filtration device combines a filter holder 3830 with the inlet adaptor 3820 and vacutainer holder 3810. A needle 3850 with female Luer-Loc can be attached to the inlet adaptor 3820. FIG. 28B shows a vacutainer 3840 inserted into the vacutainer holder 3810.

Sample Collection and Performing Assays Using the Filtration Devices

The logistics of collecting the sample and shipping the sample to clinical laboratories to perform the rare cell assays according to exemplary embodiments of the present invention are described below with reference to FIGS. 29A-29C.

Figure 29:
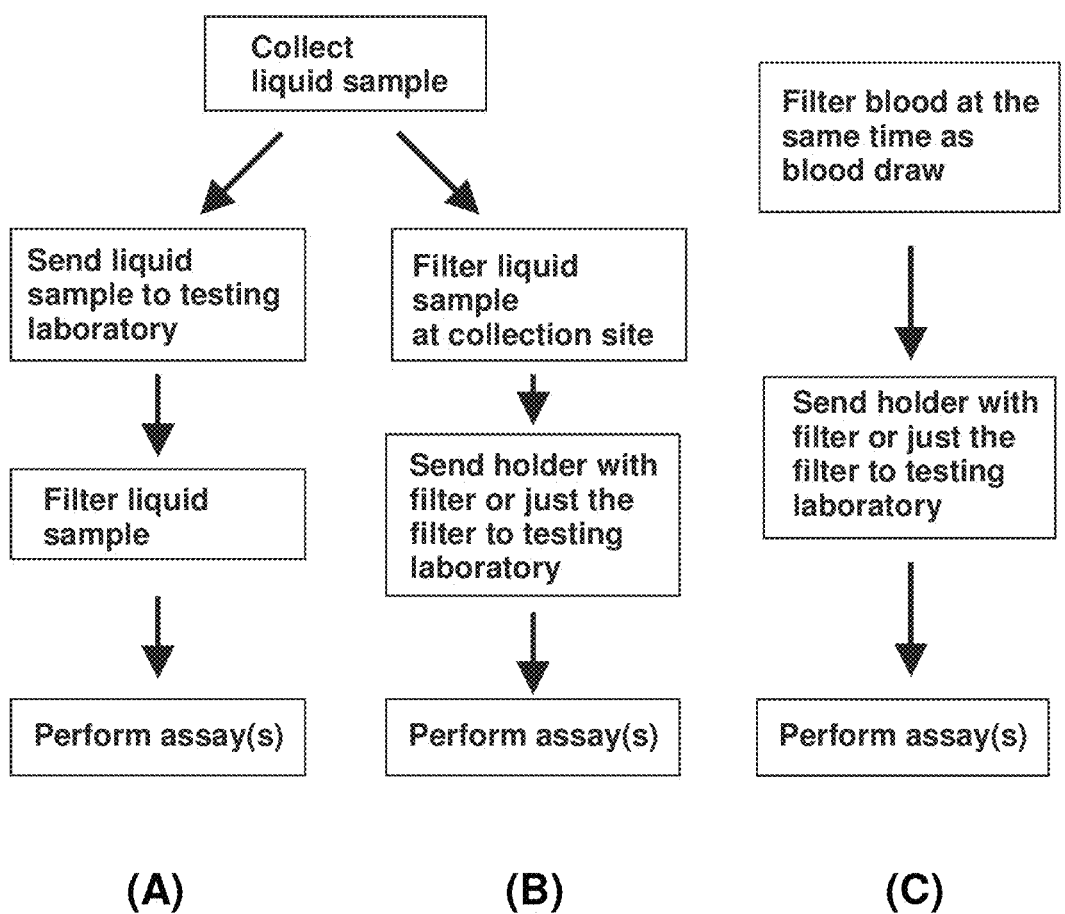
FIGS. 29A-29B are flowcharts illustrating the options in procedures of collecting liquid samples and testing liquid samples in accordance with exemplary embodiments of the present invention.
FIG. 29C is a flowchart illustrating the options to filter rare cells when collecting blood using vacutainers in accordance with exemplary embodiments of the present invention.

FIG. 29A illustrates an example of a method to obtain samples and shipping to clinical laboratories for testing including: (i) collecting body fluid, (ii) sending sample to testing laboratory, (iii) filtering rare cells out of body fluids, and (iv) performing an assay.

Because cells can degrade and blood might form clots and time required for shipping can be 24-48 hours, FIG. 29B describes an alternative method for obtaining samples, and for testing in clinical laboratories including: (i) collecting body fluid, (ii) filtering the rare cells from the body fluid at the collection site. (iii) sending filter holder with microfilter or just the microfilter with captured rare cells to testing laboratory, and (iv) performing the assay in the testing laboratory.

For blood samples, it is also possible to filter the rare cells from blood at the time of drawing the blood using the filtration device 3800 shown in FIG. 29C. After performing a washing step, the filter holder with microfilter or just eh microfilter with captured rare cells can be sent to testing laboratory. Assays will be performed in the testing laboratory.

Microfilter Applications

In exemplary embodiments of the present invention described above, microfilters can be formed from epoxy-based photo-definable dry film having a thickness between 1-500 μm. In certain embodiments, such microfilters can be formed using UV light to expose the dry film (i.e., using UV lithography). In some embodiments, X-rays (i.e., X-ray lithography) may be preferred for exposing relatively thick dry films, for simultaneously exposing multiple stacked dry films, or for exposing resists that require a relatively high dose. In certain embodiments, relatively thick microfilters may provide more structural strength than thinner microfilters, but may also utilize higher pressure during filtration.

As noted above, in certain exemplary embodiments, epoxy-based photo-definable dry films are a preferred material from which to form microfilters in accordance with embodiments of the present invention. In some embodiments, properties of epoxy-based photo-definable dry film that make it a suitable material from which to form microfilters for medical diagnostic applications are that it is photo-definable by UV light, it is clear, it has a high tensile strength of 75 Mpa, it can be laminated to itself, it can be directly coated on a substrate, and it has no auto-fluorescence in the visible wavelengths. In addition, while the processes described above in accordance with embodiments of the present invention may be used to form microfilters, the processes described above may also be used to manufacture other kinds of free-standing patterned polymeric films.

Microfilters formed in accordance with exemplary embodiments of the present invention have many possible applications. In some embodiments, exemplary applications for such microfilters include medical applications, water filtration applications, beer and wine filtration applications, pathogen detection applications, etc.

Figure 30A:
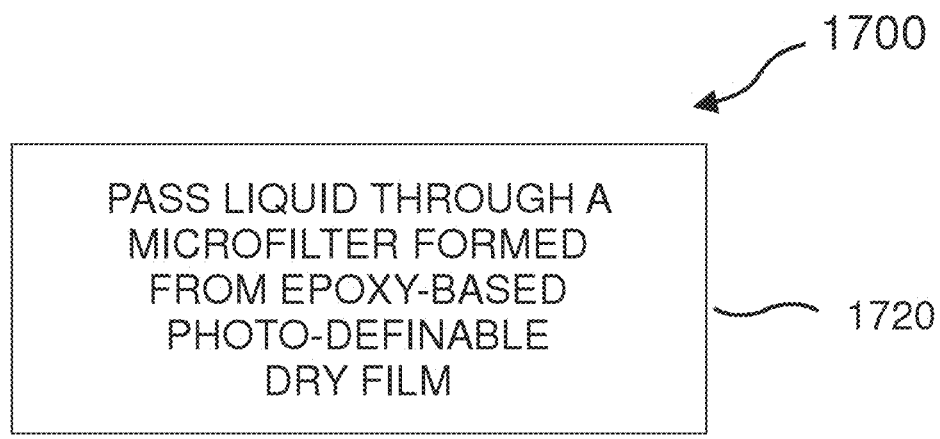
FIG. 30A is a flowchart illustrating a filtration process using a microfilter in accordance with exemplary embodiments of the present invention.

FIG. 30A is a flowchart illustrating a filtration process 1700 using a microfilter in accordance with exemplary embodiments of the present invention. At block 1720 of FIG. 30A, a liquid may be passed through a microfilter formed from a layer of epoxy-based photo-definable dry film, in accordance with any one of the embodiments described above, having a plurality of apertures. In certain embodiments, the liquid may be pushed through the microfilter. In other embodiments, the liquid may be drawn through the microfilter. The draw can be produced by a syringe or by vacuum. In some embodiments, the liquid may be passed back and forth through the microfilter one or more times. In some embodiments, the particulates retained on the microfilters may be backwashed using appropriate liquid.

In certain exemplary embodiments, the process illustrated in FIG. 30A may be used to perform an assay using the microfilter. In certain embodiments, the process may be used to filter cells, such as CTCs, from a solution including a patient's bodily fluid. This can be accomplished using vacutainer as shown in FIG. 28A-28B, or by placing the filter on a support above a vacuum pump.

Figure 30B:
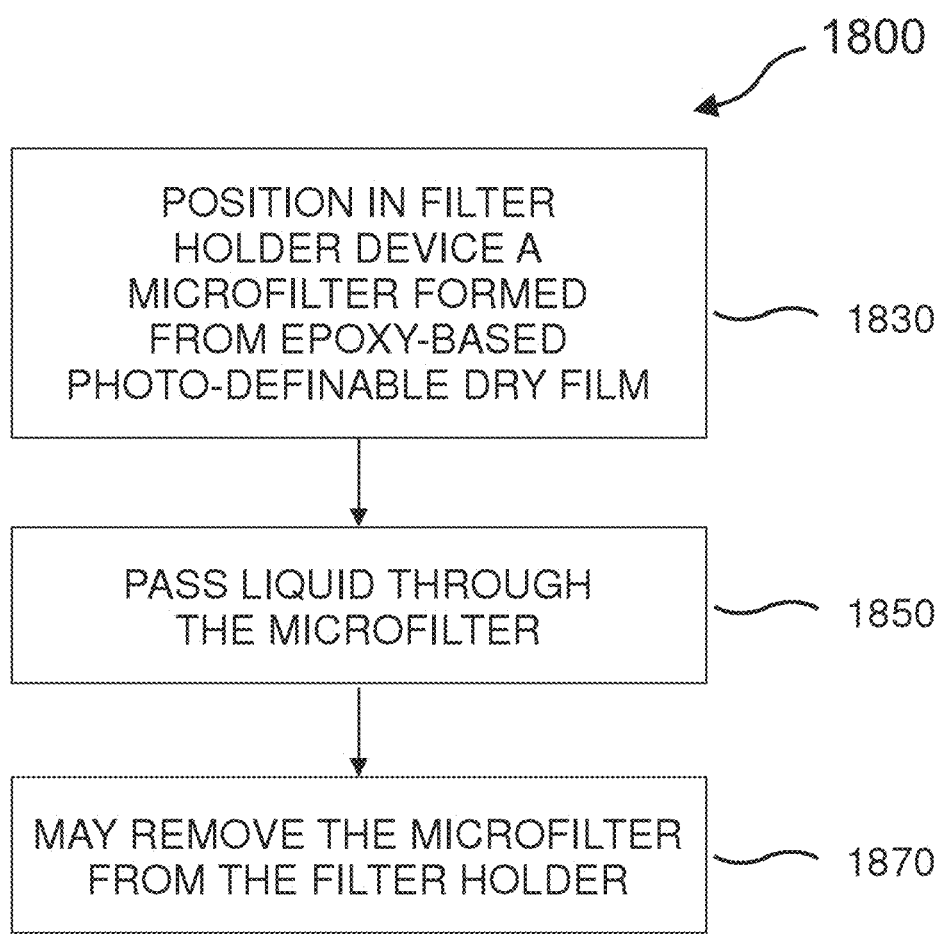
FIG. 30B is a flowchart illustrating a filtration process using a microfilter in accordance with exemplary embodiments of the present invention.

FIG. 30B is a flowchart illustrating a filtration process 1800 using a microfilter in accordance with exemplary embodiments of the present invention. At block 1830 of FIG. 30B, a microfilter formed from a layer of epoxy-based photo-definable dry film, in accordance with any one of the embodiments described above, is positioned in a filter holder. In certain embodiments, the filter holder includes an inlet, an outlet, and securely holds the microfilter around the edges of the filter. In some embodiments, a liquid may be input into the filter holder through the inlet. At block 1850, the liquid is passed through the microfilter. In certain embodiments, the liquid is a bodily fluid or a solution including a bodily fluid. In certain embodiments, the liquid is drawn through the microfilter by applying negative pressure at the outlet of the filter holder such that all or substantially all of the liquid is drawn through the pores of the microfilter. In other embodiments, the liquid is pushed through the microfilter. At block 1870, the microfilter may also be removed from the filter holder. For microscope imaging, the microfilter may be placed on a glass slide.

Figure 30C:
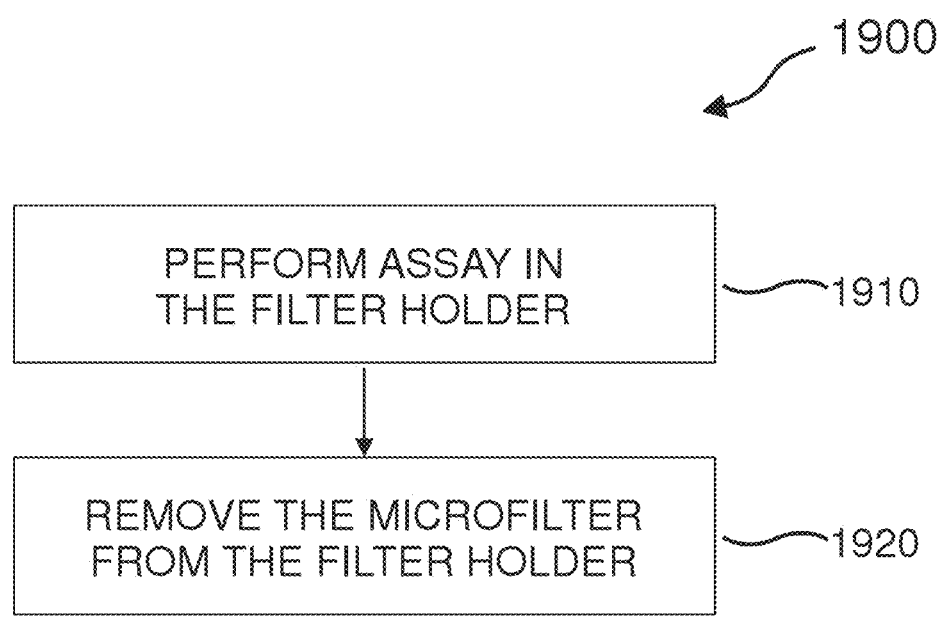
FIG. 30C is a flowchart illustrating the process of performing some types of the assays of the cells collected on the microfilter in the filter holder in accordance with exemplary embodiments of the present invention.

FIG. 30C is a flowchart 1900 illustrating examples for performing some types of assays in the filter holder 1910. After the assay, the filter can be removed from the filter holder 1920 for analysis.

Enzymatic activity assay, histopathology staining (colorimatric staining), and immunofluorescent staining for applications such as determination of biomarker expression, EPISPOT and enumeration, can follow the flow chart steps in FIG. 30C after step shown in FIG. 30B. These assays can be performed in a filter holder as described. These assays can also be performed on glass slide, or plate after removing the microfilter from the filter holder follow the flow chart shown in FIG. 30A or 30B.

Nucleic acid assays, sequencing, fluorescence in situ hybridization (FISH), mRNA in situ hybridization, and culture require removing the microfilter with captured rare cells from the filter holder and perform the assays in each of their own appropriate ways as shown in flow chart of FIG. 30A or 30B.

In the exemplary flow chart of FIG. 30B, the protocol to isolate cells is as follows using the syringe pump:
1. Assemble the microfilter in the filter holder as shown in FIGS. 21A-21E;
2. Mount a waste syringe 3510 to a syringe pump 3610;
3. Attach the assembled filter holder 3100 on to the waste syringe 3510;
4. Attach the inlet container 3420 (FIG. 22A, 22B or 23) on top of the filter holder 3100, and the complete assemble looks like FIG. 26;
5. Place liquid sample into the input container 3420;
6. Using negative pressure, suck the liquid sample through the microfilter into the waste syringe.
7. To perform wash step, place wash buffer into the input container 3420, and suck the wash buffer through the microfilter into the outlet syringe. Perform wash a few times.
8. Remove the input container 3420 and the filtration system looks like FIG. 25.
9. Open the filter holder to retrieve the microfilter.

The syringe pump can be operated manually or can be automated.

The filtration can be performed manually. To perform the assay manually, skip step 2. At the start, complete assembled system looks like FIG. 24.

The filter holder 3100 can also be placed on a stopper on a filter flask connect to a vacuum pump with the inlet container 3420. The liquid sample and the wash buffer can be placed into the inlet container 3420. The vacuum pump turned on to draw the liquid through the filter. If the inlet container is not used, the liquid sample and the wash buffer can be pipette into the reaction well 3010 while the vacuum is on.

Figure 27B:
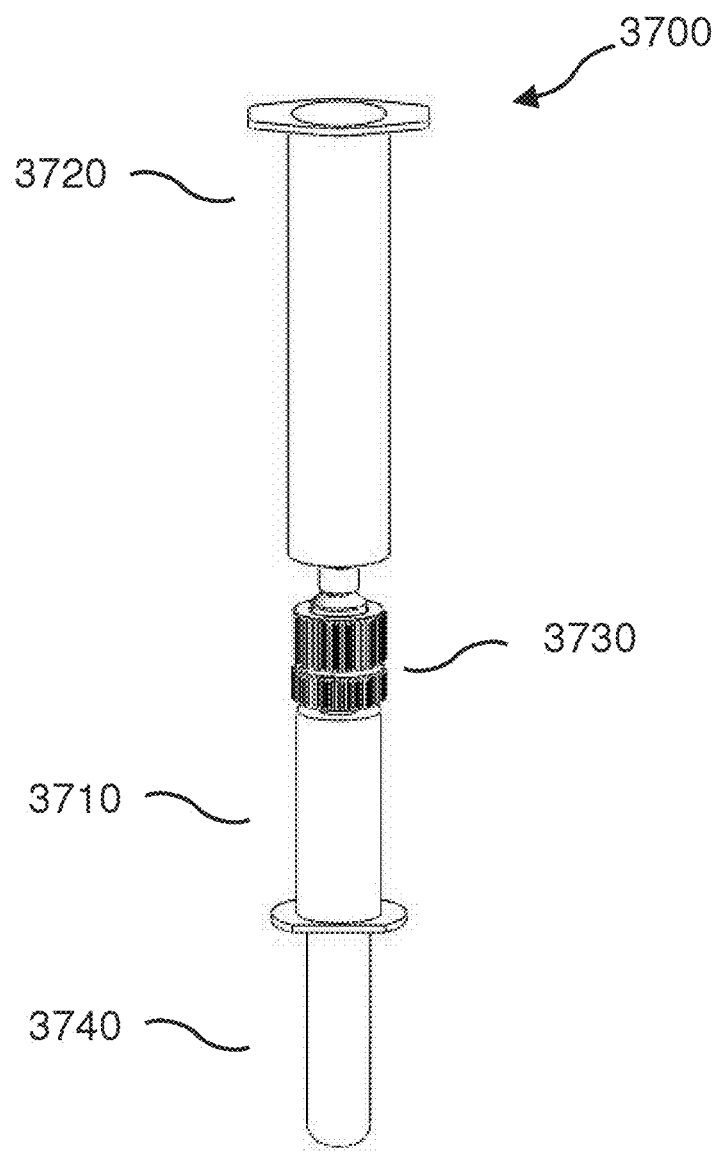

The filtration can be performed using the vacutainer systems 3700 as shown in FIG. 27A. The steps are:
1. Assemble the microfilter in the filter holder as shown in FIGS. 21A-21E;
2. Mount a vacutainer holder to the outlet of the filter holder 3730 as shown in FIG. 27A.
3. Attach the inlet container 3720 (FIG. 22A, 22B or 23) on top of the filter holder 3730, and the complete assemble looks like FIG. 27A;
4. Place liquid sample into the input container 3720;
5. Insert vacutainer 3740 into the vacutainer holder 3710, as shown in FIG. 27B.
6. To perform washing step, place wash buffer into the input container 3720.
7. Install a fresh vacutainer 3740 into the vacutainer holder 3710 to perform the wash.
8. Further processing of the cells collect on the microfilter as needed, or open the filter holder to retrieve the microfilter.

The filtration can be performed at the time of blood draw using the vacutainer systems 3800 as shown in FIG. 28A. The steps are:
1. Assemble the microfilter in the filter holder as shown in FIGS. 21A-21E;
2. Mount a vacutainer holder to the outlet of the filter holder as shown in FIG. 28A.
3. Attach a needle 3850 with female Luer-Loc to the inlet adaptor 3820.
4. Insert needle into the vein of the patient.
5. Insert vacutainer 3840 into the vacutainer holder 3810, as shown in FIG. 28B.
6. Remove vacutainer 3840 after draw.
7. Remove the needle from the patient's vein.
8. Remove the needle from the filter holder, and install an input container 3720 as shown in FIG. 27A.
9. To perform the washing step, place wash buffer into the input container 3720.
10. Install a fresh vacutainer 3740 into the vacutainer holder 3710 to perform the wash, as shown in FIG. 27B or insert the syringe into the outlet of the filter holder as shown in FIG. 23.
11. Further processing of the cells collect on the microfilter as needed, or open the filter holder to retrieve the microfilter.

The filter with cells attached can be used for various assays and analysis.

FIG. 30C shows that many assay steps can be performed in the filter holder after the steps in the flow chart of FIGS. 30A-30B. The details of the assay steps can vary depending on the assay. This is performed using the configuration shown in FIG. 25. The steps will vary depending on the assay. The general steps are described below.
1. Incubation: Place reagents into the reservoir 3140 above the filter and incubate. The incubation of with reagents above the microfilter in the filter holder is possible because the apoxy-based photo-definable dry film microfilter is hydrophobic. Reagents will not leak through the microfilter.
2. Wash: For small amount of wash buffers after the incubation, wash buffer can be placed directly into the reservoir 3140 and sucked out by negative pressure. This can be repeated. When larger volumes of washing buffers are required, place the input container back on the filter holder to form the system shown in FIG. 24 and perform washing step by sucking out the wash buffer placed into the input container.
3. Anytime the outlet syringe becomes full, replace with a new outlet syringe.
4. When the assay is completed, unassembled the filter holder and take out the microfilter and place it on a glass slide, plate reader or other appropriate device for image analysis.

Nucleic acid assays and sequencing are suited for performing the assay from the lysed cells. The conceptual protocol follows the steps of collecting the cells on the microfilter. After taking the microfilter out of the filter holder, place the microfilter containing rare cells i6 an Appendorf centrifugation tube with lysis buffer. The rest of the steps for the nucleic acid assays are the same as common samples.

For culturing the rare cells, the conceptual protocol follows the steps of collecting the cells on the microfilter. After taking the microfilter out of the filter holder, place the microfilter containing rare cells in culture medium. Cells can also be backwashed out of the filter into culture medium. In some situations the rare cells need to be removed from the microfilter and inject into an animal such as mice.

Analysis of Microfiltered Cells

In some embodiments, the particulates retained on the microfilter may then be subject to processing and or analysis to analyze any cells or other materials, substances, etc. collected by the microfilter. The analysis may be performed in the filter holder device or microfiltration chip. The analysis may also be performed outside the filter holder after the microfilter is removed from the filter holder. Exemplary applications of this process in accordance with embodiments of the present invention will be described below.

In certain embodiments, a microfilter formed from a layer of epoxy-based photo-definable dry film in accordance with any one of the embodiments described above may be used for medical diagnostics and/or prognostics. In certain embodiments, the microfilter may be used to collect certain types of cells from bodily fluids based on cell size. In some embodiments, the microfilter can be used for isolating and detecting rare cells from a biological sample containing other types of cells. In some embodiments, the microfilter can be used to filter a fluid sample, and the collected cells can be used in a downstream processes such as cell identification, enumeration (cell counting), characterization of the collected cells, culturing the collected cells, separating the cells into individual cells or groups of cells, or use the of cells in other ways. The final enriched target cells can be subjected to a variety of characterization and manipulations, such as staining, immunofluorescence of markers, cell counting, DNA, mRNA, microRNA analysis, fluorescence in-situ hybridization (FISH), immunohistochemistry, flow cytometry, immunocytochemistry, image analysis, enzymatic assays, gene expression profiling analysis, sequencing, efficacy tests of therapeutics, culturing of enriched cells, and therapeutic use of enriched rare cells. In addition, depleted plasma protein and white blood cells can be optionally recovered and subjected to other analysis, such as inflammation studies, gene expression profiling, etc.

In certain embodiments, the microfilter can be held in a filter holder for medical diagnostics and/or prognostics. In some embodiments, the filter holder may include a built in support for the microfilter. In certain embodiments, the filter holder may have gasket above and below the filter. In some embodiments, the microfilter may be used to collect circulating tumor cells (CTCs) in blood. In such embodiments, a blood sample, typically in the range of 1-10 ml, is taken from a patient. The blood sample is then drawn through the microfilter by applying negative pressure, such as a sucking force. In certain embodiments, the blood is pulled through the microfilter via an outlet. In some embodiments, passing the blood through the filter by pushing can cause cell rupture except at very low pressure or low speed.

In certain embodiments, most cells having a dimension larger than the width of one or more pores of the microfilter are retained. Most white blood cells are deformable and can pass through pores having a smaller width than a dimension of the white blood cell. In certain embodiments, nearly no red blood cells are retained on the microfilter. In some embodiments, the microfilter may include pores 7-8 μm in diameter for enriching circulating tumor cells and fetal cells; however, the microfilter pore size and shape can be varied for these applications as well.

In some embodiments, CTCs collected by the microfilter can be enumerated on the microfilter. In one experiment conducted to determine the capture efficiency of a microfilter, tumor cell lines were used. The microfilter used to demonstrate filtration efficiency was a microfilter having a 7-8 micron diameter pores separated by 20 microns and arranged within a 9 mm diameter area. The microfilter was placed into a filter holder. A prestained MCF-7 cell line was spiked into 7.5 ml of whole blood. To capture live CTCs, the blood was diluted 1:1 with a buffer solution. One exemplary buffer solution is phosphate buffered saline (PBS). Another exemplary buffer solution is a mild fixation buffer to make the CTCs slightly more rigid. The liquid sample was drawn through the microfilter using negative pressure at approximately 10 ml/min. Afterwards, the filter was washed twice in a buffer solution. The microfilter was removed from the holder and mounted onto a microscope slide to be counted. The recovery rate of live MCF-7 cells was 85%±3%. If the blood is mildly fixed, the capture efficiency of MCT-7 cells increases to 98%±2%.

In certain embodiments, collected CTCs can be subjected to a variety of analyses and manipulations, such as immunofluorescence, genetic characterization and molecular phenotyping, fluorescence in-situ hybridization (FISH), mRNA FISH, in-situ hybridization (ISH), mRNA ISH, immunohistochemistry (IHC), flow cytometry, immunocytochemistry, colorimetric staining, histopathological staining (for example, hematoxylin and eosin staining), image analysis, epithelial immunospot (EPISPOT), enzymatic assays, gene expression profiling analysis, efficacy tests of therapeutics, culturing of enriched cells, and therapeutic use of enriched rare cells. In addition, in some embodiments, depleted plasma protein and white blood cells can be optionally recovered, and subjected to other analysis such as inflammation studies, gene expression profiling, etc.

In certain embodiments, CTCs collected from blood can be stained to identify them as potential tumor cells and not blood cells. It is possible to identify the CTCs by morphology using colorimetric staining. Other methods are based on fluorescence staining. Some typical fluorescence staining methods to identify the cells as tumor cells use DAPI to identify the nucleus and us cytokeratins 8, 18 and 19 conjugated to a fluorescent dye to identify them as epithelial cell. Since normal epithelial cells are not fund in blood, epithelial cells found in blood are accepted as tumor cells. CD45 antibody is used to identify white blood cells, eliminating the blood cells retained on the microfilter as CTCs. It is commonly accepted that a cell from blood that is DAPI positive, CK 8, 18, and 19 positive and CD45 negative to be a CTC. Other markers, such as EpCAM, MUC-1, and others) can be included to further provide specificity and increase of fluorescence signal.

In certain embodiments, captured CTCs are stained to specifically identify the origin of the tumor cells, such as breast, prostate, colon, etc. For example, PSA marker on the cell would identify its origin as prostate. For each cancer, specific markers can be found either on the surface or inside the cells.

In certain embodiments, captured CTCs can be characterized to determine if it contains specific mutations of the DNA. This can be identified by for DNA, mRNA, and microRNA expression by PCR, by sequencing, or by antibodies, ligends, aptamers and others that recognize the mutated proteins.

In certain embodiments, captured CTCs can be characterized to determine over-expression of genes. Sometimes the number of copies of a gene is more than it should be for each cell. When there are more copies of the gene, it produces more copies of mRNA, which in turn produces more copies of the protein. The number of copies of the gene can be determined by FISH or by ISH, The amount of mRNA produced can be obtained by PCR, mRNA FISH and mRNA ISH. The amount of proteins produced can be determined by immunofluorescent stains for that protein. Cells over-expression a marker will stain brighter for that marker than normal tissue. One example of over expression is HER-2 in some subtypes of breast cancer.

In certain embodiments, captured CTCs can be characterized to determine if they are viable cells.

In certain embodiments, captured CTCs can be determined if they are viable. Viability can be determined by trypan blue staining, or culture.

In certain embodiments, captured CTCs can be determined if they are stem cells. They can be stained for stem cell marker phenotype (CD44$^+$/CD24$^{-/low}$ or CK19$^+$/MUC-1$^-$)

In certain embodiments, viable CTCs may be captured by microfilter coated by analyte recognition elements, such as antibodies, ligends, aptamers, etc. The analytes of interest are to be secreted by the CTC. A secondary analyte recognition element can be used to produce a detectable signal if the analyte is produced by the CTC. The signal may be produced by fluorescent dyes. The concept is similar to EPISPOT.

In certain embodiments, captured live CTCs can be cultured directly on the microfilter to increase the number of CTCs and to evaluate the characteristics of CTCs. In other embodiments, the CTCs can be backwashed from the microfilter prior to culturing or sorting.

In other embodiments, a microfilter formed from a layer of epoxy-based photo-definable dry film in accordance with embodiments of the present invention may be used in therapeutic applications in which circulating tumor cells are removed from the blood of cancer patients. Circulating tumor cells are the cause of cancer spreading from the original site to other locations such as brain, lung and liver. Most carcinoma cancer patients die from the metastatic cancer. In certain embodiments, microfiltration using a microfilter formed in accordance with embodiments of the invention is a suitable method for removing circulating tumor cells from the blood stream of a patient because the filtration speed is fast and microfilters retain very little white blood cells and almost no red blood cells when used to filter blood.

Microfiltration for circulating tumor cells in blood can provide a large array of diagnostic, prognostic and research applications. For collecting circulating tumor cells, previous research reports utilized track etch filters with random pore locations with some overlapping pores and not straight pores, and microfilters with orderly arranged pores produced by reactive ion etching. In certain embodiments of the present invention, microfilters formed from epoxy-based photo-definable dry film and having precisely arranged pores are used to collect circulating tumor cells in blood.

One exemplary application of a microfilter formed in accordance with embodiments of the present invention is to monitor effectiveness of treatment by counting the number of CTCs collected in the blood. Large number of CTC per ml of blood can indicate short lifespan. The change of CTCs per ml of blood can indicate whether treatment is working or not. If the number of CTCs is decreasing, it indicates the treatment is having an effect. In contrast if the number of CTCs is increasing, it indicates the treatment is ineffective.

One exemplary application of a microfilter formed in accordance with embodiments of the present invention is using the microfilter for capturing cells and subsequently culturing the cells in the filter holder, or culturing the cells after back flushing the cells off the microfilter. Various drugs can be applied to the cultured CTCs can be used to evaluate drug efficacy to determine the best treatment for the patients.

One exemplary application of a microfilter formed in accordance with embodiments of the present invention is to determine gene mutation in CTCs to determine the appropriate drug.

One exemplary application of a microfilter formed in accordance with embodiments of the present invention is to determine over expression of a marker when there is drug to treat tumors with the over expression One exemplary application of a microfilter formed in accordance with embodiments of the present invention is to determine if the cancer is returning after remission. If the number of CTCs become more than five from 7.5 ml of blood and the CTC count is increasing in time, then the cancer is returning.

Another exemplary application of a microfilter manufactured in accordance with embodiments of the present invention is capturing circulating endothelial cells. Endothelial cells in the peripheral blood provides information about various medical conditions.

Another exemplary application of a microfilter manufactured in accordance with embodiments of the present invention is capturing circulating fetal cells in a mother's blood during weeks 11-12 weeks of pregnancy. Such fetal cells may include primitive fetal nucleated red blood cells. Fetal cells circulating in the peripheral blood of pregnant women are a potential target for noninvasive genetic analyses. They include epithelial (trophoblastic) cells, which are 14-60 µm in diameter, larger than peripheral blood leukocytes. Enrichment of circulating fetal cells followed by genetic diagnostic can be used for noninvasive prenatal diagnosis of genetic disorders using PCR analysis of a DNA target or fluorescence in situ hybridization (FISH) analysis of genes.

Another exemplary application of a microfilter manufactured in accordance with embodiments of the present invention is collecting or enriching stromal cells, mesenchymal cells, endothelial cells, epithelial cells, stem cells, non-hematopoietic cells, etc. from a blood sample, collecting tumor or pathogenic cells in urine, and collecting tumor cells in spinal and cerebral fluids. Another exemplary application is using the microfilter to collect tumor cells in spinal fluids. Another exemplary application is using the microfilter to capture analytes bound to latex beads or antigen caused particle agglutination whereby the analyte coated bead or agglutinated clusters are captured on the membrane surface.

Another exemplary application of a microfilter formed in accordance with embodiments of the present invention is for erythrocyte deformability testing. Red blood cells are highly flexible cells that will readily change their shape to pass through pores. In some diseases, such as sickle cell anemia, diabetes, sepsis, and some cardiovascular conditions, the cells become rigid and can no longer pass through small pores. Healthy red cells are typically 7.5 µm and will easily pass through a 3 µm pore membrane, whereas a cell with one of these disease states will not. In the deformability test, a microfilter having 5 µm apertures is used as a screening barrier. A blood sample is applied and the membrane is placed under a constant vacuum. The filtration rate of the cells is then measured, and a decreased rate of filtration suggests decreased deformability.

Another exemplary application of a microfilter formed in accordance with embodiments of the present invention is leukocyte/Red blood cell separation. Blood cell populations enriched for leukocytes (white blood cells) are often desired for use in research or therapy. Typical sources of leukocytes include whole peripheral blood, leukopheresis or apheresis product, or other less common sources, such as umbilical cord blood. Red blood cells in blood can be lysed. Then the blood is caused to flow through the microfilter with small pores to keep the leukocytes. Another exemplary application is using the microfilter for chemotaxis applications. Membranes are used in the study of white blood cell reactions to toxins, to determine the natural immunity in whole blood. Since immunity is transferable, this assay is used in the development of vaccines and drugs on white blood cells. Another exemplary application is using the microfilter for blood filtration and/or blood transfusion. In such applications, microfilters can be used to remove large emboli, platelet aggregates, and other debris.

Additionally, arrays of precision micro-pores can be fabricated in rolls of polymer resists in accordance with embodiments of the invention described above. Such arrays may be used for applications for which wafer-sized microfilters are not suitable. Examples of such applications include water filtration, kidney dialysis, etc.

While various embodiments have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents. The present embodiments are, therefore, to be considered in all respects as illustrative and not restrictive. Additionally, it will be appreciated that any features, components, elements, etc., described above in relation to different exemplary embodiments may be implemented together.

We claim:

1. A filter holder comprising:
   an inlet unit including a first volume and a first opening to said first volume; and
   an outlet unit including a second volume for accommodating a filter structure removably configured therein, and a second opening to said second volume,
   wherein said first and second openings are at opposite ends when said inlet unit is secured to said outlet unit, and said filter structure is exposed for observation of filtered substance collected on said filter structure and for performing an assay on said filtered substance within said first volume through said first opening.

2. The filter holder of claim 1, further comprising a nut configured to removably attach to said outlet unit and removably secure said inlet unit to said outlet unit,
   wherein said first opening is exposed through said nut.

3. The filter holder of claim 1, wherein said first volume accommodates a reagent therein when placed therein.

4. The filter holder of claim 1, further comprising a first gasket disposed in said second volume with respect to said filter structure,
   wherein said gasket includes a third opening aligned with said first opening and said second opening.

5. The filter holder of claim 4, wherein:
   said second volume includes a substantially circular seat for accommodating said gasket;
   a diameter of said filter structure is essentially equal to an outer diameter of said gasket and an outer diameter of said seat; and
   said inlet unit, said gasket and said filter structure are removably secured with said outlet unit by said nut, whereby said filter structure remains flat and experiences compression to form a tight seal with said inlet unit and said outlet unit, without experiencing a twisting force.

6. The filter holder of claim 1, further comprising a plurality of gaskets disposed in said second volume with respect to said filter structure,
   wherein each of said gaskets includes a gasket opening aligned with said first opening and said second opening.

7. The filter holder of claim 6, wherein at least one of said gaskets is configured between said inlet unit and said filter structure, or between said filter structure and said outlet unit.

8. The filter holder of claim 6, wherein said filter structure is configured between at least two of said gaskets.

9. The filter holder of claim 6, wherein said filter structure comprises one or more essentially flat layers.

10. The filter holder of claim 1, wherein said outlet unit is configured to facilitate attachment of an outlet container at said second opening.

11. The filter holder of claim 1, wherein said second opening of said outlet unit comprises an outlet output for attachment of a male or female input connection of a syringe or vacutainer holder.

12. The filter holder of claim 1, wherein said inlet unit further comprises an inlet adapter including an adapter input for attachment of a sample input container thereto and an adapter output in communication with said first volume allowing passage of at least a portion of a sample material from said sample input container to said first volume.

13. The filter holder of claim 2, wherein said inlet unit further comprises an inlet adapter including an adapter input for attachment of a sample input container thereto and an adapter output in communication with said first volume allowing passage of at least a portion of a sample material from said sample input container to said first volume,
   wherein said adapter input extends through said nut whereby said first opening is exposed through said nut.

14. The filter holder of claim 12, wherein said sample input container comprises a syringe having a male or a female output connection, and said adapter input is configured for attachment of said male or female output connection of said syringe.

15. The filter holder of claim 1, wherein:
   said inlet unit includes a fourth opening to said first volume diametrically opposite and aligned with said first opening;
   said outlet unit includes a fifth opening to said second volume diametrically opposite and aligned with said second opening; and
   said fourth opening essentially overlaps said fifth opening when said inlet unit and said outlet unit are secured.

16. The filter holder of claim 15, wherein said filter structure is disposed above said fifth opening, and
   said filter structure is exposed for said observation and said performing said assay in said first volume via said first and fourth openings when said inlet unit and said outlet unit are secured.

17. The filter holder of claim 15, wherein said filter structure is removably positioned in said second volume above said fifth opening.

18. The filter holder of claim 1, wherein:
   said inlet unit comprises essentially cylindrical first inner surface and first outer surface; and
   said outlet unit comprises essentially cylindrical second inner surface and second outer surface.

19. The filter holder of claim 18, wherein at least one of:
   said first inner surface and first outer surface are concentric; and
   said second inner surface and second outer surface are concentric.

20. The filter holder of claim 18, wherein at least one of:
   said first inner surface and said second inner surface are essentially concentric when said inlet unit and said outlet unit are secured; and said first outer surface and said second outer surface are essentially concentric when said inlet unit and said outlet unit are secured.

21. The filter holder of claim 18, wherein at least one of:
said first inner surface and said second inner surface comprises at least one essentially equal cross sectional diameter; and
said first outer surface and said second outer surface comprises at least one essentially equal cross sectional diameter.

22. The filter holder of any of claim 1, wherein said filter structure comprises:
a polymer layer formed from epoxy-based photo-definable material; and
a plurality of apertures each extending through the polymer layer.

23. A method of performing an assay comprising:
positioning a microfilter into a filter folder as claimed in any of claims 1 through 21
selectively placing a filter into an outlet unit, the outlet unit including a seat for removably accommodating said filter or a gasket, and a second opening therethrough to facilitate attachment of an output container thereto;
removably placing said gasket onto said filter or under said filter, wherein a diameter of said filter is essentially equal to an outer diameter of said gasket and an outer diameter of said seat;
removably placing an inlet unit onto said filter when said gasket is under said filter, or removably placing said inlet unit onto said gasket when said gasket is on said filter, said inlet unit including a first opening opposite to said second opening;
installing a nut onto said outlet unit to removably secure said inlet unit, said filter, and said gasket with said outlet unit and said nut, said first opening being exposed through said nut,
wherein said first and second openings are diametrically opposite when said inlet is secured to said outlet unit, and said filter structure is exposed for observation or manipulation through said first opening;
passing a sample through said microfilter; and
performing an assay of material collected on said microfilter without removing said microfilter from said filter holder.

24. A container comprising:
a third volume for accommodating a fluid;
an inlet opening to an interior of said third volume; and
an outlet opening configured to accommodate a connection to a filter holder,
wherein
said filter holder comprises:
an inlet unit including a first volume and a first opening to said first volume; and
an outlet unit including a second volume for accommodating a filter structure removably configured therein, and a second opening to said second volume,
wherein said first and second openings are at opposite ends of said filer holder when said inlet unit is secured to said outlet unit, and said filter structure is exposed for observation of filtered substance collected on said filter structure and for performing an assay on said filtered substance within said first volume through said first opening; and
said outlet opening connects to said first opening of said filter holder.

25. The container of claim 24, further comprising an inlet adapter configured to communicatively connect said outlet opening to said first opening of said filter holder.

26. A system comprising:
a filter holder comprising
an inlet unit including a first volume and a first opening to said first volume; and
an outlet unit including a second volume for accommodating a filter structure removably configured therein, and a second opening to said second volume,
wherein said first and second openings are at opposite ends of said filter holder when said inlet unit is secured to said outlet unit, and said filter structure is exposed for observation of filtered substance collected on said filter structure and for performing an assay on said filtered substance within said first volume through said first opening;
an input container comprising
an input container volume for accommodating a fluid,
a first input container opening to an interior of said input container volume for placing a sample into said input container volume, and
a second input container opening configured to accommodate a connection to said first opening of said inlet unit; and
an outlet container comprising
an output container volume for accommodating a fluid,
a first output container opening to an interior of said volume, said first output container opening configured to accommodate a connection to said second opening of said outlet unit, and
a second output container opening to an interior of said output container volume to selectively release said sample;
wherein, when a suction force is applied at said second output container opening, said sample passes from said input container to said output container through said first and second openings of said filter holder via said filter structure to collect said filtered substance on said filter structure.

27. The system as claimed in claim 26, wherein said output container is configured as one of syringe pump or a vacutainer.

28. A system comprising:
a filter holder comprising
an inlet unit including a first volume and a first opening to said first volume; and
an outlet unit including a second volume for accommodating a filter structure removably configured therein, and a second opening to said second volume,
wherein said first and second openings are at opposite ends of said filter holder when said inlet unit is secured to said outlet unit, and said filter structure is exposed for observation of filtered substance collected on said filter structure and for performing an assay on said filtered substance within said first volume through said first opening;
a needle selectively attachable to said filter holder at said first opening of said inlet unit; and
a vacutainer holder comprising
a first vacutainer opening for insertion of a vacutainer, and
a second vacutainer opening in communication with said second opening of said outlet unit,
wherein, when a vacutainer is inserted into the vacutainer holder, a suction force is applied at said second vacutainer opening, whereby said sample passes via said needle to said vacutainer through said first and second openings of said filter holder via said filter structure to collect said filtered substance on said filter structure.

29. The filter holder of claim 1 further comprising a well unit,
  said well unit including a third volume and a third opening to said third volume,
  wherein said well unit is secured within at least one of said inlet unit and said out let unit when said inlet unit is secured to said outlet unit, and said filter structure is exposed for observation or manipulation within said second volume through said first opening and said third opening.

30. The filter holder of claim 29, wherein said well unit is configured to accommodate a liquid selectively placed therein in communication with said filter structure.

31. The filter holder of claim 30, wherein said filter structure comprises a hydrophobic characteristic.

* * * * *

() EX PARTE REEXAMINATION CERTIFICATE (11566th)

United States Patent
Tang et al.

(10) Number: US 9,658,207 C1
(45) Certificate Issued: Aug. 27, 2019

(54) POLYMER MICROFILTRATION DEVICES, METHODS OF MANUFACTURING THE SAME AND THE USES OF THE MICROFILTRATION DEVICES

(71) Applicant: Creatv Microtech, Inc., Potomac, MD (US)

(72) Inventors: Cha-Mei Tang, Potomac, MD (US); Yunqi Zhang, Gaithersburg, MD (US)

(73) Assignee: CREATV MICROTECH, INC., Potomac, MD (US)

Reexamination Request:
No. 90/014,203, Oct. 17, 2018

Reexamination Certificate for:
Patent No.: 9,658,207
Issued: May 23, 2017
Appl. No.: 14/359,467
PCT Filed: Nov. 21, 2012
PCT No.: PCT/US2012/066390
§ 371 (c)(1),
(2) Date: May 20, 2014
PCT Pub. No.: WO2013/078409
PCT Pub. Date: May 30, 2013

Related U.S. Application Data

(63) Continuation-in-part of application No. PCT/US2011/030966, filed on Apr. 1, 2011.

(60) Provisional application No. 61/654,636, filed on Jun. 1, 2012, provisional application No. 61/618,641, filed on Mar. 30, 2012, provisional application No. 61/562,404, filed on Nov. 21, 2011.

(51) Int. Cl.
*B01D 39/16* (2006.01)
*G01N 33/50* (2006.01)
*B01D 29/00* (2006.01)
*G01N 1/40* (2006.01)
*B01L 3/00* (2006.01)
*B01L 9/00* (2006.01)

(52) U.S. Cl.
CPC ......... *G01N 33/5005* (2013.01); *B01D 29/00* (2013.01); *B01D 39/16* (2013.01); *B01D 39/1692* (2013.01); *B01L 3/50* (2013.01); *B01L 3/5635* (2013.01); *B01L 9/00* (2013.01); *G01N 1/4005* (2013.01); *G01N 1/4077* (2013.01); *B01L 3/502* (2013.01);
(Continued)

(58) Field of Classification Search
None
See application file for complete search history.

(56) References Cited

To view the complete listing of prior art documents cited during the proceeding for Reexamination Control Number 90/014,203, please refer to the USPTO's public Patent Application Information Retrieval (PAIR) system under the Display References tab.

*Primary Examiner* — Elizabeth L McKane

(57) ABSTRACT

A microfilter comprising a polymer layer formed from epoxy-based photo-definable dry film, and a plurality of apertures each extending through the polymer layer. A microfilter comprising two or more polymer layers formed from epoxy-based photo-definable dry film, and a plurality of apertures or open areas each extending through the polymer layer. A method of forming a microfilter is also disclosed. The method includes providing a first layer of epoxy-based photo-definable dry film disposed on a substrate, exposing the first layer to energy through a mask to form a pattern, defined by the mask, in the first layer of dry film, forming, from the exposed first layer of dry film, a polymer layer having a plurality of apertures extending therethrough, the plurality of apertures having a distribution defined by the pattern, and removing the polymer layer from the substrate. Unique filter holder designs and methods appropriate to hold microfilters to collect the rare cells and allow performing assays in the filter holder are provided. The invention also describes the use of the microfilter and filter holder to collect rare cells from body fluids and
(Continued)

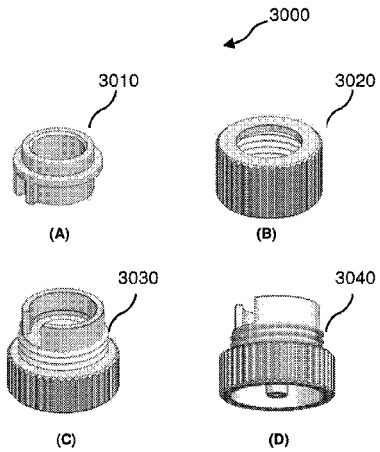

perform assays. Rare cells collected on the microfilter in accordance with embodiments of the present invention can be used for medical and biological research applications.

(52) U.S. Cl.
CPC ................ *B01L 2300/0681* (2013.01); *G01N 2001/4088* (2013.01); *Y10T 29/49826* (2015.01); *Y10T 29/49963* (2015.01)

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1, 5, 13, 15, 22-26, 28 and 29 are determined to be patentable as amended.

Claims 3, 4, 6-12, 14, 16-21, 27, 30 and 31, dependent on an amended claim, are determined to be patentable.

1. A filter holder comprising:
an inlet unit including a first volume and a first opening to said first volume; [and]
an outlet unit including a second volume for accommodating a filter structure removably configured therein, and a second opening to said second volume,
wherein said first and second openings are at opposite ends when said inlet unit is secured to said outlet unit, and said filter structure is exposed for observation of filtered substance collected on said filter structure and for performing an essay on said filtered substance within said first volume through said first opening*; and*
*a nut configured to removably attach to said outlet unit and removably secure said inlet unit to said outlet unit, wherein said first opening is exposed through said nut.*

5. [The] *A* filter holder [of claim 4] *comprising:*
*an inlet unit including a first volume and a first opening to said first volume;*
*an outlet unit including a second volume for accommodating a filter structure removably configured therein, and a second opening to said second volume,*
*wherein said first and second openings are at opposite ends when said inlet unit is secured to said outlet unit, and said filter structure is exposed for observation of filtered substance collected on said filter structure and for performing an essay on said filtered substance within said first volume through said first opening; and*
*a first gasket disposed in said second volume with respect to said filter structure,* wherein:
*said gasket includes a third opening aligned with said first opening and said second opening;*
said second volume includes a substantially circular seat for accommodating said gasket;
a diameter of said filter structure is essentially equal to an outer diameter of said gasket and an outer diameter of said seat; and
said inlet unit, said gasket and said filter structure are removably secured with said outlet unit by [said] *a* nut, whereby said filter structure remains flat and experiences compression to form a tight seal with said inlet unit and said outlet unit, without experiencing a twisting force.

13. The filter holder of claim [2] *1*, wherein said inlet unit further comprises an inlet adapter including an adapter input for attachment of a sample input container thereto and an adapter output in communication with said first volume allowing passage of at least a portion of a sample material from said sample input container to said first volume, wherein said adapter input extends through said nut whereby said first opening is exposed through said nut.

15. [The] *A* filter holder [of claim 1] *comprising:*
*an inlet unit including a first volume and a first opening to said first volume; and*
*an outlet unit including a second volume for accommodating a filter structure removably configured therein, and a second opening to said second volume,* wherein:
*said first and second openings are at opposite ends when said inlet unit is secured to said outlet unit, and said filter structure is exposed for observation of filtered substance collected on said filter structure and for performing an essay on said filtered substance within said first volume through said first opening;*
said inlet unit includes a fourth opening to said first volume diametrically opposite and aligned with said first opening;
said outlet unit includes a fifth opening to said second volume diametrically opposite and aligned with said second opening; and
said fourth opening essentially overlaps said fifth opening when said inlet unit and said outlet unit are secured.

22. The filter holder of any of [claim 1] *claims 1 or 3 through 21*, wherein said filter structure comprises:
a polymer layer formed from epoxy-based photo-definable material; and
a plurality of apertures each extending through the polymer layer.

23. A method of performing an essay comprising:
positioning a microfilter into a filter folder as claimed in any of claims 1 *or 3* through 21
selectively placing a filter into an outlet unit, the outlet unit including a seat for removably accommodating said filter or a gasket, and a second opening therethrough to facilitate attachment of an output container thereto;
removably placing said gasket onto said filter or under said filter, wherein a diameter of said filter is essentially equal to an outer diameter of said gasket and an outer diameter of said seat;
removably placing an inlet unit onto said filter when said gasket is under said filter, or removably placing said inlet unit onto said gasket when said gasket is on said filter, said inlet unit including a first opening opposite to said second opening;
installing a nut onto said outlet unit to removably secure said inlet unit, said filter, and said gasket with said outlet unit and said nut, said first opening being exposed through said nut,
wherein said first and second openings are diametrically opposite when said inlet is secured to said outlet unit, and said filter structure is exposed for observation or manipulation through said first opening;
passing a sample through said microfilter; and
performing an assay of material collected on said microfilter without removing said microfilter from said filter holder.

24. A [container] *system* comprising:
*a filter holder as claimed in any of claims 1, 5, 15, or 29;*
a third volume for accommodating a fluid;
an inlet opening to an interior of said third volume; and
an outlet opening configured to accommodate a connection to [a] *said* filter holder[,
wherein
said filter holder comprises:
an inlet unit including a first volume and a first opening to said first volume; and an outlet unit including a second volume for accommodating a filter structure removably configured therein, and a second opening to said second volume, wherein said first and second openings are at opposite ends of said filer holder when said inlet unit is secured to said outlet unit, and said filter structure is exposed for observation of filtered substance collected on said filter structure and for performing an essay on said filtered substance within said first volume through said first opening]; and said outlet opening connects to said first opening of said filter holder.

25. The [container] *system* of claim 24, further comprising an inlet adapter configured to communicatively connect said outlet opening to said first opening of said filter holder.

26. A system comprising:
a filter holder [comprising
an inlet unit including a first volume and a first opening to said first volume; and
an outlet unit including a second volume for accommodating a filter structure removably configured therein, and a second opening to said second volume,
wherein said first and second openings are at opposite ends of said filter holder when said inlet unit is secured to said outlet unit, and said filter structure is exposed for observation of filtered substance collected on said filter structure and for performing an essay on said filtered substance within said first volume through said first opening] *as claimed in any of claims 1, 5, 15, or 29;*
an input container comprising
an input container volume for accommodating a fluid,
a first input container opening to an interior of said input container volume for placing a sample into said input container volume, and
a second input container opening configured to accommodate a connection to said first opening of said inlet unit; and
an outlet container comprising
an output container volume for accommodating a fluid,
a first output container opening to an interior of said volume, said first output container opening configured to accommodate a connection to said second opening of said outlet unit, and
a second output container opening to an interior of said output container volume to selectively release said sample;
wherein, when a suction force is applied at said second output container opening, said sample passes from said input container to said output container through said first and second openings of said filter holder via said filter structure to collect said filtered substance on said filter structure.

28. A system comprising:
a filter holder [comprising
an inlet unit including a first volume and a first opening to said first volume; and
an outlet unit including a second volume for accommodating a filter structure removably configured therein, and a second opening to said second volume,
wherein said first and second openings are at opposite ends of said filter holder when said inlet unit is secured to said outlet unit, and said filter structure is exposed for observation of filtered substance collected on said filter structure and for performing an essay on said filtered substance within said first volume through said first opening;
a needle selectively attachable to said filter holder at said first opening of said inlet unit] *as claimed in any of claims 1, 5, 15, or 29;* and
a vacutainer holder comprising
a first vacutainer opening for insertion of a vacutainer, and
a second vacutainer opening in communication with said second opening of said outlet unit,
wherein, when a vacutainer is inserted into the vacutainer holder, a suction force is applied at said second vacutainer opening, whereby said sample passes via said needle to said vacutainer through said first and second openings of said filter holder via said filter structure to collect said filtered substance on said filter structure.

29. [The] *A* filter holder [of claim 1 further] comprising*:*
*an inlet unit including a first volume and a first opening to said first volume;*
*an outlet unit including a second volume for accommodating a filter structure removably configured therein, and a second opening to said second volume,*
*wherein said first and second openings are at opposite ends when said inlet unit is secured to said outlet unit, and said filter structure is exposed for observation of filtered substance collected on said filter structure and for performing an essay on said filtered substance within said first volume through said first opening; and*
a well unit,
said well unit including a third volume and a third opening to said third volume,
wherein said well unit is secured within at least one of said inlet unit and said out let unit when said inlet unit is secured to said outlet unit, and said filter structure is exposed for observation or manipulation within said second volume through said first opening and said third opening.

* * * * *